(12) United States Patent
Brun Torres et al.

(10) Patent No.: US 12,584,116 B2
(45) Date of Patent: Mar. 24, 2026

(54) ATTENUATED VARIANT OF THE RIFT VALLEY FEVER VIRUS, COMPOSITION COMPRISING SAME, AND USES THEREOF

(71) Applicant: CONSEJO SUPERIOR DE INVESTIGACIONES CIENTÍFICAS (CSIC), Madrid (ES)

(72) Inventors: Alejandro Brun Torres, Madrid (ES); María Belén Borrego Rivero, Madrid (ES); Sandra Moreno Fernández, Madrid (ES)

(73) Assignee: CONSEJO SUPERIOR DE INVESTIGACIONES CIENTÍFICAS (CSIC) (ES)

( * ) Notice: Subject to any disclaimer, the term of this patent is extended or adjusted under 35 U.S.C. 154(b) by 706 days.

(21) Appl. No.: 18/000,558

(22) PCT Filed: Jun. 3, 2021

(86) PCT No.: PCT/ES2021/070403
§ 371 (c)(1),
(2) Date: Dec. 2, 2022

(87) PCT Pub. No.: WO2021/245313
PCT Pub. Date: Dec. 9, 2021

(65) Prior Publication Data
US 2023/0212529 A1    Jul. 6, 2023

(30) Foreign Application Priority Data

Jun. 4, 2020    (ES) .................................. 202030529

(51) Int. Cl.
*C12N 7/00*        (2006.01)
*A61K 39/12*      (2006.01)
(Continued)

(52) U.S. Cl.
CPC ................ *C12N 7/00* (2013.01); *A61K 39/12* (2013.01); *A61P 31/14* (2018.01); *C07K 14/005* (2013.01);
(Continued)

(58) Field of Classification Search
None
See application file for complete search history.

(56) References Cited

U.S. PATENT DOCUMENTS

2023/0212529 A1*    7/2023   Brun Torres ............. C12N 7/00
424/186.1

OTHER PUBLICATIONS

Ebisine et al. (Pathogens 2024, 13, 856).*
(Continued)

*Primary Examiner* — Shanon A. Foley
(74) *Attorney, Agent, or Firm* — Casimir Jones, S.C.; Tristan A. Fuierer

(57)    ABSTRACT

The invention relates to an attenuated variant of the Rift Valley Fever Virus (RVFV) with mutations in the amino acid sequence coded by segments L, M and S of RVFV RNA; a pharmaceutical or veterinary composition comprising same; an attenuated RVFV variant for use in the prevention of Rift Valley Fever, and a vaccine against Rift Valley Fever comprising the attenuated RVFV variant. Attenuated RVFV variants with the mutations Gly924Ser and Ala303Thr in protein L, and the Pro82Leu substitution in protein NSs, are also included.

12 Claims, 7 Drawing Sheets
Specification includes a Sequence Listing.

(51) Int. Cl.
| | |
|---|---|
| *A61P 31/14* | (2006.01) |
| *C07K 14/005* | (2006.01) |
| *A61K 39/00* | (2006.01) |

(52) U.S. Cl.
CPC .. *A61K 2039/5254* (2013.01); *A61K 2039/54* (2013.01); *A61K 2039/552* (2013.01); *C12N 2760/12221* (2013.01); *C12N 2760/12222* (2013.01); *C12N 2760/12234* (2013.01); *C12N 2760/12271* (2013.01)

(56) References Cited

OTHER PUBLICATIONS

Borrego et al. (Viruses. Mar. 2021; 13: 542).*
Borrego et al. (Frontiers in Microbiology. Feb. 2021; 11: 621463).*
Moreno et al. (Viruses. 2024; 16: 87).*
Amroun et al., Bunyaviridae RdRps: structure, motifs, and RNA synthesis machinery. Crit Rev Microbiol. Nov. 2017;43(6):753-778.
Bird et al., Complete genome analysis of 33 ecologically and biologically diverse Rift Valley fever virus strains reveals widespread virus movement and low genetic diversity due to recent common ancestry. J Virol. Mar. 2007;81(6):2805-16.
Borrego et al., A Hyper-Attenuated Variant of Rift Valley Fever Virus Generated by a Mutagenic Drug (Favipiravir) Unveils Potential Virulence Markers. Front Microbiol. Feb. 9, 2021;11:621463. 16 pages.
Borrego et al., Lethal Mutagenesis of Rift Valley Fever Virus Induced by Favipiravir. Antimicrob Agents Chemother. Jul. 25, 2019;63(8):e00669-19. 9 pages.
Borrego et al., The Change P82L in the Rift Valley Fever Virus NSs Protein Confers Attenuation in Mice. Viruses. Mar. 24, 2021;13(4):542. 13 pages.
Bouloy et al., Genetic evidence for an interferon-antagonistic function of rift valley fever virus nonstructural protein NSs. J Virol. Feb. 2001;75(3):1371-7.
Busquets et al., Experimental infection of young adult European breed sheep with Rift Valley fever virus field isolates. Vector Borne Zoonotic Dis. Oct. 2010;10(7):689-96.
GenBank Accession Nos. KU167025-KU167027. Lumley. May 5, 2016. 4 pages.

Ikegami et al., Rift Valley Fever Virus MP-12 Vaccine Is Fully Attenuated by a Combination of Partial Attenuations in the S, M, and L Segments. J Virol. Jul. 2015;89(14):7262-76.
Lumley et al., Complete Genome Sequence of Rift Valley Fever Virus Strain Lunyo. Genome Announc. Apr. 14, 2016;4(2):e00170-16. 2 pages.
Ly et al., Attenuation and protective efficacy of Rift Valley fever phlebovirus rMP12-GM50 strain. Vaccine. Dec. 4, 2017;35(48 Pt B):6634-6642.
Terasaki et al., Mechanistic Insight into the Host Transcription Inhibition Function of Rift Valley Fever Virus NSs and Its Importance in Virulence. PLoS Negl Trop Dis. Oct. 6, 2016;10(10):e0005047. 22 pages.
International Search Report and Written Opinion for PCT/ES2021/070403. Mailed Sep. 20, 2021. 29 pages.
Borrego, et al., The Rift Valley fever (RVF) vaccine candidate 40Fp8 shows an extreme attenuation in IFNARKO mice following intranasal inoculation. PLoS Negl Trop Dis. 18(8):e0012011 (Aug. 19, 2024).
Borrego, et al., The 40Fp8 vaccine strain is safe and protects pregnant ewes from a virulent RVFV challenge. NPJ Vaccines. 10(1):206 (Aug. 29, 2025).
Doyle, et al., Immune correlates of protection following Rift Valley fever virus vaccination. NPJ Vaccines. 7(1):129 (Oct. 28, 2022).
Morrill, et al., Pathogenicity and immunogenicity of a mutagen-attenuated Rift Valley fever virus immunogen in pregnant ewes. Am J Vet Res. 48(7):1042-7 (Jul. 1987).
Morrill, et al., Safety of a mutagen-attenuated Rift Valley fever virus vaccine in fetal and neonatal bovids. Am J Vet Res. 58(10):1110-4 (Oct. 1997).
Pittman et al., Safety and immunogenicity of a mutagenized, live attenuated Rift Valley fever vaccine, MP-12, in a Phase 1 dose escalation and route comparison study in humans. Vaccine. 34(4):424-429 (Jan. 20, 2016).
Watts, et al., Estimation of the Minimal Rift Valley Fever Virus Protective Neutralizing Antibody Titer in Human Volunteers Immunized with MP-12 Vaccine Based on Protection in a Mouse Model of Disease. Am J Trop Med Hyg. 107(5):1091-1098 (Sep. 19, 2022).
Watts, et al., Minimal Protective Antibody Titers Elicited in Sheep by RVFV MP-12 and arMP-12ΔNSm21/384 Vaccine Candidates. Int J Vet Sci Res. 10(3):046-062 (2024).

* cited by examiner

ATTENUATED VARIANT OF THE RIFT VALLEY FEVER VIRUS, COMPOSITION COMPRISING SAME, AND USES THEREOF

CROSS-REFERENCE TO RELATED APPLICATIONS

This application is filed under the provisions of 35 U.S.C. § 371 and claims the priority of International Patent Application No. PCT/ES2021/070403, filed on 3 Jun. 2021 entitled "ATTENUATED VARIANT OF THE RIFT VAL-LEY FEVER VIRUS, COMPOSITION COMPRISING SAME, AND USES THEREOF" in the name of Alejandro BRUN TORRES, et al., which claims priority to Spanish Patent Application No. P202030529 filed on 4 Jun. 2020, both of which are hereby incorporated by reference herein in their entirety.

TECHNICAL FIELD OF THE INVENTION

The present invention relates to live vaccines for attenuated Rift Valley Fever (RVF), a disease caused by the Rift Valley Fever virus (RVFV). In particular, the invention relates to an attenuated variant of RVFV obtained by mutagenic treatment with favipiravir.

BACKGROUND OF THE INVENTION

The Rift Valley fever virus (RVFV) is a mosquito-borne bunyavirus that belongs to the Phenuiviridae family of the genus Phlebovirus. RVFV causes Rift Valley Fever (RVF) in ruminants, which after epizootic outbreaks, is transmitted to humans mainly through mosquito bites.

Rift Valley Fever is currently present in the African continent, in the southern Arabian Peninsula and in the Indian Ocean islands. In addition, RVF has the potential to extend to other geographical areas, in particular in relation to climate change and globalization. Currently, there is no treatment or vaccine against Rift Valley Fever on the market.

RVFV is an RNA virus. The structure of the RVFV virion consists of a lipid envelope with two membrane glycoproteins (Gn and Gc) arranged in an icosahedral lattice that protects an internal nucleocapsid composed of the viral nucleoprotein (N) and an RNA-dependent polymerase (RdRp) linked to the viral RNA.

The RVFV genome is made up of three segments of single-stranded RNA of different size (large (L), medium (M), small(S)) with negative polarity (L and M) or bipolarity(S). The L segment encodes the RNA-dependent RNA polymerase (RdRp). The M segment encodes for two 78 kDa and 13-14 kDa non-structural proteins (NSm) and for Gn and Gc membrane glycoproteins. The S segment encodes a 27 kDa non-structural protein (NSs), considered the primary virulence factor of the virus, as well as the N protein.

Live attenuated vaccines induce long-lasting and highly protective immunity after single-dose administration in both animals and humans. They are called live vaccines because they contain the microorganism causing the infection in a live or viable form, but with a very reduced (attenuated) capacity for infection, reproduction or, in general, virulence. This makes live attenuated vaccines an excellent basis for the development of successful immunization programs in the affected countries or to implement preventive control measures in countries with a higher risk of introduction or expansion of the disease.

Mutagenic treatments have frequently been used as viral attenuation methods. One example of this is the MP-12 live attenuated FVR vaccine (Ikegami et al., 2015), obtained by mutagenic treatment with 5-fluorouracil. Currently, the MP-12 vaccine is in phase II trials as a vaccine candidate for humans.

Nucleoside analogues with antiviral activity against RVFV have been described, such as ribavirin (1-β-D-ribo-furanosyl-1-H-1,2,4-triazole-3-carboxyamide), favipiravir (6-fluoro-3-hydroxy-2-pyrazinecarboxyamide) and BCX4430 [(2S,3S,4R,5R)-2-(4-amino-5H-pyrrolo[3,2-d] pyrimidin-7-yl)-5-(hydroxymethyl) pyrrolidine-3,4-diol] (galidesivir). Favipiravir is a pyrazine derivative (6-fluoro-3-hydroxy-2-pyrazinecarboxyamide) that acts as a pyrimidine analogue and has potent antiviral activity against different RNA viruses.

Favipiravir has mutagenic activity on several RNA viruses, including hepatitis C virus, foot-and-mouth disease virus, West Nile fever virus, norovirus, influenza virus and RVFV. It has been described in the prior art that the mechanism of action of favipiravir against RVFV is due to the accumulation of mutations in the viral genome leading to a progressive decrease of viable viral progeny (Borrego et al., 2019).

The development of live attenuated RVF vaccines is an active field of research and there is a need to develop new live attenuated RVF vaccines, which can serve to develop safe and effective RVF control strategies, for animal and/or human use.

DESCRIPTION OF THE INVENTION

For the purposes of the present invention, the amino acids are mentioned by their full name or are represented using the three-letter symbols of the IUPAC nomenclature, also used in the ST.25 standard for the presentation of lists of nucleotide and amino acid sequences in patent applications of the World Intellectual Property Organization (WIPO). Thus, for example, the amino acid alanine is represented by the symbol "Ala", the amino acid aspartic acid is represented by "Asp", etc.

For the purposes of the present invention, nucleotide sequences of RNA molecules are described by the corresponding nucleotide sequence of DNA molecules. It is known in the art how to determine RNA sequences from the corresponding DNA sequences, which is performed by replacing the thymine nucleotides with uracil nucleotides.

For the purposes of the present invention, "multiplicity of infection (MOI)" refers to the ratio of agents (e.g., viruses) to infection targets (e.g., cells). By way of example, when referring to a group of cells inoculated with virus particles, the multiplicity of infection or MOI is the ratio between the number of virus particles and the number of target cells present.

For the purposes of the present invention, the term "ELISA" refers to enzyme-linked immunoabsorbent assay, which is an immunoassay technique in which an immobilized antigen is detected by an antibody bound to an enzyme (peroxidase, alkaline phosphatase, etc.,) capable of generating a detectable product from a substrate by a colour change or some other type of change caused by the enzymatic action on said substrate. In said technique, there may be a primary antibody that recognizes the antigen and that in turn is recognized by a secondary antibody bound to said enzyme. The antigen can be detected indirectly in the sample by colour changes measured by spectrophotometry.

For the purposes of the present invention, "challenge", in the context of immunology, refers to the deliberate exposure of an animal to an infectious agent, e.g., a virus, to study the response of the animal to exposure to said infectious agent. The dose used in the challenge is called the "challenge dose".

For the purposes of the present invention, RACE (Rapid amplification of cDNA ends) refers to a technique of rapid amplification of complementary DNA (cDNA) ends. RACE is a technique used in molecular biology to obtain the full-length sequence of an RNA molecule, in which a cDNA copy of the RNA sequence of interest is produced by reverse transcription, followed by polymerase chain reaction (PCR) amplification of the cDNA copies.

For the purposes of the present invention, "ANOVA" or "analysis of variance" is a set of statistical models used to analyze differences between means within a statistical sample. ANOVA is based on the law of total variance, where the variance observed in a particular variable is divided into components attributable to different sources of variation. ANOVA provides a statistical test to determine if two or more population means are the same.

The present invention provides an attenuated variant of Rift Valley Fever Virus (RVFV), wherein:

in the RdRp protein encoded by the L segment of the RNA of said variant:
the amino acid of position 924 is serine (L[Gly924Ser]); and
the amino acid at position 1303 is threonine (L[Ala1303Thr]);
wherein the sequence SEQ ID NO: 47 of wild strain 56/74 of the RVF virus or the sequence SEQ ID NO: 54 of wild-type strain ZH548 of the RVF virus, are the reference sequences for amino acid numbering of said protein; and
in the NSs protein encoded by the S segment of the RNA of said variant:
the amino acid at position 82 is leucine (NSs [Pro82Leu]);
wherein the sequence SEQ ID NO: 49 of wild strain 56/74 of the RVF virus or the sequence SEQ ID NO: 56 of the wild type ZH548 strain of the RVF virus, are the reference sequences for the numbering of the amino acids of said protein.

In one embodiment of the variant of the RVFV of the invention, further:

in the RdRp protein encoded by the L segment of the RNA of said variant:
the amino acid at position 100 is threonine (L[Met100Thr]);
the amino acid at position 375 is tyrosine (L[His375Tyr]);
the amino acid at position 1050 is valine (L[Ile1050Val]);
the amino acid at position 1629 is phenylalanine (L[Leu1629Phe]); and
the amino acid at position 2071 is lysine (L[Glu2071Lys]);
wherein the sequence SEQ ID NO: 47 of wild strain 56/74 of the RVF virus or the sequence SEQ ID NO: 54 of the wild type ZH548 strain of the RVF virus, are the reference sequences for the numbering of the amino acids of said protein;
in the amino acid sequence encoded by the M segment of the RNA of said variant:
the amino acid at position 26 is lysine (M[Arg26Lys]);
the amino acid at position 108 is tyrosine (M[His108Tyr]);
the amino acid at position 118 is lysine (M[Glu118Lys]);

the amino acid at position 210 is lysine (M[Arg210Lys]);
the amino acid at position 333 is asparagine (M[Asp333Asn]);
the amino acid at position 427 is threonine (M[Ala427Thr]);
the amino acid at position 432 is valine (M[Ala432Val]);
the amino acid at position 487 is glycine (M[Glu487Gly]);
the amino acid at position 540 is tyrosine (M[His540Tyr]);
the amino acid at position 582 is threonine (M[Ala582Thr]);
the amino acid at position 587 is isoleucine (M[Val587Ile]);
the amino acid at position 950 is valine (M[Ala950Val]);
the amino acid at position 1090 is isoleucine (M[Val1090Ile]);
the amino acid at position 1116 is valine (M[Ala1116Val]); and
the amino acid at position 1182 is lysine (M[Arg1182Lys]);
wherein the sequence SEQ ID NO: 48 of wild strain 56/74 of the RVF virus or the sequence SEQ ID NO: 55 of the wild strain ZH548 of the RVF virus, are the reference sequences for amino acid numbering of said amino acid sequence encoded by the M segment of the RNA of said variant;
in the NSs protein encoded by the S segment of the RNA of said variant:
the amino acid at position 52 is isoleucine (NSs [Val52Ile]);
wherein the sequence SEQ ID NO: 49 of wild strain 56/74 of the RVF virus or the sequence SEQ ID NO: 56 of the wild type ZH548 strain of the RVF virus, are the reference sequences for the numbering of the amino acids of said protein.

In one embodiment of the attenuated variant Rift Valley fever virus (RVFV):

in the amino acid sequence encoded by the L segment of the RNA of said variant:
the amino acid at position 100 is threonine;
the amino acid at position 375 is tyrosine;
the amino acid at position 924 is serine;
the amino acid at position 1050 is valine;
the amino acid at position 1303 is threonine;
the amino acid at position 1629 is phenylalanine; and
the amino acid at position 2071 is lysine;
in the amino acid sequence encoded by the M segment of the RNA of said variant:
the amino acid at position 26 is lysine;
the amino acid at position 108 is tyrosine;
the amino acid at position 118 is lysine;
the amino acid at position 210 is lysine;
the amino acid at position 333 is asparagine;
the amino acid at position 427 is threonine;
the amino acid at position 432 is valine;
the amino acid at position 487 is glycine
the amino acid at position 540 is tyrosine;
the amino acid at position 582 is threonine;
the amino acid at position 587 is isoleucine;
the amino acid at position 950 is valine;
the amino acid at position 1090 is isoleucine;
the amino acid at position 1116 is valine; and
the amino acid at position 1182 is lysine;

in the amino acid sequence encoded by the S segment of the RNA of said variant:

the amino acid at position 52 is isoleucine; and the amino acid at position 82 is leucine;

wherein said amino acids correspond to amino acid substitutions of the sequence of wild strain 56/74 of the RVF virus.

In one embodiment of the RVFV variant of the invention, the amino acid sequence encoded by the L segment of the RNA of said variant is SEQ ID NO: 4; the amino acid sequence encoded by the M segment of the RNA of said variant is SEQ ID NO: 5; the NSs protein consists of the sequence SEQ ID NO: 6; and the N protein consists of the sequence SEQ ID NO: 7.

In the present disclosure, the amino acid sequence encoded by the L segment of the RNA of wild strain 56/74 of the RVF virus is SEQ ID NO: 47; the amino acid sequence encoded by the M segment of the RNA of wild strain 56/74 of the RVF virus is SEQ ID NO: 48; the NSs protein of the wild type 56/74 strain of the RVF virus consists of the sequence SEQ ID NO: 49; and the N protein of wild-type strain 56/74 of the RVF virus consists of the sequence SEQ ID NO: 50.

In the present disclosure, the amino acid sequence encoded by the L segment of the RNA of wild strain ZH548 of the RVF virus is SEQ ID NO: 54; the amino acid sequence encoded by the M segment of the RNA of the ZH548 wild strain of the RVF virus is SEQ ID NO: 55; the NSs protein of the wild type ZH548 strain of the RVF virus consists of the sequence SEQ ID NO: 56; and the N protein of the wild type ZH548 strain of the RVF virus consists of the sequence SEQ ID NO: 57.

In one embodiment of the RVFV variant of the invention, comprising an RNA encoding said variant, the L segment of said RNA consists of the sequence SEQ ID NO: 1; and the M segment of said RNA consists of the sequence SEQ ID NO: 2; and the S segment of said RNA consists of the sequence SEQ ID NO: 3.

In the present disclosure, the wild strain 56/74 of the RVF virus comprises an RNA encoding said wild strain, wherein the L segment of said RNA consists of the sequence SEQ ID NO: 44; and the M segment of said RNA consists of the sequence SEQ ID NO: 45; and the S segment of said RNA consists of the sequence SEQ ID NO: 46.

In the present disclosure, wild type strain ZH548 of the RVF virus comprises an RNA encoding said wild type strain, wherein the L segment of said RNA consists of the sequence SEQ ID NO: 51; and the M segment of said RNA consists of the sequence SEQ ID NO: 52; and the S segment of said RNA consists of the sequence SEQ ID NO: 53.

The present invention also provides a pharmaceutical or veterinary composition comprising the RVFV variant of the invention, together with at least one pharmaceutically acceptable excipient or for veterinary use.

The present invention also provides the RVFV variant of the invention for use as a medicament.

In one embodiment, the present invention provides the use of the RVFV variant of the invention for the manufacture of a medicament.

In another embodiment, the present invention provides a therapeutic method for preventing Rift Valley fever comprising administering to an animal an effective amount of the attenuated variant of the RVFV of the invention. Preferably, said animal is a human or a ruminant.

For the purposes of the present invention, "effective amount" refers to the amount of the RVFV variant of the invention that provides an objectively identifiable improvement in the state of the animal, recognized by a qualified observer, and wherein said animal is treated with a pharmaceutical composition comprising said amount of the RVFV variant.

Additionally, the present invention provides the RVFV variant of the invention for use in the prevention of Rift Valley fever.

In one embodiment, the present invention provides the use of the RVFV variant of the invention for the manufacture of a medicament for the prevention of Rift Valley fever. Preferably, said medicament is a vaccine.

In one embodiment, the RVFV variant of the invention is for use in animals.

In a preferred embodiment of the variant of the RVFV for use of the invention, said animals are ruminants. Preferably, said ruminants are selected from: cows, sheep, goats, camels and buffaloes.

The RVFV variant of the invention is for use in domestic ruminants and wild ruminants. In the use in wild ruminants, the RVFV variant of the invention is useful for preventing RVF in wild animals in reserves, zoos, etc. In fact, it is suspected that the African buffalo may be a carrier of the virus.

Thus, in one embodiment of the variant of the RVFV for use of the invention, such ruminants are domestic or wild ruminants.

In a preferred embodiment, said domestic ruminants are selected from: cows, sheep, goats and camels.

In another preferred embodiment, said wild ruminants are buffalo.

In another preferred embodiment, the RVFV variant of the invention is for use in humans.

The present invention also provides a Rift Valley fever vaccine comprising the RVFV variant of the invention.

In a preferred embodiment, the vaccine of the invention comprises at least one pharmaceutically acceptable excipient or for veterinary use.

For the purposes of the present invention, inert ingredients such as, but not limited to, buffers, co-solvents, surfactants, oils, humectants, emollients, preservatives, stabilizers, antioxidants, dyes, air protectors and/or moisture and binders are pharmaceutically acceptable excipients or for veterinary use. An example of a buffer is phosphate buffered saline (PBS).

In one embodiment, said pharmaceutical or veterinary composition comprises Dulbecco's Modified Eagle Medium (DMEM).

The pharmaceutical, veterinary composition or vaccine of the invention can be formulated with pharmaceutically acceptable excipients or for veterinary use, as well as with any other type of pharmaceutically acceptable carriers or diluents or for veterinary use, according to conventional techniques in pharmaceutical or veterinary practice.

The pharmaceutical, veterinary composition or the vaccine of the invention can be administrated in single or multiple doses.

The pharmaceutical, veterinary composition or the vaccine of the invention can be administered by any route of administration for which said composition will be formulated in the pharmaceutical form suitable for the chosen route of administration. Examples of routes of administration include, but are not limited to, subcutaneous, intravenous and intramuscular.

The present specification also provides primers for amplification of genomic regions of the RVF virus RNA comprising nucleic acids at least 80% identical to any of the sequences selected from: SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 24, SEQ ID NO: 25, SEQ ID NO: 26, SEQ ID NO: 27, SEQ ID NO: 28, SEQ ID NO: 29, SEQ ID NO: 32, SEQ ID NO: 33, SEQ ID NO: 34, SEQ ID NO: 35, SEQ ID NO: 36, SEQ ID NO: 38, SEQ ID NO: 39, SEQ ID NO: 40, SEQ ID NO: 41, SEQ ID NO: 42 and SEQ ID NO: 43.

In a preferred disclosure, said sequence identity is selected from: 81%, 82%, 83%, 84%, 85%, 86%, 87%, 88%, 89%, 90%, 91%, 92%, 93%, 94%, 95%, 96%, 97%, 98%, 99% and 100%.

In a more preferred disclosure, said primers of the invention consist of nucleic acids consisting of the sequences selected from: SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 24, SEQ ID NO: 25, SEQ ID NO: 26, SEQ ID NO: 27, SEQ ID NO: 28, SEQ ID NO: 29, SEQ ID NO: 32, SEQ ID NO: 33, SEQ ID NO: 34, SEQ ID NO: 35, SEQ ID NO: 36, SEQ ID NO: 38, SEQ ID NO: 39, SEQ ID NO: 40, SEQ ID NO: 41, SEQ ID NO: 42 and SEQ ID NO: 43.

In one disclosure of such primers of the invention, said RNA is from the RVFV variant of the invention or from the wild strain 56/74 of the RVFV.

DESCRIPTION OF EMBODIMENTS

Materials and Methods

Cells, Viruses and Infections

Figure 1:
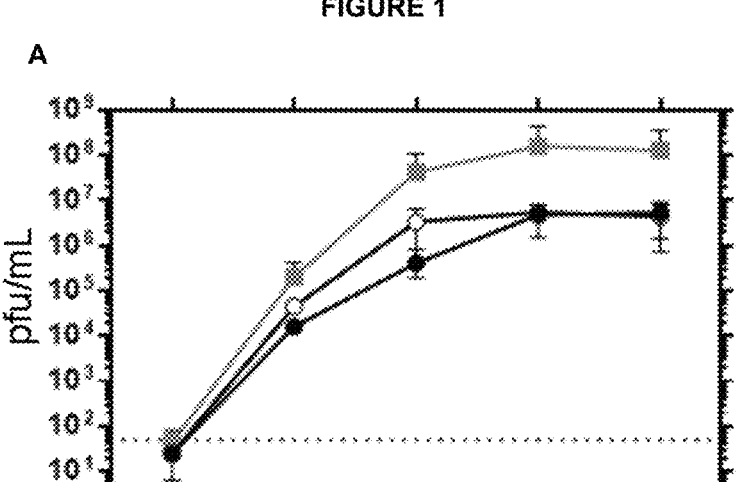
FIG. 1. Growth kinetics in mammalian and insect cells. Vero (A) cells and C6/36 mosquito cells (B) were infected with a multiplicity of infection (MOI) of 0.01 or 0.005 respectively, with the FMH-P8 RVF virus (squares), the parental RVF virus 56/74 after 8 passes (open circles) and before such passes (closed circles). hpi represents hours post infection and dpi represents days post infection. After one hour of adsorption the inoculum was removed, the cells washed and new medium was added. The supernatants were collected at different times post infection (pi) and assayed in Vero cell monolayers by a standard plate assay using semi-solid medium. The monolayers were fixed and stained 4 days post infection. Assessments were performed at least twice. The mean values plus the standard deviation represented by an asterisk have $p<0.05$ (multiple t-test). The data shown correspond to a representative experiment. C. Plate phenotype of the indicated viruses in Vero cell monolayers with the parental virus RVFV 56/74 after 8 passes (center), before said passes (left) and with the FMH-P8 RVF virus (right). The infection was performed in semi-solid medium. The monolayers were fixed and stained 4 days post infection.
Figure 1:
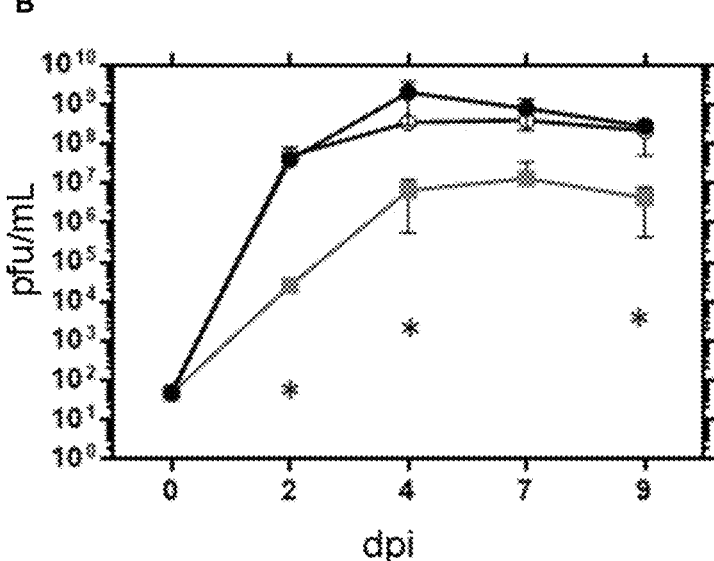
Figure 1:
Figure 1:
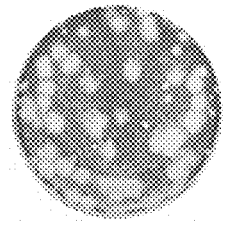
Figure 1:
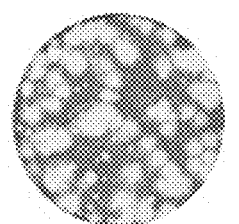
Figure 1:
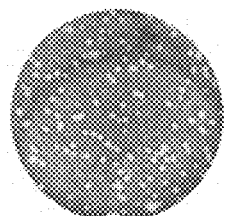

Vero cells (ATCC No. Catalogue CCL-81) were grown in Dulbecco's Modified Eagle Medium (DMEM) supplemented with 5% to 10% fetal calf serum (FCS) and L-glutamine (2 mM), penicillin (100 U/ml) and streptomycin (100 g/ml) in a humid atmosphere of 5% $CO_2$ at 37° C. Insect cells of *Aedes albopictus* C6/36 (ATCC No. Catalogue CRL1660) were grown in Eagle minimal essential medium (EMEM) supplemented with 10% fetal calf serum (FCS), L-glutamine (2 mM), gentamicin (50 µg/ml) and vitamin MEM solution (Sigma) in a humid atmosphere of 5% $CO_2$ at 28° C.

The starting parental virus originated in a sheep experimentally infected with wild strain 56/74 isolate of the VRVR 56/74 virus (parental virus) (Borrego et al., 2019); (Busquets et al., 2010). The virus was re-isolated from infected sheep plasma and cultured in a C6/36 mosquito cell line (ATCC CRL-1660). Assays to quantify plate-forming units (pfu) were performed in semi-solid medium including 1% carboxymethylcellulose (CMC; Sigma). pfu units are used in virology to describe the number of virus particles capable of forming plates per unit volume. Viral particles that are defective or that fail to infect their target cell will not form a plaque, and are not counted.

RNA Extraction, RT-PCR and Nucleotide Sequencing

RNA was extracted from the supernatants of the infected cells using the Speedtools RNA virus extraction kit (Biotools B&M Labs, S.A., Madrid, Spain) according to the manufacturer's instructions. Reverse transcription polymerase chain reaction (RT-PCR) was performed using SuperScript IV reverse transcriptase (Invitrogen) and Phusion high-fidelity DNA polymerase (Finnzymes), as directed by the manufacturers, using primers designed to amplify the L segments (Table 1A), M segments (Table 1B), and S segments (Table 1C) of the viral genome. Table 1D shows the primers used for the amplification of the genomic ends by the RACE technique. The overlapping PCR amplicons were purified and subjected to automatic Sanger sequencing. The Laser Gene software was used for the analysis of the results.

TABLE 1A

| Name | SEQ ID NO | Position/L segment | Orientation |
|---|---|---|---|
| 5' end L segment | 8 | 1-30 | Antigenomics |
| 716F | 9 | 716-732 | Antigenomics |
| L-F segment 1028ag | 10 | 1028-1044 | Antigenomics |
| L-R 2300g | 11 | 2281-2300 | Genomics |
| RdRp central-F | 12 | 2701-2723 | Antigenomics |
| L-F segment | 13 | 2872-2894 | Antigenomics |
| L-R segment | 14 | 3006-2984 | Antigenomics |
| Central RdRp-R | 15 | 3938-3960 | Antigenomics |
| 3817 F | 16 | 3817-3833 | Antigenomics |
| 4553 F | 17 | 4553-4569 | Antigenomics |
| 5455 F | 18 | 5455-5477 | Antigenomics |
| 5583 R | 19 | 5583-5567 | Antigenomics |
| Q3'25nts | 20 | 6361-6385 | Genomics |
| End q3'R L segment | 21 | 6369-6385 | Genomics |

TABLE 1B

| Name | SEQ ID NO | Position/M segment | Orientation |
|---|---|---|---|
| (−2)RTsm1 | 22 | 27-53 | Antigenomics |
| MRV1ag | 23 | 772-790 | Antigenomics |
| RTsm2 | 24 | 1953-1976 | Antigenomics |
| Sm2 | 25 | 2072-2095 | Genomics |
| Sm3 | 26 | 3200-3223 | Genomics |
| Sm4 | 27 | 3817-3838 | Genomics |
| EM-RVFV-R | 28 | 3867-3884 | Genomics |
| EM-RVFV-F | 29 | 3405-3424 | Antigenomics |

TABLE 1C

| Name | SEQ ID NO | Position/S segment | Orientation |
|---|---|---|---|
| NS0g | 30 | 1-19 | Antigenomics |
| NS2g | 31 | 61-80 | Antigenomics |
| R-S | 32 | 241-262 | Antigenomics |
| F-S | 33 | 338-361 | Genomics |
| NScag | 34 | 824-841 | Genomics |
| SS1 | 35 | 909-931 | Antigenomics |
| RTss1 | 36 | 1634-1663 | Genomics |
| NP0ag | 37 | 1670-1690 | Genomics |

TABLE 1D

| Name | SEQ ID NO | Position | Segment | Orientation |
|---|---|---|---|---|
| LsegcRNA | 38 | 349-366 | L | Genomics |
| LsegvRNA | 39 | 6011-6026 | L | Antigenomics |
| MsegcRNA | 40 | 393-409 | M | Genomics |
| MsegvRNA | 41 | 3544-3561 | M | Antigenomics |
| SsegcRNA | 42 | 296-313 | S | Genomics |
| SegvRNA | 43 | 1421-1437 | S | Antigenomics |

Experiments with Mice

Groups of transgenic 129Sv/Ev IFNAR$^{-/-}$ mice of 5-6 months of age or wild 129Sv/Ev mice of 11 months of age (B&K Universal) were inoculated intraperitoneally with different doses of the viruses, as indicated in the corresponding experiments. After viral inoculation, animals were monitored daily for weight and development of clinical signs, including signs on the coat, hunched posture, reduced activity, and conjunctivitis. At the indicated times, the animals were bled through the maxillary vein. Serums were inactivated by heat at 56° C. for 30 minutes and maintained at −20° C. until use. All mice were housed in a BSL-3 containment area with food and water supplied ad libitum. All experimental procedures were managed in accordance with the guidelines of the EU Directive 2010/63/EU for animal experiments and protocols approved by the Biosafety and Ethics Committees for Animal Experiments of INIA (EAEC permit codes 2012/014 and CBS 2012/017).

Sheep Experiments

Two ewes were inoculated with a dose of $10^7$ pfu of FMH-P8 and compared to three additional ewes inoculated with virus 56/74 (control group). One sheep from each group was slaughtered on day 4 post infection to analyze the degree of liver injury caused by the infection. Rectal temperature was taken daily after the challenge and blood and serum samples were taken daily for at least 8 consecutive days. The blood and serum samples obtained were used to perform a quantification of liver transaminase levels, as well as in vitro tests for neutralizing antibodies.

Antibody Assays

Neutralization tests were performed on 96-well culture plates following the test prescribed by the OIE (Chapter 2.1.14 OIE Terrestrial Manual 2012). Briefly, sera were diluted in base 2 from an initial 1/10 dilution in DMEM medium containing 2% fetal bovine serum, mixed with an equal volume of infectious virus containing 100 TCID$_{50}$ (50% infectious tissue culture dose) and incubated 30 minutes at 37° C. A suspension of Vero cells was then added and the plates were incubated for 4 days. The monolayers were controlled for the development of cytopathic effect, fixed and stained. Each sample was tested in 4 wells. The titer is expressed as the last dilution of serum that gives a reduction of the cytopathic effect in 50% of the wells.

For the detection of antibodies against the nucleoprotein (N protein), an ELISA assay was performed. The ELISA plates were adsorbed with 100 ng/well of recombinant N-protein produced in E. coli and purified, diluted in carbonate buffer (pH 9.6). After blocking with 5% skimmed milk-PBS-0.05% Tween 20, the sera were analyzed in duplicate in serial dilutions in base 3 starting at 1/50. The bound antibodies were detected with goat antibodies conjugated to horseradish peroxidase (HRP), mouse-HRP anti-IgG (H+L) (BioRad) and the bound conjugate was detected using 3,3',5,5'-tetramethylbenzidine (TMB, Invitrogen/Life Technologies) for 10 minutes, followed by a volume of stop solution (3N H$_2$SO$_4$). The optical densities were measured at 450 nm (OD$_{450}$).

Statistical Analysis

Data analysis was performed with GraphPad prism version 6 software.

Example 1. Obtaining FMH-P8 Attenuated RVF Virus

The parental virus isolate RVFV 56/74 was subjected to serial passages in Vero cells in the presence of 40 μM favipiravir. Viral titration of the culture supernatants indicated that the production of viral progeny progressively decreased, being undetectable in steps 5, 6 and 7. However, in steps 8 and 9 infectivity was recovered with normal viral titers, indicating the generation of a virus resistant to favipiravir, which was called FMH-P8 (from "Favipiravir-Mutagenized Hyperattenuated Passage 8"). The viral production of FMH-P8 virus was analyzed in the presence of different concentrations of favipiravir, obtaining a 50% reduction in viral production at a concentration of 80 UM of favipiravir. These results indicated that FMH-P8 virus was more resistant to favipiravir compared to parental virus.

Example 2. Genetic Changes in FMH-P8 Attenuated RVF Virus

Overlapping RT-PCR reactions were performed from RNA extracted from infection supernatants of attenuated RVF virus of the invention, FMH-P8, obtained in the previous example. Amplicons were produced in these reactions, covering all 3 segments of the viral genome. We proceeded to sequence these amplicons by automatic sequencing (Sanger sequencing). The deduced amino acid sequences were aligned and compared to those of the parental virus RVFV 56/74. The description of the sequences of the attenuated RVF virus of the invention FMH-P8 and the parental virus RVFV 56/74 are shown in Table 2.

TABLE 2

| Description | SEQ ID NO |
|---|---|
| FMH-P8 RVF virus L segment | 1 |
| FMH-P8 RVF virus M segment | 2 |
| FMH-P8 RVF virus S segment | 3 |
| FMH-P8 RVFV L protein | 4 |
| FMH-P8 RVFV M (poly)protein | 5 |
| FMH-P8 RVFV NSs protein | 6 |
| FMH-P8 RVFV N protein | 7 |
| RVFV 56/74 L segment | 44 |
| RVFV 56/74 M segment | 45 |
| RVFV 56/74 S segment | 46 |
| RVFV 56/74 L protein | 47 |
| RVFV 56/74 M poly(protein) | 48 |
| RVFV 56/74 NSs protein | 49 |
| RVFV 56/74 N protein | 50 |

Comparing the sequences of the attenuated RVF virus of the invention FMH-P8 with that of the parental virus RVFV 56/74, a total of 47 nucleotide changes have been found that result in 24 amino acid changes. In particular, in the L segment, which encodes the viral polymerase, the target of favipiravir, 17 nucleotide changes were identified, with 7 amino acid changes. The distribution of all changes found in the 3 genomic segments is shown in Table 3.

TABLE 3

| RNA segment | Protein/ region | Change in nucleotide(s) position | Change in nucleotide(s) (codon) | Amino acid position | Amino acid substitution |
|---|---|---|---|---|---|
| L | N-TERM | 198 | C→T | 60 | (Gly) - |
|  | 5' end | 317 | ATG→ACG | 100 | Met→Thr |
|  |  | 396 | C→T | 126 | (Phe) - |
|  |  | 1120 | C→T | 368 | (Leu) - |
|  |  | 1141 | CAC→TAC | 375 | His→Tyr |
|  | RdRp | 2757 | C→T | 913 | (His) - |
|  | nucleus | 2788 | GGT→AGT | 924 | Gly→Ser |
|  |  | 3166 | ATT→GTT | 1050 | Ile→Val |
|  | C-TERM | 3925 | GCC→ACC | 1303 | Ala→Thr |
|  | 3' end | 4110 | G→A | 1364 | (Leu) - |
|  |  | 4903 | CTC→TTC | 1629 | Leu→Phe |
|  |  | 4992 | G→A | 1658 | (Lys) - |
|  |  | 5025 | G→A | 1669 | (Val) - |
|  |  | 5178 | G→A | 1720 | (Lys) - |
|  |  | 5193 | A→G | 1725 | (Lys) - |
|  |  | 5229 | C→T | 1737 | (Phe) - |
|  |  | 6229 | GAG→AAG | 2071 | Glu→Lys |
| Total number of changes |  | 17 |  | 7 | |
| M | NSm | 97 | AGA→AAA | 26 | Arg→Lys |
|  |  | 342 | CAC→TAC | 108 | His→Tyr |
|  |  | 372 374 | GAG→AAA | 118 | Glu→Lys |
|  | Gn | 649 (mixture) | AGA→AAA | 210 | Arg→Lys |
|  |  | 716 | CAG→CAA | 232 | (Gln) - |
|  |  | 1017 | GAT→AAT | 333 | Asp→Asn |
|  |  | 1299 | GCT→ACT | 427 | Ala→Thr |
|  |  | 1315 | GCC→GTC | 432 | Ala→Val |
|  |  | 1337 | GGT→GGA | 439 | (Gly) - |
|  |  | 1480 | GAG→GGG | 487 | Glu→Gly |
|  |  | 1638 | CAC→TAC | 540 | His→Tyr |
|  |  | 1742 | CTG→CTA | 574 | (Leu) - |
|  |  | 1764 | GCT→ACT | 582 | Ala→Thr |
|  |  | 1779 | GTT→ATT | 587 | Val→Ile |
|  | Gc | 2324 | AGC→AGT | 768 | (Ser) - |
|  |  | 2869 | GCA→GTA | 950 | Ala→Val |
|  |  | 3288 | GTA→ATA | 1090 | Val→Ile |
|  |  | 3359 | ACC→ACT | 1113 | (Thr) - |
|  |  | 3367 | GCT→GTT | 1116 | Ala→Val |
|  |  | 3565 | AGA→AAA | 1182 | Arg→Lys |
|  | 3'NCR | 3821 | A→G | — | — |
|  |  | 3823 | T→A | — | — |
| Total number of changes |  | 23 |  | 15 | |
| S | NSs | 124 | AGG→AGA | 30 | (Arg) - |
|  |  | 188 | GTT→ATT | 52 | Val→Ile |
|  |  | 279 | CCA→CTA | 82 | Pro→Leu |
|  |  | 598 | GAG→GAA | 188 | (Glu) - |
|  | Intergenic region | 887 | C→T | — | — |
|  | N | 952 | GTC→GTT | 234 | (Val) - |
|  |  | 1645 | AAC→AAT | 3 | (Asn) - |
| Total number of changes |  | 7 |  | 2 | |
| TOTAL |  | 47 |  | 24 | |

Amino acids between parentheses followed by a dash indicate that there is no amino acid substitution in the FMH-P8 RVF virus relative to the parental RVFV 56/74 virus.

Nucleotide changes found in segment S led to only 2 amino acid substitutions, both in the NSs protein: Val52Ile and Pro82Leu. Pro82 belongs to the second Pro-X-X-Pro motif involved in the nuclear localization of the NSs protein and the activation of Interferon-β (IFN-β). The N nucleoprotein was the only FMH-P8 virus protein that showed an amino acid sequence identical to that of the parental virus, with only two (silent) nucleotide substitutions.

In the sequence corresponding to the M segment of the FMH-P8 virus, a total of 15 amino acid substitutions were identified, three in the NSm protein (Arg26Lys, His108Tyr, Glu118Lys), eight in the Gn protein (Arg210Lys-mix-, Asp333Asn, Ala427Thr, Ala432Val, Glu487Gly, His540Lys, Ala582Thr, Val587Ile) and four in the Gc protein (Ala950Val, Val1090Ile, Ala1116Val and Arg1182Lys). The Arg1182Gly change in Gc has been identified as an attenuation marker for MP-12 virus (Ikegami et al., 2015).

Seven amino acid substitutions were identified in the FMH-P8 virus L protein, distributed throughout the sequence. Two changes were located in the N-terminal region of the L protein (Met100Thr and His375Tyr); two in the C-terminal region (Leu1629Phe and Glu2071Lys), the three remaining substitutions (Gly924Ser, Ile1050Val and Ala1303Thr) in the central region of the protein. Positions 924 and 1050 are located within the RdRp core, where the conserved catalytic motifs A to H of the polymerase reside.

Since viral RNA polymerase is known to be a target of favipiravir, the conservation level of mutated residues of FMH-P8 RVF virus located within the catalytic nucleus of RdRp has been evaluated. The L-protein sequences corresponding to 60 different strains of RVFV have been compared and several virus species belonging to the genus phlebovirus have also been included (Table 4). Residues Gly924 and Ala1303 were found to be extremely conserved in all viruses included in the alignment. Position 1050 showed only conservative changes, mainly showing isoleucine (such as parental virus 56/74) or valine (such as attenuated FMH-P8 RVFV), while the other substituted positions were conserved among the RVFV strains but varied in other viruses of the phlebovirus genus.

TABLE 4

| Virus | Amino Acid Positions in RVFV Isolates | | | | | | |
|---|---|---|---|---|---|---|---|
| | 100 | 375 | 924 | 1050 | 1303 | 1629 | 2071 |
| Nucleotide | | | 2788 | 3166 | 3925 | | |
| RVFV 56/74 | Met | His | Gly | Ile | Ala | Leu | Glu |
| FMH-P8 RVFV | Thr | Tyr | Ser | Val | Thr | Phe | Lys |
| RVFV (60) | — | — | — | — | — | — | — |
| Phlebovirus Bujaru (2) | Ile/Val | Tyr | — | Val | — | Ile/Leu | Thr/Ser |
| Phlebovirus Candiru (2) | Val | Asp/Glu | — | —/Val | — | Ile/Val | Asp/Arg |
| Phlebovirus Frijoles (1) | Ser | Asn | — | — | — | — | Arg |
| Phlebovirus Punta Toro (3) | Ile/Val | Tyr | — | Val | — | Ile/Ser | Asn/Asp/Ser |
| Phlebovirus Salehabad (2) | Val | Asp | — | —/Val | — | Glu | Ala/Thr |
| Phlebovirus Naples Fly Fever (3) | Val* | —/Asn | — | —/Val | — | Glu | Ser |
| Phlebovirus SFTS (2) | Ile | Val | — | Ser | — | — | Asp |
| Phlebovirus Uukuniemi (2) | Leu/Ile | Asp/Val | — | Thr | —/Thr | Glu/Ser | Ser/Thr |

The amino acid residues at the L protein position of the indicated viruses are shown. The dash means that the residue matches that of the parental virus RVFV 56/74.

Example 3. Infectivity of FMH-P8 Attenuated RVF Virus in Vero and C6/36 Cells The kinetics and total yield of FMH-P8 attenuated RVF virus were analyzed. For comparison purposes, parental virus RVFV 56/74 was also tested before and after spread over 8 passes, in the absence of favipiravir. As mosquitoes play an important role in the natural transmission cycle of RVFV, infections were also carried out in the C6/36 cell line derived from *Aedes albopictus* (ATCC CRL1660).

Infections performed on Vero cells showed similar growth curves for all three viruses (FIG. 1A). Titration of supernatants collected at different times post infection in several independent experiments showed only small differences between the three viruses. The growth pattern of parental virus RVFV 56/74 after 8 passes showed no differences with parental virus RVFV 56/74 prior to such passes. FMH-P8 RVFV grew a little faster and with higher viral production yields 3-4 days post infection, although the differences were not statistically significant (multiple t-test).

Both viral growth and final yield in C6/36 mosquito cells were clearly affected by FMH-P8 RVF virus (FIG. 1B). Infected C6/36 mosquito cells remain viable for longer in cell culture than Vero cells and the analysis was extended up to 9 days. In the insect cells, the growth of the FMH-P8 RVF virus was significantly delayed, with viral titers of $10^4$ pfu/ml to 2-4 days post infection, at least 3 log units lower than those produced by the control viruses. The total virus yields at the last points analyzed (7-9 days post infection), although they reached a titer of $10^7$ pfu/mL, were below those reached by the parental virus RVFV 56/74 (>$10^8$ pfu/mL). No significant changes were found for the parental virus RVFV 56/74 after 8 passes with respect to the parental virus RVFV 56/74 before said passes.

The phenotype of the Vero cell plate in the presence of the FMH-P8 RVF virus differed substantially from the parental virus, producing plates smaller than those produced by the RVFV 56/74 parental virus before or after 8 passes (FIG. 1C).

Example 4. FMH-P8 Attenuated RVFV Infectivity in IFNAR Immunodeficient Mice$^{-/-}$ To check in vivo the attenuation of the FMH-P8 RVF virus, an infection experiment was performed using the A129 mouse strain (IFNAR$^{-/-}$). A129 mice cannot cope with acute viral infection and are highly susceptible to RVFV infection and offer a highly sensitive assessment of FMH-P8 RVFV attenuation.

Figure 2:
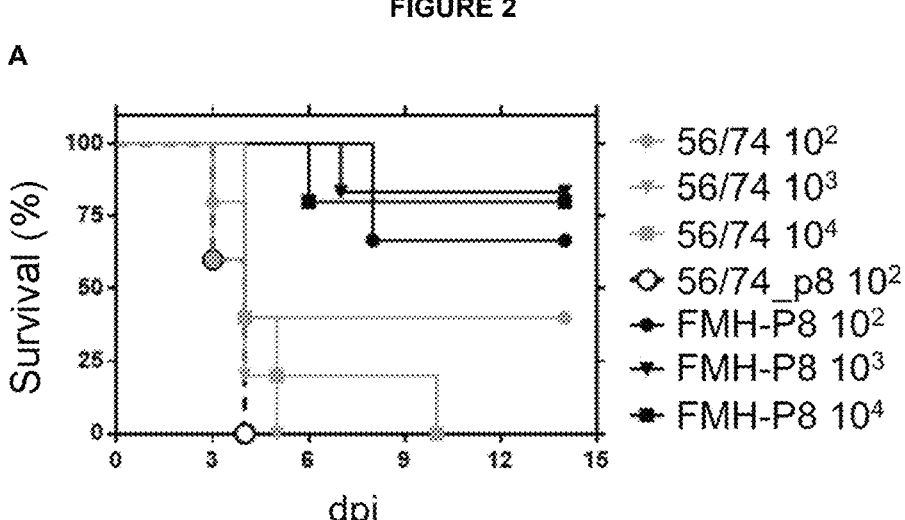
FIG. 2. In vivo infectivity analysis of the FMH-P8 RVF virus in A129 mice (IFNAR−/−). Male mice 5-6 months of age were inoculated with the indicated doses of the FMH-P8 RVF virus, the parental RVF virus 56/74 after 8 passes (56/74 p8) and before said passes (56/74). Animals were monitored daily for 14 days. Survival rates (A) and body weight change (B) in challenged mice at different doses. C. Detection of nucleoprotein-specific antibodies by indirect ELISA assay. 1, control sample; 2, sample 56/74 $10^2$; 3, sample FMH-P8 $10^2$; 4, sample FMH-P8 $10^3$; 5, sample FMH-P8 $10^4$. dpi represents days post infection.
Figure 2:
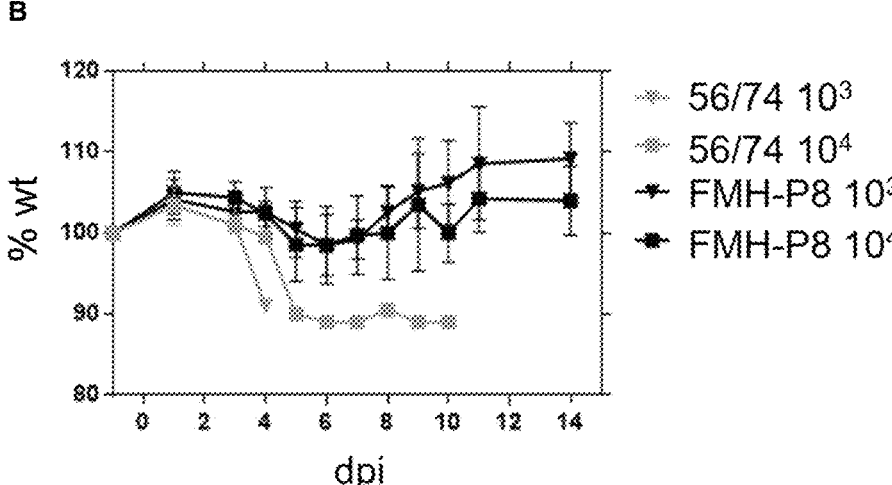
Figure 2:
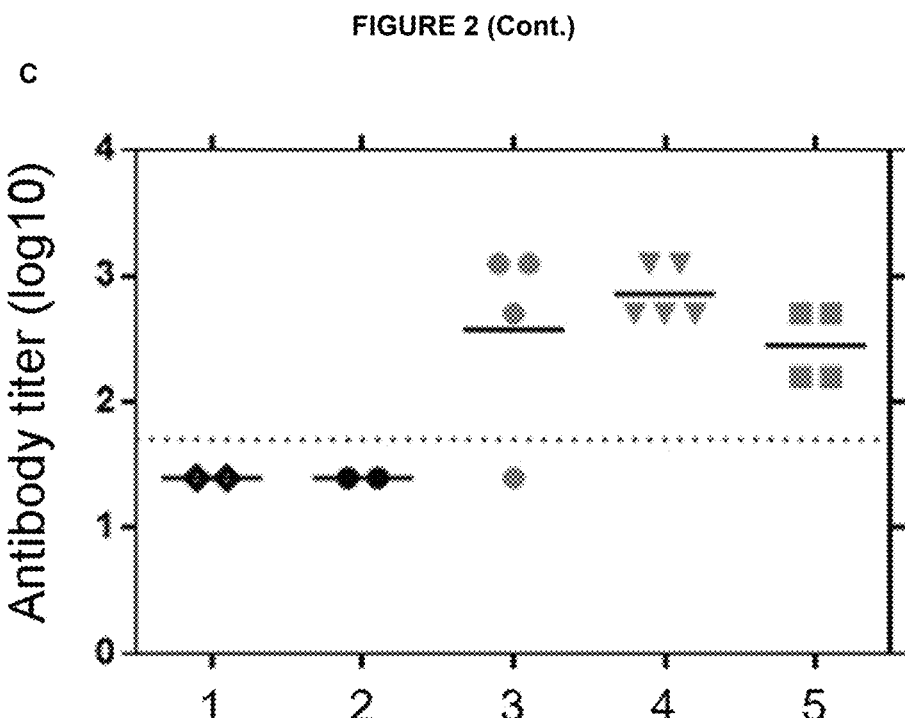

Different doses of virus were inoculated intraperitoneally to groups of 5-6 mice and were monitored daily for 2 weeks to check the development of signs of disease and survival (FIG. 2A). After 8 passes the parental virus RVFV 56/74 caused 100% mortality 4 days post inoculation with $10^2$ pfu, while mice inoculated with the same dose of the parental virus RVFV 56/74 before such passes showed a survival rate of 40% ($\frac{2}{5}$). Although these data suggest increased virulence of the parental virus RVFV 56/74 after 8 passes, the results were not statistically significant. Higher doses of the parental virus RVFV 56/74 caused death of inoculated animals in the first 4 days post infection: 100% in those inoculated with $10^3$ pfu; 90% in those inoculated with $10^4$ pfu, with no survivors at day 10.

In contrast, animals inoculated with the FMH-P8 RVF virus showed survival rates above 70% even with a high challenge dose ($10^4$ pfu), with a significant number of survivors at the end of the experiment: $\frac{5}{6}$ (83%) in those who received $10^3$ pfu and $\frac{4}{5}$ (80%) in those inoculated with $10^4$ pfu. No signs of disease were seen in any of these animals, except for slight weight loss on days 3-5 post infection (FIG. 2B).

Serum samples collected on day 14 (end of experiment) were analyzed by ELISA for the presence of N-nucleoprotein (anti-N) antibodies in survivors, indicative of viral replication (FIG. 2C). In some animals within the groups that received the lowest viral dose, $10^2$ pfu, anti-N antibodies were undetectable, probably reflecting low or zero levels of viral replication (2/2 in mice inoculated with RVFV 56/74 virus; 1/4 in mice inoculated with FMH-P8 virus). All animals inoculated with $10^3$ and $10^4$ pfu of FMH-P8 RVF virus, as well as three of the group inoculated with $10^2$ pfu of FMH-P8 RVF virus developed specific anti-N antibodies. The titers of anti-N antibodies showed no significant differences (ordinary one-way ANOVA) within the groups inoculated with FMH-P8 RVF virus, regardless of the dose received.

Figure 3:
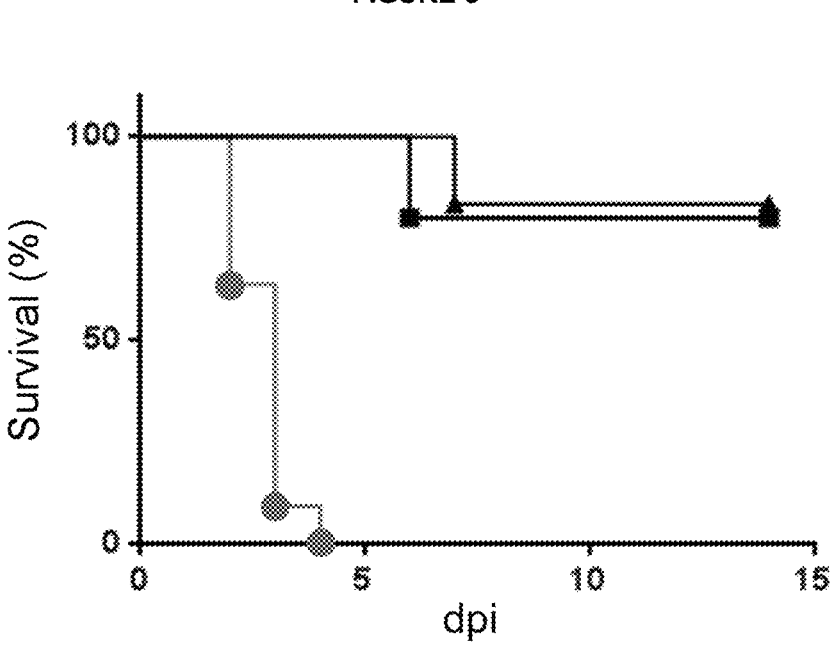
FIG. 3. Comparison of survival rates of A129 mice (IFNAR−/−) inoculated with FMH-P8 RVF virus and MP-12 RVF virus (Ikegami et al., 2015). Mice were inoculated with FMH-P8 RVF virus doses $10^3$ pfu (triangles) and $10^4$ pfu (squares) and MP-12 RVF virus (doses $10^4$ pfu, circles). dpi represents days post infection.

An in vivo infectivity assay was performed in A129 mice with FMH-P8 RVF virus and with MP-12 live attenuated vaccine (Ikegami et al., 2015). The MP-12 vaccine administered in IFNAR–/– mice at the same dose ($10^4$ cfu) causes the death of 100% of the mice of the strain within 5 days (FIG. 3). These results demonstrate the high vaccine potential of the FMH-P8 RVF virus.

Figure 4:
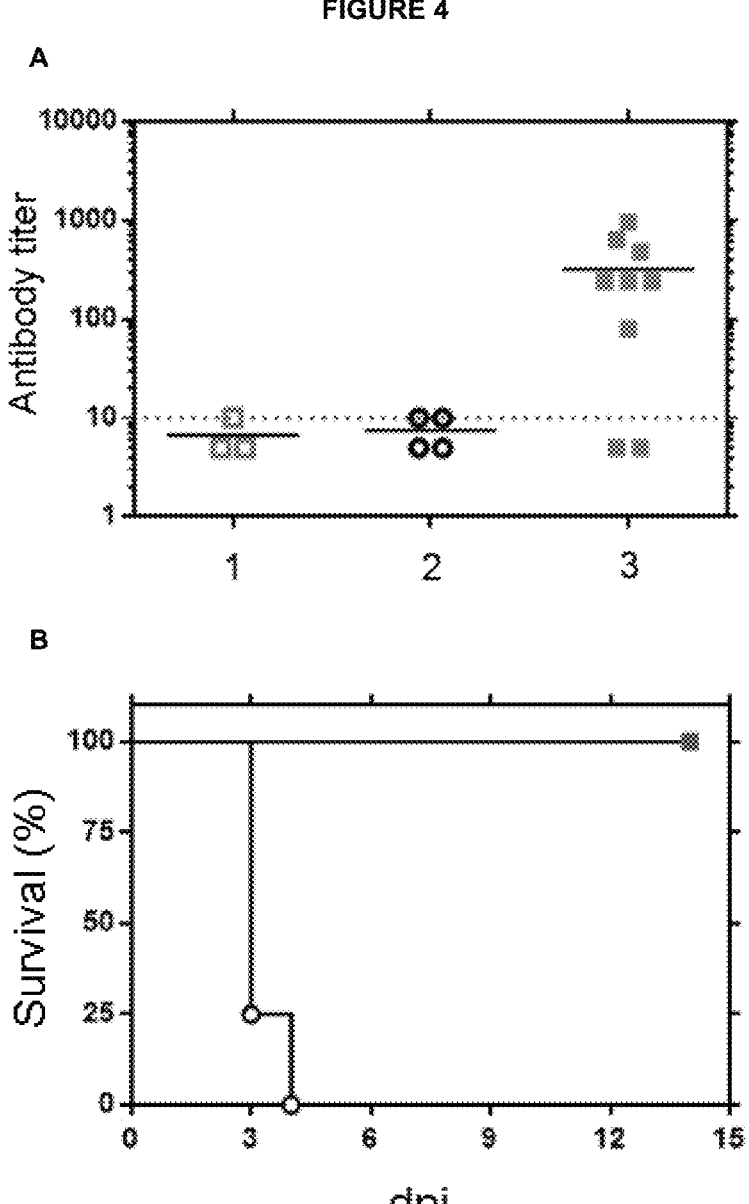
FIG. 4. Analysis of the immunogenicity and efficacy of FMH-P8 attenuated virus to a lethal challenge with RVF virus 56/74. Wild 11-month-old 129Sv/Ev mice (n=9) were inoculated intraperitoneally with $10^4$ pfu FMH-P8 RVFV. A group of control mice was inoculated (n=4). A. Microneutralization test. Serum samples were taken on day 24 (pre-challenge samples) and assayed for neutralizing antibodies. Serums were analyzed in dilutions in base 2 from 1/10 to 1/1280. The titer is expressed as the last dilution of serum that results in a reduction of cytopathic effect (CPE) in 50% of wells. First dilution tested: 1/10 (cut); "neg" samples (CPE in all wells in the first dilution analyzed) arbitrarily represented as 1/5. 1, "neg" samples; 2, samples with control mice inoculation; 3, FMH-P8 samples. B. Survival of 129Sv/Ev mice in challenge with FMH-P8 RVFV (squares) and with control mice inoculation (circles). C. Morbidity after exposure in vaccinated mice. D, S and H represent the clinical status of each mouse (D: dead, S: sick, H: healthy). Lower panel C, mice in challenge with FMH-P8 RVFV; upper panel C, control mice inoculation. D. Detection of anti-nucleoprotein antibodies by ELISA. Each symbol corresponds to an individual animal, except for the "neg" samples (groups of pre-immune sera). The titer is represented as log 10 of the last dilution of serum providing an optical density (OD) greater than 0.250 (control "neg" samples giving readings of 0.07 as an average; blank wells mean 0.04). 1, "neg" samples; 2, control group samples; 3, FMH-P8 samples; 4, post-challenge FMH-P8 samples. Serums were analyzed in dilutions in base 3 from 1/50 to 1/109350. First dilution analyzed: 1/50 (titre 1.7 (cut-off value); samples "neg" 1/25 (log 1.4)). dpi represents days post infection.
Figure 4:
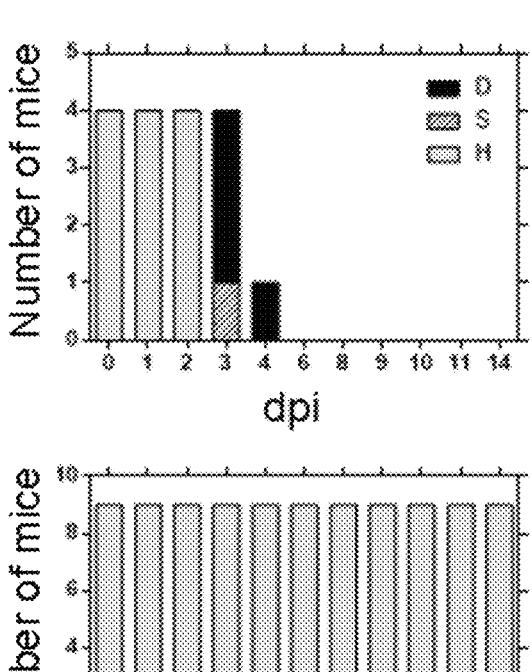
Figure 4:
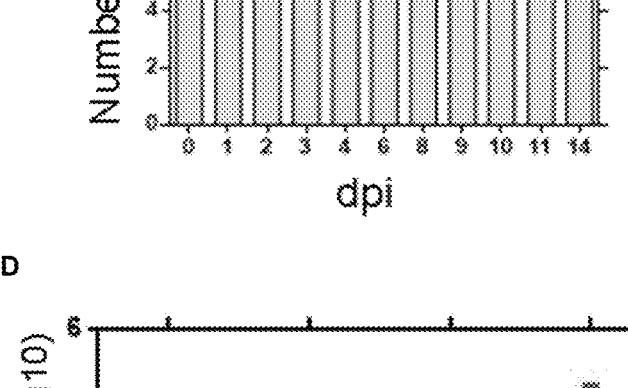

Example 5. Immunogenicity and Efficacy of FMH-P8 Attenuated RVF Virus in Immunocompetent Mice FMH-P8 attenuated RVF virus was assayed in immunocompetent mice. To do this, wild 129Sv/Ev mice were inoculated intraperitoneally with $10^4$ pfu of the FMH-P8 RVF virus, and 4 weeks later were challenged with a lethal dose ($10^4$ pfu) of the parental RVF virus 56/74. After inoculation with FMH-P8 RVF virus, mice showed no signs of disease, not even significant weight variations. In serum samples collected 24 days after inoculation (samples prior to lethal challenge with parental virus RVFV 56/74), seven out of nine mice showed a strong neutralizing antibody response (FIG. 4A). N-nucleoprotein antibodies were detected in all these samples by indirect ELISA, including two samples that were negative in the neutralization assay, although their anti-N antibody titers were slightly lower (FIG. 4D). This indicates that the FMH-P8 RVF virus replicated in all inoculated mice at least to an extent sufficient to elicit an immune response. When mice were subjected to a lethal challenge with the virulent strain RVFV 56/74, 100% of the mice survived to the end of the experiment (FIG. 4B, FIG. 4C) without apparent clinical manifestation, including those in which no neutralizing antibody titers had been detected. In contrast, all mice in the control group became ill and died on day 4 (FIG. 4B, FIG. 4C).

Anti-N antibody titers increased following lethal challenge with parental virus RVFV 56/74 (FIG. 4D), indicating a booster effect of attenuated virus FMH-P8 RVFV in mice. Taken together, these results show that, despite its highly attenuated phenotype, the FMH-P8 RVF virus could be replicated in immunocompetent 129Sv/Ev mice at levels that allow for the induction of protective immune responses, even when no neutralizing antibodies are detected.

Example 6. Immunogenicity of FMH-P8 Attenuated RVF Virus in Sheep

Figure 5:
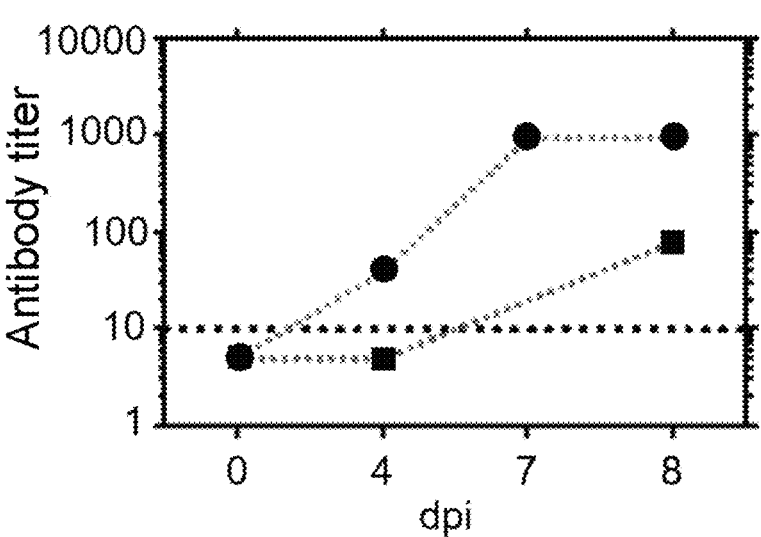
FIG. 5. Clinical signs in sheep inoculated with FMH-P8 RVF virus and parental virus 56/74. Rectal temperature (A), liver enzymes (B) and neutralizing antibody production (C) are compared in inoculated sheep with $10^7$ pfu of FMH-P8 RVF virus (squares, n=2) and parental RVF virus 56/74 (circles, n=3).

The attenuated FMH-P8 RVF virus was inoculated into ewes to assess its attenuation and immunogenicity in a natural host of the RVF virus. Animals received an elevated dose of $10^7$ pfu of the attenuated FMH-P8 RVF virus and clinical signs were monitored daily and daily sampling was performed. Fever was not recorded in any of the animals on the days immediately following inoculation of the attenuated FMH-P8 RVF virus, and liver enzyme titration did not indicate alterations in sheep inoculated with FMH-P8 unlike control sheep that had been inoculated with parental virus 56/74 which showed a spike in fever from day 2 post infection. Even in the absence of clinical signs, seroconversion was observed, reaching a significant titer of neutralizing antibodies at day 8 post-inoculation. Although the neutralizing antibody titer obtained with RVFV is lower than that obtained with parental virus 56/74, it is concluded that said neutralizing antibody titer is significant and sufficient to provide protection to sheep. The results of this example also demonstrate the safety provided by the attenuated FMH-P8 RVF virus and support the vaccine viability of the FMH-P8 RVF virus (FIG. 5).

Example 7. Assay in Mice Inoculated with Variants of the RVF Virus and after Challenge with a Lethal Dose of the ZH548 Strain of the RVF Virus Wild mice 129 were inoculated with variants of the RVF virus and subsequently challenged with a lethal dose of the wild strain ZH548 of the RVF virus (a virulent strain).

Four groups of mice were inoculated with either the ZH548 strain of the RVF virus or different variants of the ZH548 strain, as indicated below.

Mice of group C1 were inoculated with strain ZH548 of the RVF virus, a wild virulent control.

Mice of group G1 were inoculated with the ZH548_ΔNSs:gfp variant of the RVF virus, an attenuated control with the region of the RNA encoding the deleted NSs protein.

Mice of group A2 were inoculated with the variant ZH548_L[Gly924Ser]_L[Ala1303Thr]_NSs [Pro82Leu] of the RVF virus, a variant with Gly924Ser and Ala1303Thr substitutions in the protein encoded by the RdRp gene of the L segment of the viral RNA and with Pro82Leu substitution in the protein encoded by the NSs gene of the S segment of the viral RNA.

Mice of group were B3 inoculated with variant ZH548_L [Gly924Ser]_L[Ala1303Thr], a variant with Gly924Ser and Ala1303Thr substitutions in the protein encoded by the RdRp gene of the L segment of the viral RNA.

Table 5 shows the results of viraemia, survival and seroconversion after inoculation of the different variants and after challenge with a lethal dose of the ZH548 strain of the RVF virus.

TABLE 5

| Group | After inoculation of the ZH548 strain or variant of the RVF virus | | | After challenge | |
| | % survival (15 dpi) | Viraemia (day 3) | Neutralizing antibodies (12 dpi) | % survival (15 dpi) | Viraemia (day 3) |
|---|---|---|---|---|---|
| C1 | 0 | 25.10 | nd | — | — |
| G1 | 100 | NEG | 1.98 | 100 | NEG |
| A2 | 100 | NEG | 2.60* | 100 | NEG |
| B3 | 100 | NEG | 3.27 | 100 | NEG** |

The viraemia values and neutralizing antibody titers correspond to the group means (n=6, except G1 n=5).

dpi: days post-infection.

viraemia: Cq value (quantification cycle) by RT-qPCR technique (reverse transcriptase quantitative polymerase chain reaction).

NEG: Values below the sensitivity level of the test (Cq=37).

Neutralizing antibody titer=PRNT80 (log 10). In group C1, no survivors were recorded at that time post-infection.

In groups G1 and B3 all animals were positive, while in group A2 there were 2 animals (2/6) with values below the limit of detection of the test (dilution 1/50; log 10=1.70). * The indicated mean excludes these 2 negative values.

** After the challenge, in group B3, viraemia was detected at day 3 in a single animal (1/6), with a Cq=33.69.

The results of this example demonstrate a very clear virus attenuation effect of three amino acid substitutions in the ZH548 strain of the RVF virus: the Pro82Leu substitution in the protein encoded by the NSs gene of the S segment of the viral RNA and the Gly924Ser and Ala1303Thr substitutions in the RdRp protein of the L segment of the viral RNA.

The sequences of strain ZH548 are accessible through GenBank with the access codes DQ375403 (segment L), DQ380206 (segment M) and DQ380151 (segment S). The description of the sequences of strain ZH548 is shown in Table 6.

TABLE 6

| Description | SEQ ID NO |
|---|---|
| ZH548 RVF virus L segment | 51 |
| ZH548 RVF virus M segment | 52 |
| ZH548 RVF virus S segment | 53 |
| ZH548 RVFV L protein | 54 |
| ZH548 RVFV M (poly)protein | 55 |
| ZH548 RVFV NSs protein | 56 |
| ZH548 RVFV N protein | 57 |

Example 8. Assay in Sheep Inoculated with Variants of the RVF Virus and after Challenge with a Lethal Dose of the ZH548 Strain of the RVF Virus A group of two sheep were inoculated with a lethal dose of the RVF virus strain ZH548.

A group of four sheep were inoculated with variant ZH548_L[Gly924Ser]_L[Ala1303Thr]_NSs[Pro82Leu] of the RVF virus (variant with Gly924Ser and Ala1303Thr substitutions in the protein encoded by the RdRp gene of viral RNA segment L and with Pro82Leu substitution in the protein encoded by the NSs gene of viral RNA segment S. Two sheep in this group were challenged with the ZH548 strain of the RVF virus three weeks later. The other two sheep in the group were sacrificed in a short time to compare the possible lesions with the control sheep given the lethal dose of the ZH548 strain of the RVF virus.

Ewes inoculated with the RVF virus strain ZH548_L[G924S/A1303T]_NSs[P82L] produced neutralizing antibodies and showed no lesions compared to those inoculated with the control virus. It was also not possible to detect infectious virus in the blood of immunized sheep compared to control.

Results of this example demonstrate the attenuation conferred by the three substitutions L[Gly924Ser], L[Ala1303Thr] and NSs[P82L]. They also confirm that said variant has the ability to induce an immune response capable of protecting sheep from a challenge with the wild strain ZH548.

SEQUENCE LISTING FREE TEXT

The sequence listing free text is reproduced in Table 7.

TABLE 7

| SEQ ID NO | Position | Free text |
|---|---|---|
| 1 | | FMH-P8 RVF virus L segment |
| | 19-6297 | FMH-P8 RVF virus L-segment open reading frame |
| 2 | | FMH-P8 RVF virus M segment |
| | 21-3614 | FMH-P8 RFV virus gene encoding M (poly)protein |
| 3 | | FMH-P8 RVF virus S segment |
| | 35-832 | FMH-P8 RVF virus gene encoding NSs protein |
| | 916-1653 | FMH-P8 RVFV gene encoding N protein (complementary) |
| 4 | | FMH-P8 RVFV L protein |
| | 100 | Thr |
| | 375 | Tyr |
| | 924 | Ser |
| | 1050 | Val |
| | 1303 | Thr |
| | 1629 | Phe |
| | 2071 | Lys |
| 5 | | FMH-P8 RVFV M (poly)protein |
| | 26 | Lys |
| | 108 | Tyr |
| | 118 | Lys |
| | 210 | Lys |
| | 333 | Asn |
| | 427 | Thr |
| | 432 | Val |
| | 487 | Gly |
| | 540 | Tyr |
| | 582 | Thr |
| | 587 | Ile |
| | 950 | Val |
| | 1090 | Ile |
| | 1116 | Val |
| | 1182 | Lys |
| 6 | | FMH-P8 RVFV NSs protein |
| | 52 | Ile |
| | 82 | Leu |
| 7 | | FMH-P8 RVFV N protein |
| 8 | | 5' end L segment primer |

TABLE 7-continued

| SEQ ID NO | Position | Free text |
|---|---|---|
| 9 | | 716F primer |
| 10 | | L-F segment 1028ag primer |
| 11 | | L-R 2300g primer |
| 12 | | RdRp central-F primer |
| 13 | | L-F segment primer |
| 14 | | L-R segment primer |
| 15 | | Central-R RdRp primer |
| 16 | | 3817 F primer |
| 17 | | 4553 F primer |
| 18 | | 5455 F primer |
| 19 | | R 5583 primer |
| 20 | | Q3'25nts primer |
| 21 | | L-segment end q3'R primer |
| 22 | | (−2)Rtsm1 primer |
| 23 | | MRV1ag primer |
| 24 | | RTsm2 primer |
| 25 | | Sm2 primer |
| 26 | | Sm3 primer |
| 27 | | Sm4 primer |
| 28 | | EM-RVFV-R primer |
| 29 | | EM-RVFV-F primer |
| 30 | | NS0g primer |
| 31 | | NS2g primer |
| 32 | | R-S primer |
| 33 | | F-S primer |
| 34 | | NScag primer |
| 35 | | SS1 primer |
| 36 | | RTss1 primer |
| 37 | | NP0ag primer |
| 38 | | LsegcARN primer |
| 39 | | LsegvARN primer |
| 40 | | MsegcARN primer |
| 41 | | MsegvARN primer |
| 42 | | SsegcARN primer |
| 43 | | SsegvARN primer |
| 44 | | RVFV 56/74 L segment |
| | 19-6297 | RVFV 56/74 L segment open reading frame |
| 45 | | RVFV 56/74 M segment |
| | 21-3614 | RVFV 56/74 gene encoding M (poly)protein |
| 46 | | RVFV 56/74 S segment |
| | 35-832 | RVFV 56/74 gene encoding NSs protein |
| | 916 . . . 1653 | RVF virus gene encoding N protein 56/74 |
| 47 | | RVFV 56/74 L protein |
| 48 | | RVFV 56/74 M poly(protein) |
| 49 | | RVFV 56/74 NSs protein |
| 50 | | RVFV 56/74 N protein |
| 51 | | ZH548 RVF virus L segment |
| | 19-6297 | ZH548 RVF virus L-segment open reading frame |
| 52 | | ZH548 RVF virus M segment |
| | 21-3614 | ZH548 RFV virus gene encoding M (poly)protein |
| 53 | | ZH548 RVF virus S segment |
| | 35-832 | ZH548 RVF virus gene encoding NSs protein |
| | 915 . . . 1652 | ZH548 RVF virus gene encoding N protein |
| 54 | | ZH548 RVFV L protein |
| 55 | | ZH548 RVFV M (poly)protein |
| 56 | | ZH548 RVFV NSs protein |
| 57 | | ZH548 RVFV N protein |

REFERENCES

Borrego et al. (2019). Lethal Mutagenesis of Rift Valley Fever Virus Induced by Favipiravir. *Antimicrob Agents Chemother,* 63 (8), PII: e00669-19.

Busquets et al. (2010). Experimental infection of young adult European breed sheep with Rift Valley fever virus field isolates. *Vector Borne Zoonotic Dis,* 10 (7), 689-696.

Ikegami et al. (2015). Rift Valley Fever Virus MP-12 Vaccine Is Fully Attenuated by a Combination of Partial Attenuations in the S, M, and L Segments. *J Virol,* 89 (14), 7262-7276.

The invention claimed is:

1. An attenuated variant of the Rift Valley Fever virus (RVFV), wherein the RNA-dependent RNA polymerase (RdRp) protein encoded by the L segment of the RNA of said variant comprises the substitutions:

the amino acid at position 924 is serine (L[Gly924Ser]);

the amino acid at position 1303 is threonine (L[Ala1303Thr]);

wherein the sequence SEQ ID NO: 47 of wild strain 56/74 of the RVF virus or the sequence SEQ ID NO: 54 of the wild type ZH548 strain of the RVF virus, are the reference sequences for the numbering of the amino acids of said protein;

and the non-structural (NSs) protein encoded by the S segment of the RNA of said variant comprises the substitution:

the amino acid at position 82 is leucine (NSs[Pro82Leu]);

wherein the sequence SEQ ID NO: 49 of wild strain 56/74 of the RVF virus or the sequence SEQ ID NO: 56 of the wild type ZH548 strain of the RVF virus, are the reference sequences for the numbering of the amino acids of said protein.

2. The RVFV variant according to claim 1 wherein, further, in the RdRp protein encoded by the L segment of the RNA of said variant:

the amino acid at position 100 is threonine (L[Met100Thr]);

the amino acid at position 375 is tyrosine (L[His375Tyr]);

the amino acid at position 1050 is valine (L[Ile1050Val]);

the amino acid at position 1629 is phenylalanine (L[Leu1629Phe]); and the amino acid at position 2071 is lysine (L[Glu2071Lys]);

wherein the sequence SEQ ID NO: 47 of wild strain 56/74 of the RVF virus or the sequence SEQ ID NO: 54 of the wild type ZH548 strain of the RVF virus, are the reference sequences for the numbering of the amino acids of said protein;

in the amino acid sequence encoded by the M segment of the RNA of said variant:

the amino acid at position 26 is lysine (M[Arg26Lys]);

the amino acid at position 108 is tyrosine (M[His108Tyr]);

the amino acid at position 118 is lysine (M[Glu118Lys]);

the amino acid at position 210 is lysine (M[Arg210Lys]);

the amino acid at position 333 is asparagine (M[Asp333Asn]);

the amino acid at position 427 is threonine (M[Ala427Thr]);

the amino acid at position 432 is valine (M[Ala432Val]);

the amino acid at position 487 is glycine (M[Glu487Gly]);

the amino acid at position 540 is tyrosine (M[His540Tyr]);

the amino acid at position 582 is threonine (M[Ala582Thr]);

the amino acid at position 587 is isoleucine (M[Val587Ile]);

the amino acid at position 950 is valine (M[Ala950Val]);

the amino acid at position 1090 is isoleucine (M[Val1090Ile]);

the amino acid at position 1116 is valine (M[Ala1116Val]); and the amino acid at position 1182 is lysine (M[Arg1182Lys]);

wherein the sequence SEQ ID NO: 48 of wild strain 56/74 of the RVF virus or the sequence SEQ ID NO: 55 of the wild strain ZH548 of the RVF virus, are the reference sequences for amino acid numbering of said amino acid sequence encoded by the M segment of the RNA of said variant;

in the NSs protein encoded by the S segment of the RNA of said variant:

the amino acid at position 52 is isoleucine (NSs [Val52Ile]);

wherein the sequence SEQ ID NO: 49 of wild strain 56/74 of the RVF virus or the sequence SEQ ID NO: 56 of the wild type ZH548 strain of the RVF virus, are the reference sequences for the numbering of the amino acids of said protein.

3. The RVFV variant according to claim 1, wherein the amino acid sequence encoded by the L segment of the RNA of said variant is SEQ ID NO: 4; the amino acid sequence encoded by the M segment of the RNA of said variant is SEQ ID NO: 5; the NSs protein consists of the sequence SEQ ID NO: 6; and the N protein consists of the sequence SEQ ID NO: 7.

4. The RVFV variant according to claim 1, containing an RNA encoding said variant, wherein the L segment of said RNA consists of the sequence SEQ ID NO: 1; and the M segment of said RNA consists of the sequence SEQ ID NO: 2; and the S segment of said RNA consists of the sequence SEQ ID NO: 3.

5. A pharmaceutical or veterinary composition comprising the RVFV variant according to claim 1, together with at least one pharmaceutically acceptable excipient or an excipient for veterinary use.

6. A method of preventing Rift Valley fever in animals, said method comprising administering to the animals an effective amount of the RVFV variant according to claim 1.

7. The method of claim 6, wherein the route of administration of the RVFV variant is subcutaneous, intravenous or intramuscular.

8. The method of claim 6, wherein said animals are ruminants.

9. The method of claim 8, wherein said ruminants are selected from: cows, sheep, goats, camels and buffalo.

10. The method of claim 6, wherein said animals are humans.

11. A Rift Valley Fever vaccine comprising the RVFV variant of claim 1.

12. The vaccine according to claim 11, further comprising at least one pharmaceutically acceptable excipient or an excipient for veterinary use.

* * * * *

SEQUENCE LISTING

<160> NUMBER OF SEQ ID NOS: 57

<210> SEQ ID NO 1
<211> LENGTH: 6404
<212> TYPE: DNA
<213> ORGANISM: Artificial Sequence
<220> FEATURE:
<223> OTHER INFORMATION: FMH-P8 RVF virus L segment
<220> FEATURE:
<221> NAME/KEY: gene
<222> LOCATION: (19)..(6297)
<223> OTHER INFORMATION: FMH-P8 RVF virus L-segment open reading frame

<400> SEQUENCE: 1

```
acacaaaggc gcccaatcat ggattctata ttatcaaaac agctggttga caagactggt      60
tttgttagag tgccaatcaa gcattatgac tgtacaatgc taactctggc actcccaaca     120
tttgatgtct ccaagatggt agatagaatt accatagact tcaatttaga cgacatacaa     180
ggagcatctg aaataggttc aactttgcta ccctctatgt cgatagatgt ggaagatatg     240
gccaattttg ttcacgattt caccttTggc cacttagctg acaagactga cagactctta     300
atgcgtgagt ttcccacgat gaatgacggg tttgatcatc tgagccctga catgattatc     360
aaaactacat ctggcatgta aacatcgtt gagtttacca cctttagggg ggatgaaaga     420
ggtgcattcc aggctgccat gactaaactc gctaagtatg aggttccttg tgagaacaga     480
tctcagggca ggactgttgt tctttatgtt gttagcgcct accggcatgg tgtttggtct     540
aatttggagc tagaggactc tgaagcagag gagatggtat ataggtacag acttgccctt     600
agtgtgatgg atgagctaag gaccttgttc ccagaactgt catccacaga tgaggaacta     660
ggaaagactg agagagagtt gctagccatg gtctcctcca tccaaataaa ttggtcagtc     720
acagaatctg tgtttcctcc ctttagcaga gaaatgtttg acaggttcag atcttctcct     780
cccgattcag agtacatcac gaggatagta agcagatgcc tcataaattc tcaagagaaa     840
ctcatcaata attccttctt tgctgaaggg aatgataaag ttttgagatt ttcaaaaaac     900
gctgaggagt gttccttggc aatagagaga gctttaaatc agtatagggc agaagacaac     960
cttagggacc tcaatgacca caagtctact attcagctgc cccctggct gtcctatcac    1020 gatgccgatg gcaaagatct gtgccctctt cagggattag atgtgagagg agaccatccc    1080
atgtgcaacc tgtggagaga agtggttacc tctgcaaatt tagaggagat tgagaggatg    1140
tacgatgatg cagcggcaga acttgagttt gccctttcag gggtgaagga caggccagat    1200
gaaagaaaca gataccatag agtccatctg aatatggact cagatgatag tgtctacata    1260
gctgctttag gggttaatgg aaagaagcat aaagcagaca cattagtgca acaaatgaga    1320
gacaggagca acagccctt ctctccagat catgatgtgg atcacatatc tgaatttctc    1380
tctgcatgct ctagtgactt gtgggcaaca gatgaggacc tatacaaccc tctctcttgt    1440
gataaagagc ttagattggc agctcagaga attcatcagc catccttatc agaaaggggc    1500
ttcaatgaga ttataacaga gcactacaga tttatgggaa gtaggatagg atcatggtgc    1560
caaatggtca gtttaatagg agctgagcta tcagcttctg taaagcaaca tgttaagcct    1620
aactattttg tgattaaacg actactaggt tctgggattt tcttgctgat caagcctact    1680
tccagcaaaa gccatatatt cgtgtctttt gcaattaagc gctcttgctg ggcctttgat    1740
ctctccactt ccaggggtttt caaaccctac atagatgccg gggatctgtt agttactgac    1800
tttgtttctt acaaactaag taagcttacc aacctctgca gtgcgtttc gttaatggaa    1860 tcctccttct cattttgggc agaggcattt gggattccaa gctggaactt tgttagtgac    1920
```

```
ttgttcaggt cttcagactc tgcagcaatg gatgcctcat acatgggcaa actctctttta    1980 ttaacccttt tggaagacaa agcaacaact gaagagttac agactattgc aagatatata    2040
atcatggagg gctttgtctc gcccccagaa atcccaaaac ctcacaagat gacctctaag    2100
tttcccaagg ttctcaggtc agagctgcag gtttacttat taaactgctt atgcagaact    2160
atccagagaa tagcaggtga gcccttttatt cttaagaaga aggatgggtc tatatcctgg    2220
ggtggcatgt ttaatccttt ttcagggcgt ccactgcttg atatgcaacc actcatcagc    2280
tgttgttaca atggttactt taaaaacaaa gaagaagaga ctgagccttc ctcccttttct    2340 gggatgtata agaaaattat agaacttgag caccttagac cacagtcaga tgccttcttg    2400
ggttataaag atccagaact acctagaatg catgagttca gtgtttccta cttgaaggag    2460
gcttgcaatc atgctaagct ggtcttaagg agtctctatg gacagaattt catggagcaa    2520
atagacaacc aaattattcg agagctcagt gggttgactc tagaaagatt agccacactt    2580
aaggccacaa gcaactttaa tgagaattgg tatgtctata aggatgtggc agacaagaac    2640
tacacaaggg ataaattatt agtgaagatg tcaaaatatg cttctgaggg aaagagccta    2700
gctatccaga agtttgagga ttgcatgagg cagatagagt cacaaggatg tatgcatatt    2760
tgtttgttta agaaacaaca gcatggaagt ctgagagaga tctatgtgat gggtgcagag    2820
gaaagaattg ttcaatcggt ggtggagaca atagccaggt ctatagggaa gttctttgct    2880
tctgataccc tctgtaaccc ccccaataag gtgaaaattc ctgagacaca tggcattagg    2940
gctcggaagc aatgtaaggg gcctgtgtgg acttgtgcaa catcagatga tgcaaggaag    3000
tggaaccaag gccattttgt tacaaagttt gccctcatgc tatgtgagtt cacctctcct    3060
aagtggtggc cattgatcat taggggatgt tcaatgttta ccaggaaaag gatgatgatg    3120
aatttgaatt atcttaagat cctggatggt catcgagagc ttgatgttag agatgacttt    3180
gtgatggatc tcttcaaagc ttatcatggt gaggcagaag ttccatgggc ttttaagggt    3240
aaaacatatc tggaaaccac aacagggatg atgcagggga tattgcatta tacttcctca    3300
ttattacaca ccattcatca agaatacatc cggtccttgt cctttaaaat attcaacctg    3360
aaggttgctc ctgagatgag caaaagcctg gtttgtgaca tgatgcaagg atcagatgat    3420
agtagcatgc taatcagctt cccagctgat gacgagaagg ttctcaccag atgcaaagtg    3480
gccgcagcca tatgcttccg aatgaagaag gagctgggag tgtaccttgc catctacccc    3540
tcagagaagt ccacagcaaa cacagatttt gtgatggagt acaattctga attttatttc    3600
cacacccagc atgttagacc gacgatcagg tggattgcag catgttgcag cctgccagaa    3660
gtggaaacac tagtagcccg ccaggaagag gcctctaatc taatgacttc agttactgag    3720
gggggtgggt cattctcctt agctgcaatg attcagcaag ctcagtgcac tctccattac    3780
atgctaatgg gcatgggagt gtctgagcta ttcttagagt ataagaaggc agtgctgaag    3840
tggaatgacc ctggtctggg tttcttcctg cttgacaatc cttatgcgtg cgggttggga    3900
ggttttagat ttaatctctt caaaaccatc accagaactg atttgcagaa gctatatgct    3960
ttcttcatga agaaggttaa gggctcagct gctagggact gggcagatga ggatgttacc    4020
atcccagaaa cgtgtagcgt gagcccaggt ggcgctctaa ttcttagctc ctctctaaag    4080
tggggatcta ggaagaagtt tcagaaacta agagaccgtt tgaacatacc agagaactgg    4140
attgagctaa taaatgagaa tccagaggtg ctctatcgag ctcccagaac aggcccagaa    4200
atattgttgc gcattgcaga gaaagtccat agccctggtg ttgtgtcatc attgtcttct    4260
```

-continued

```
ggcaatgcag tctgtaaagt catggcctca gctgtatact tcttatcagc aacaattttt      4320
gaagacactg gacgccctga gttcaacttc ttagaggatt ccaagtacag cttgctacaa      4380
aagatggccg catattctgg cttttcatggt ttcaatgata tggagccaga agatatatta      4440
ttcctattcc cgaacattga ggaattagaa tcactggatt ctatagttta caacaaggga      4500
gaaatagaca tcatcccaag agttaatatc agggatgcaa cccaaaccag ggtcactatc      4560
tttaatgagc agaagaccct ccgaacatct ccagagaagt tggtgtcaga caagtggttc      4620
gggactcaga agagtaggat aggcaaaaca actttcctgg ctgaatggga gaagctaaag      4680
aaaattgtga agtggttgga agacactcca gaagcaactc tagctcacac tccactgaat      4740
aaccatattc aggttaggaa tttctttgct agaatggaaa gcaagcctag aacggttaga      4800
ataacaggag ctcctgtaaa gaagaggtca ggggttagca agatagctat ggttatccgt      4860
gacaatttct cccggatggg ccatcttaga ggtgtagaag acttcgctgg cttcactcgt      4920
agtgtgtcag ctgaaatcct caagcacttt ctgttctgca tactacaggg tccatacagt      4980
gagagctata aactacagct aatctacaga gtcctaagct cagtatcaaa cgttgagata      5040
aaggaatcgg atggtaagac aaaaaccaat ttgattggga tccttcagag atttctagat      5100
ggtgatcacg ttgtccctat aattgaagag atgggagccg gaacagtggg tggattcatc      5160
aagagacaac agtctaaagt tgtgcaaaat aaggtggtct attatggagt tgggatctgg      5220
agaggcttta tggatggata tcaggtccat cttgagatag aaaatgacat aggacagccc      5280
ccaaggctta ggaatgtcac aactaactgt cagagcagcc catgggatct gagtgtccca      5340
ataaggcagt gggcagaaga catgggggtc acaaacaacc aggattattc ctctaaatct      5400
agcagaggag ctagatattg gatgcattca tttaggatgc aaggacccag caagccattt      5460
ggatgcccag tttatattat taagggtgac atgtcagatg ttatcagact gagaaaagag      5520
gaggtggaga tgaaagtacg gggctctact ctcaacttgt acactaagca ccattctcat      5580
caagacttac acattttatc ttacactgca tcagacaatg atctcagtcc aggcattttc      5640
aagtcaatat cagatgaggg agtggctcaa gccctgcagt tatttgagag ggagccaagc      5700
aactgctggg tgagatgtga gtctgtagct ccaaaattca tatcagccat ccttgagata      5760
tgtgagggga agagacagat aaaaggaatc aacagaacca gactctcaga gattgtgaga      5820
atttgttctg aatcttccct aagatcaaag gtcggatcta tgttctcatt tgtcgccaat      5880
gttgaggagg cccatgatgt tgattatgat gcgttaatgg atctaatgat agaagatgct      5940
aagaacaatg cattcagtca tgttgtcgat tgcatagagt tggatgttaa tggtccttac      6000
gagatggagt cttttgatac atctgatgtc aacctctttg gccagcccca ttacaaggac      6060
atcagttcat tatctatgat tgctcatccc ttaatggata gtttgttga ttatgccatt      6120 tccaagatgg ggagagcctc agttagaaaa gttctagaga caggtcggtg ctctagcaaa      6180
gactatgatt tatcaaaggt tctcttcaga actctacaga gaccagaaaa gagcattagg      6240
atagatgatc tggagttata tgaggagaca gatgtggcgg atgacatgct aggctaagac      6300
caataagcaa agtcaggctt agatttaggg atactacgct agtattggaa tccatgtggg      6360
ttctgatact agcatagtgc tacaatattg ggcggtcttt gtgt                       6404
```

<210> SEQ ID NO 2
<211> LENGTH: 3885
<212> TYPE: DNA
<213> ORGANISM: Artificial Sequence
<220> FEATURE:
<223> OTHER INFORMATION: FMH-P8 RVF virus M segment -continued

```
<220> FEATURE:
<221> NAME/KEY: gene
<222> LOCATION: (21)..(3614)
<223> OTHER INFORMATION: FMH-P8 RFV virus gene encoding M (poly)protein

<400> SEQUENCE: 2
acacaaagac ggtgcattaa atgtatgttt tactaacaat tctgatcacg gttctggtgt      60
gtgaagcggt tattagagtg tctctaagct ccacaaaaga agagacctgt tttggtgact     120
ccaccaaccc agagatgatt gaaggagctt gggattcact cagagaggag gagatgccag     180
aggagctctc ctgttctata tcaggcataa gggaggttaa gacctcaagc caggagttat     240
acagggcatt aaaagccatc attgctgctg atggcttgaa caacatcacc tgccatggta     300
aggatcctga ggacaagatt tctctcataa agggtcctcc ttacaaaaag cgggtgggga     360
tagttcggtg taaaagacga agagatgcta agcaaatagg gagagaaacc atggcaggga     420
ttgcaatgac agtccttcca gccttagcag tttttgcttt ggcacctgtt gtttttgctg     480 aagacccca tctcaggaac agaccaggga aggggcacaa ctacattgac gggatgactc     540
aggaggatgc cacatgcaaa cctgtgacat atgctggggc atgtagcagt tttgatgtct     600
tgcttgaaaa ggggaaattt cccctttttcc agtcgtatgc tcatcataaa actctactgg     660
aagcagttca cgacactatc attgcaaagg ctgatccacc tagctgtgac cttcaaagtg     720
ctcatgggaa tccctgcatg aaagagaaac tcgtgatgaa gacacactgt ccaaatgact     780
accagtcagc tcattacctc aacaatgacg ggaaagtggc ttcagtcaag tgccctccta     840
agtatgagct cactgaggac tgcaactttt gtaggcagat gacaggtgct agcctgaaga     900
aagggtctta tcctctccaa gacttatttt gtcagtcaag tgaggatgat ggatcaaaat     960
taaaaacaaa aatgaaaggg gtctgcgaag tgggggttca agcactcaaa aagtgtaatg    1020
gccaactcag cactgcacat gaggttgtgc cctttgcagt gtttaagaac tcaaagaaag    1080
tttatcttga taagcttgac ctcaaaactg aggagaatct gctaccagac tcatttgtct    1140
gcttcgagca taagggacag tataaaggaa caatggactc tggtcagact aagagggagc    1200
tcaaaagctc tgatatctct cagtgcccca agattggagg acatggtagt aaaaagtgca    1260
ctggggacgc agcattttgc tctgcttatg agtgcactac tcagtacgcc aatgtctact    1320
gttcacatgc taatggatca gggattgtgc agatacaagt atcaggggtc tggaagaagc    1380
ctttatgtgt agggtatgag agagtggttg tgaagagaga actctctgcc aagcccatcc    1440
agagagttga gccctgcaca acttgtataa ccaaatgtgg gcctcatgga ttggttgtcc    1500
gatcaacagg gttcaagata tcatctgcag ttgcttgtgc tagcggagtt tgcgtcacag    1560
gatcgcagag tccttctacc gagattacac tcaagtatcc agggatatcc cagtcctctg    1620 gggggggacat aggggtttac atggcacatg atgatcagtc agttagctcc aaaatagtag    1680
ctcactgccc cccccaggac ccgtgcttag tgcatggctg catagtgtgt gctcatggcc    1740
taataaatta ccagtgtcac actactctca gtgcctttat tgttgtgttt gtattcagtt    1800
ctattgcaat aacttgttta gctattcttt atagggtgct caagtgccta aagattgccc    1860
caaggaaggt tctaaatcca ctaatgtgga ttacagcctt catcagatgg gtgtataaga    1920
agatggttgc tagagtggca gacaatatta atcaagtgaa cagggaaata ggatggatgg    1980
aagggggtca gttggttcta gggaaccctg cccctattcc tcgtcatgcc ccaatcccac    2040
gttatagcac atacctaatg ctactattga ttgtctcata tgcatcagca tgttcagaac    2100
tgattcaggc aagctccaga atcaccactt gctccacaga gggtgttaac accaagtgta    2160
```

-continued

```
gactgtctgg cacagcattg atcagggcag ggtcagttgg ggcagaggct tgtttaatgt   2220
tgaagggggt caaggaagat caaaccaaat tcttgaagat aaaaactgtc tcaagtgagc   2280
tatcgtgcag ggagggccag agctattgga ctgggtcctt tagtcccaaa tgtctgagct   2340
caaggagatg ccatcttgtt ggagaatgtc atgtgaatag gtgtctgtct ggagggaca   2400 atgaaacttc agcagagttt tcatttgttg gggaaagcac gaccatgcga gagaataagt   2460
gttttgagca gtgtggagga tggggtgtg ggtgcttcaa tgtgaaccca tcttgcttat   2520
ttgtgcacac gtacctgcag tcagttagaa aagaggccct tagagttttt aactgtatcg   2580
actgggtgca taaactcagt ctagagatca cagactttga tggctctgtt tcaacaatag   2640
acttgggagc atcatctagc cgtttcacaa actggggttc agttagcctc tcactggacg   2700
cagagggtat ttcaggctca aatagctttt ctttcattga gagcccaggc aaagggtatg   2760
caattgttga tgagccattc tcagaaattc ctcggcaagg gttcttgggg gagatcaggt   2820
gtaattcaga gtcctcagtc ctgagtgctc atgaatcatg ccttagggta ccaaacctta   2880
tctcatacaa gcccatgata gatcaattgg agtgcacaac aaatctgatt gatcctttg   2940 ttgtctttga gaggggttct ctgccacaga caaggaatga aaaaaccttt gcagcttcaa   3000
aaggaaatag gggtgttcaa gctttctcta agggctctgt acaagctgat ctaactctga   3060
tgtttgacaa ttttgaggtg gactttgtgg gagcagccgt atcttgtgat gccgccttct   3120
taaacttgac aggttgctat tcttgcaatg cgggagccag ggtctgcctg tctatcacat   3180
ccacaggaac tggaactctc tctgcccaca ataaggatgg gtctctgcac atagttcttc   3240
catcagagaa tggaacaaaa gatcagtgtc agatactaca cttcactata cctgaagtag   3300
aggaggagtt tatgtactct tgtgatggag atgagcggcc tctgttggtg aaagggactc   3360
tgatagttat tgatccattt gatgataggc gggaagcagg gggggaatca acagttgtga   3420
atccaaaatc tggatcttgg aatttctttg actggttttc tggactcatg agttggtttg   3480
gagggcctct taaaactata ctcctcattt gcctgtatgt tgcattatca attgggctct   3540
ttttcctcct tatatatctt ggaaaaacag gcctctctaa aatgtggctt gctgctacta   3600
agaaggcctc atagatcagt acgtgtagaa gcaatatgta gaaacaagtg gacataagca   3660
aacctaatta tgtaaatatt gtacagatag gtcaaattat tgggatatcc aagcttagat   3720
gcttatgcaa tattactttt gatgtaagct tagttgtaat ttggggtggt ggggtgaggc   3780
agcagcagtc tcaagtgctt gtgaatattc tagttggcgt gaatgtcttt tgccagatta   3840
gctgggaatt aaactaactc tttgaagttg caccggtctt tgtgt               3885
```

```
<210> SEQ ID NO 3
<211> LENGTH: 1691
<212> TYPE: DNA
<213> ORGANISM: Artificial Sequence
<220> FEATURE:
<223> OTHER INFORMATION: FMH-P8 RVF virus S segment
<220> FEATURE:
<221> NAME/KEY: gene
<222> LOCATION: (35)..(832)
<223> OTHER INFORMATION: FMH-P8 RVF virus gene encoding NSs protein
<220> FEATURE:
<221> NAME/KEY: gene
<222> LOCATION: (916)..(1653)
<223> OTHER INFORMATION: FMH-P8 RVFV gene encoding N protein
      (complementary)
<400> SEQUENCE: 3
```

```
acacaaagac cccctagtgc ttatcaagtg tatcatggat tactttcctg tgatatctgt   60
tgatttgcag agtggtcgtc gtgttgtgtc agtggagtac attagaggtg atggtcctcc   120
```

-continued

```
cagaatacct tattctatgg ttgggccctg ttgtgtcttt ctcatgcacc atcgtcctag        180
tcacgagatt cgcttgcgat tctctgattt ctacaatgtc ggagaattcc cataccgagt        240
cggacttgga gactttgtat caaacgttgc acctccacta gcaaagcctt ttcagagact        300
tattgatcta ataggccata tgactcttag tgatttcaca aggttcccca atctgaaaga        360
agccatatcc tggcctcttg agaaccctc cctggctttc tttgacctaa gctccaccag        420
agtgcatagg tctgatgata ttagaaggga ccagattgct actctagcaa tgaggagctg        480
caagattacc aatgatctgg aggactcctt tgttggctta cacaggatga tagtgaccga        540
ggctatcctc agagggattg acttgtgcct gttgccaggc tttgatctca tgtatgaagt        600
tgctcacgtt cagtgtgttc ggctcctgca ggcagcaaga gaggatattt ctaatgctgt        660
agttccaaac tcagctctca ttgctcttat ggaggagagc ttgatgctgc gctcatcact        720
ccctagcatg atggggagaa acaactgggt tccagttgtt cctccaatcc cagatgttga        780
gatagaatca gaggaagaga gtgatgacga tggatttgtt gaggttgatt agagattaag        840
gctgccccac cccccacccc caatcccgac cgtaacccca accacctcct tttccccaaa        900
cccctgggca gccacttagg ctgctgtctt gtacgcctga gcagctgcca taacagctgc        960
tgacggcttc ccattggaat ccacaagccc aaaagctttc aagaattctc tcctcttctc       1020
atggcttata aagttgctat tcactgctgc attcattggc tgcgtgaacg ttgcggcaac       1080
ctcctccttt gttctacctc ggaggtttgg gttgatgacc cgggagaact gcagcagata       1140
cagagagtga gcatccaata ttgcccttag atagtcttct ggtagagaag ggtccaccat       1200
gccagcaaag ctggggtgca tcatatgcct tgggtatgca ggggataggc catccatggt       1260
ggtcccagtg acaggaagcc actcactcaa gacgaccaaa gcctggcaag tccagccagc       1320
cagggcagca gcaactcgtg atagagtcaa ctcatcccgg gaaggattcc cctcctttag       1380
cttatacttg ttgatgagag cctccacagt tgctttgcct tctttcgaca ttttcatcat       1440
catcctccgg ggcttgttgc cacgagtcag agccagaaca atcattttct tggcatcctt       1500
ctcccagcca gcccccaccat actgctttaa gagttcgata accctacggg catcaaatcc      1560
ttgataagca aactctcgga cccactgttc aatctcattg cggtccactg cttgagcagc       1620
aaactggatc gcaagctctt gataattgtc cattattgta atagtgtttg tatctctagg       1680
gagctttgtg t                                                             1691
```

<210> SEQ ID NO 4
<211> LENGTH: 2092
<212> TYPE: PRT
<213> ORGANISM: Artificial Sequence
<220> FEATURE:
<223> OTHER INFORMATION: FMH-P8 RVFV L protein
<220> FEATURE:
<221> NAME/KEY: MUTAGEN
<222> LOCATION: (100)..(100)
<223> OTHER INFORMATION: Thr
<220> FEATURE:
<221> NAME/KEY: MUTAGEN
<222> LOCATION: (375)..(375)
<223> OTHER INFORMATION: Tyr
<220> FEATURE:
<221> NAME/KEY: MUTAGEN
<222> LOCATION: (924)..(924)
<223> OTHER INFORMATION: Ser
<220> FEATURE:
<221> NAME/KEY: MUTAGEN
<222> LOCATION: (1050)..(1050)
<223> OTHER INFORMATION: Val
<220> FEATURE:

-continued

```
<221> NAME/KEY: MUTAGEN
<222> LOCATION: (1303)..(1303)
<223> OTHER INFORMATION: Thr
<220> FEATURE:
<221> NAME/KEY: MUTAGEN
<222> LOCATION: (1629)..(1629)
<223> OTHER INFORMATION: Phe
<220> FEATURE:
<221> NAME/KEY: MUTAGEN
<222> LOCATION: (2071)..(2071)
<223> OTHER INFORMATION: Lys

<400> SEQUENCE: 4

Met Asp Ser Ile Leu Ser Lys Gln Leu Val Asp Lys Thr Gly Phe Val
1               5                   10                  15

Arg Val Pro Ile Lys His Tyr Asp Cys Thr Met Leu Thr Leu Ala Leu
                20                  25                  30

Pro Thr Phe Asp Val Ser Lys Met Val Asp Arg Ile Thr Ile Asp Phe
            35                  40                  45

Asn Leu Asp Asp Ile Gln Gly Ala Ser Glu Ile Gly Ser Thr Leu Leu
        50                  55                  60

Pro Ser Met Ser Ile Asp Val Glu Asp Met Ala Asn Phe Val His Asp
65                  70                  75                  80

Phe Thr Phe Gly His Leu Ala Asp Lys Thr Asp Arg Leu Leu Met Arg
                85                  90                  95

Glu Phe Pro Thr Met Asn Asp Gly Phe Asp His Leu Ser Pro Asp Met
            100                 105                 110

Ile Ile Lys Thr Thr Ser Gly Met Tyr Asn Ile Val Glu Phe Thr Thr
            115                 120                 125

Phe Arg Gly Asp Glu Arg Gly Ala Phe Gln Ala Ala Met Thr Lys Leu
        130                 135                 140

Ala Lys Tyr Glu Val Pro Cys Glu Asn Arg Ser Gln Gly Arg Thr Val
145                 150                 155                 160

Val Leu Tyr Val Val Ser Ala Tyr Arg His Gly Val Trp Ser Asn Leu
                165                 170                 175

Glu Leu Glu Asp Ser Glu Ala Glu Glu Met Val Tyr Arg Tyr Arg Leu
            180                 185                 190

Ala Leu Ser Val Met Asp Glu Leu Arg Thr Leu Phe Pro Glu Leu Ser
        195                 200                 205

Ser Thr Asp Glu Glu Leu Gly Lys Thr Glu Arg Glu Leu Leu Ala Met
        210                 215                 220

Val Ser Ser Ile Gln Ile Asn Trp Ser Val Thr Glu Ser Val Phe Pro
225                 230                 235                 240

Pro Phe Ser Arg Glu Met Phe Asp Arg Phe Arg Ser Ser Pro Pro Asp
            245                 250                 255

Ser Glu Tyr Ile Thr Arg Ile Val Ser Arg Cys Leu Ile Asn Ser Gln
            260                 265                 270

Glu Lys Leu Ile Asn Asn Ser Phe Phe Ala Glu Gly Asn Asp Lys Val
        275                 280                 285

Leu Arg Phe Ser Lys Asn Ala Glu Glu Cys Ser Leu Ala Ile Glu Arg
        290                 295                 300

Ala Leu Asn Gln Tyr Arg Ala Glu Asp Asn Leu Arg Asp Leu Asn Asp
305                 310                 315                 320

His Lys Ser Thr Ile Gln Leu Pro Pro Trp Leu Ser Tyr His Asp Ala
            325                 330                 335

Asp Gly Lys Asp Leu Cys Pro Leu Gln Gly Leu Asp Val Arg Gly Asp
        340                 345                 350
```

-continued

```
His Pro Met Cys Asn Leu Trp Arg Glu Val Val Thr Ser Ala Asn Leu
        355                 360                 365

Glu Glu Ile Glu Arg Met Tyr Asp Asp Ala Ala Ala Glu Leu Glu Phe
        370                 375                 380

Ala Leu Ser Gly Val Lys Asp Arg Pro Asp Glu Arg Asn Arg Tyr His
385                 390                 395                 400

Arg Val His Leu Asn Met Asp Ser Asp Ser Val Tyr Ile Ala Ala
                405                 410                 415

Leu Gly Val Asn Gly Lys Lys His Lys Ala Asp Thr Leu Val Gln Gln
                420                 425                 430

Met Arg Asp Arg Ser Lys Gln Pro Phe Ser Pro Asp His Asp Val Asp
        435                 440                 445

His Ile Ser Glu Phe Leu Ser Ala Cys Ser Ser Asp Leu Trp Ala Thr
        450                 455                 460

Asp Glu Asp Leu Tyr Asn Pro Leu Ser Cys Asp Lys Glu Leu Arg Leu
465                 470                 475                 480

Ala Ala Gln Arg Ile His Gln Pro Ser Leu Ser Glu Arg Gly Phe Asn
                485                 490                 495

Glu Ile Ile Thr Glu His Tyr Arg Phe Met Gly Ser Arg Ile Gly Ser
                500                 505                 510

Trp Cys Gln Met Val Ser Leu Ile Gly Ala Glu Leu Ser Ala Ser Val
        515                 520                 525

Lys Gln His Val Lys Pro Asn Tyr Phe Val Ile Lys Arg Leu Leu Gly
        530                 535                 540

Ser Gly Ile Phe Leu Leu Ile Lys Pro Thr Ser Ser Lys Ser His Ile
545                 550                 555                 560

Phe Val Ser Phe Ala Ile Lys Arg Ser Cys Trp Ala Phe Asp Leu Ser
                565                 570                 575

Thr Ser Arg Val Phe Lys Pro Tyr Ile Asp Ala Gly Asp Leu Leu Val
                580                 585                 590

Thr Asp Phe Val Ser Tyr Lys Leu Ser Lys Leu Thr Asn Leu Cys Lys
        595                 600                 605

Cys Val Ser Leu Met Glu Ser Ser Phe Ser Phe Trp Ala Glu Ala Phe
        610                 615                 620

Gly Ile Pro Ser Trp Asn Phe Val Ser Asp Leu Phe Arg Ser Ser Asp
625                 630                 635                 640

Ser Ala Ala Met Asp Ala Ser Tyr Met Gly Lys Leu Ser Leu Leu Thr
                645                 650                 655

Leu Leu Glu Asp Lys Ala Thr Thr Glu Glu Leu Gln Thr Ile Ala Arg
                660                 665                 670

Tyr Ile Ile Met Glu Gly Phe Val Ser Pro Pro Glu Ile Pro Lys Pro
                675                 680                 685

His Lys Met Thr Ser Lys Phe Pro Lys Val Leu Arg Ser Glu Leu Gln
        690                 695                 700

Val Tyr Leu Leu Asn Cys Leu Cys Arg Thr Ile Gln Arg Ile Ala Gly
705                 710                 715                 720

Glu Pro Phe Ile Leu Lys Lys Lys Asp Gly Ser Ile Ser Trp Gly Gly
                725                 730                 735

Met Phe Asn Pro Phe Ser Gly Arg Pro Leu Leu Asp Met Gln Pro Leu
                740                 745                 750

Ile Ser Cys Cys Tyr Asn Gly Tyr Phe Lys Asn Lys Glu Glu Glu Thr
                755                 760                 765
```

```
Glu Pro Ser Ser Leu Ser Gly Met Tyr Lys Lys Ile Ile Glu Leu Glu
    770             775             780

His Leu Arg Pro Gln Ser Asp Ala Phe Leu Gly Tyr Lys Asp Pro Glu
785             790             795             800

Leu Pro Arg Met His Glu Phe Ser Val Ser Tyr Leu Lys Glu Ala Cys
            805             810             815

Asn His Ala Lys Leu Val Leu Arg Ser Leu Tyr Gly Gln Asn Phe Met
            820             825             830

Glu Gln Ile Asp Asn Gln Ile Ile Arg Glu Leu Ser Gly Leu Thr Leu
        835             840             845

Glu Arg Leu Ala Thr Leu Lys Ala Thr Ser Asn Phe Asn Glu Asn Trp
850             855             860

Tyr Val Tyr Lys Asp Val Ala Asp Lys Asn Tyr Thr Arg Asp Lys Leu
865             870             875             880

Leu Val Lys Met Ser Lys Tyr Ala Ser Glu Gly Lys Ser Leu Ala Ile
            885             890             895

Gln Lys Phe Glu Asp Cys Met Arg Gln Ile Glu Ser Gln Gly Cys Met
            900             905             910

His Ile Cys Leu Phe Lys Lys Gln Gln His Gly Ser Leu Arg Glu Ile
        915             920             925

Tyr Val Met Gly Ala Glu Glu Arg Ile Val Gln Ser Val Val Glu Thr
    930             935             940

Ile Ala Arg Ser Ile Gly Lys Phe Phe Ala Ser Asp Thr Leu Cys Asn
945             950             955             960

Pro Pro Asn Lys Val Lys Ile Pro Glu Thr His Gly Ile Arg Ala Arg
            965             970             975

Lys Gln Cys Lys Gly Pro Val Trp Thr Cys Ala Thr Ser Asp Asp Ala
            980             985             990

Arg Lys Trp Asn Gln Gly His Phe  Val Thr Lys Phe Ala  Leu Met Leu
        995             1000                1005

Cys Glu  Phe Thr Ser Pro Lys  Trp Trp Pro Leu Ile  Ile Arg Gly
    1010            1015                1020

Cys Ser  Met Phe Thr Arg Lys  Arg Met Met Asn  Leu Asn Tyr
    1025            1030                1035

Leu Lys  Ile Leu Asp Gly His  Arg Glu Leu Asp Val  Arg Asp Asp
    1040            1045                1050

Phe Val  Met Asp Leu Phe Lys  Ala Tyr His Gly Glu  Ala Glu Val
    1055            1060                1065

Pro Trp  Ala Phe Lys Gly Lys  Thr Tyr Leu Glu Thr  Thr Thr Gly
    1070            1075                1080

Met Met  Gln Gly Ile Leu His  Tyr Thr Ser Ser Leu  Leu His Thr
    1085            1090                1095

Ile His  Gln Glu Tyr Ile Arg  Ser Leu Ser Phe Lys  Ile Phe Asn
    1100            1105                1110

Leu Lys  Val Ala Pro Glu Met  Ser Lys Ser Leu Val  Cys Asp Met
    1115            1120                1125

Met Gln  Gly Ser Asp Asp Ser  Ser Met Leu Ile Ser  Phe Pro Ala
    1130            1135                1140

Asp Asp  Glu Lys Val Leu Thr  Arg Cys Lys Val Ala  Ala Ala Ile
    1145            1150                1155

Cys Phe  Arg Met Lys Lys Glu  Leu Gly Val Tyr Leu  Ala Ile Tyr
    1160            1165                1170

Pro Ser  Glu Lys Ser Thr Ala  Asn Thr Asp Phe Val  Met Glu Tyr
```

-continued

```
        1175                1180                1185

Asn Ser  Glu Phe Tyr Phe His  Thr Gln His Val Arg  Pro Thr Ile
    1190                1195                1200

Arg Trp  Ile Ala Ala Cys Cys  Ser Leu Pro Glu Val  Glu Thr Leu
    1205                1210                1215

Val Ala  Arg Gln Glu Glu Ala  Ser Asn Leu Met Thr  Ser Val Thr
    1220                1225                1230

Glu Gly  Gly Gly Ser Phe Ser  Leu Ala Ala Met Ile  Gln Gln Ala
    1235                1240                1245

Gln Cys  Thr Leu His Tyr Met  Leu Met Gly Met Gly  Val Ser Glu
    1250                1255                1260

Leu Phe  Leu Glu Tyr Lys Lys  Ala Val Leu Lys Trp  Asn Asp Pro
    1265                1270                1275

Gly Leu  Gly Phe Phe Leu Leu  Asp Asn Pro Tyr Ala  Cys Gly Leu
    1280                1285                1290

Gly Gly  Phe Arg Phe Asn Leu  Phe Lys Thr Ile Thr  Arg Thr Asp
    1295                1300                1305

Leu Gln  Lys Leu Tyr Ala Phe  Phe Met Lys Lys Val  Lys Gly Ser
    1310                1315                1320

Ala Ala  Arg Asp Trp Ala Asp  Glu Asp Val Thr Ile  Pro Glu Thr
    1325                1330                1335

Cys Ser  Val Ser Pro Gly Gly  Ala Leu Ile Leu Ser  Ser Ser Leu
    1340                1345                1350

Lys Trp  Gly Ser Arg Lys Lys  Phe Gln Lys Leu Arg  Asp Arg Leu
    1355                1360                1365

Asn Ile  Pro Glu Asn Trp Ile  Glu Leu Ile Asn Glu  Asn Pro Glu
    1370                1375                1380

Val Leu  Tyr Arg Ala Pro Arg  Thr Gly Pro Glu Ile  Leu Leu Arg
    1385                1390                1395

Ile Ala  Glu Lys Val His Ser  Pro Gly Val Val Ser  Ser Leu Ser
    1400                1405                1410

Ser Gly  Asn Ala Val Cys Lys  Val Met Ala Ser Ala  Val Tyr Phe
    1415                1420                1425

Leu Ser  Ala Thr Ile Phe Glu  Asp Thr Gly Arg Pro  Glu Phe Asn
    1430                1435                1440

Phe Leu  Glu Asp Ser Lys Tyr  Ser Leu Leu Gln Lys  Met Ala Ala
    1445                1450                1455

Tyr Ser  Gly Phe His Gly Phe  Asn Asp Met Glu Pro  Glu Asp Ile
    1460                1465                1470

Leu Phe  Leu Phe Pro Asn Ile  Glu Glu Leu Glu Ser  Leu Asp Ser
    1475                1480                1485

Ile Val  Tyr Asn Lys Gly Glu  Ile Asp Ile Ile Pro  Arg Val Asn
    1490                1495                1500

Ile Arg  Asp Ala Thr Gln Thr  Arg Val Thr Ile Phe  Asn Glu Gln
    1505                1510                1515

Lys Thr  Leu Arg Thr Ser Pro  Glu Lys Leu Val Ser  Asp Lys Trp
    1520                1525                1530

Phe Gly  Thr Gln Lys Ser Arg  Ile Gly Lys Thr Thr  Phe Leu Ala
    1535                1540                1545

Glu Trp  Glu Lys Leu Lys Lys  Ile Val Lys Trp Leu  Glu Asp Thr
    1550                1555                1560

Pro Glu  Ala Thr Leu Ala His  Thr Pro Leu Asn Asn  His Ile Gln
    1565                1570                1575
```

```
Val Arg Asn Phe Phe Ala Arg Met Glu Ser Lys Pro Arg Thr Val
    1580              1585              1590

Arg Ile Thr Gly Ala Pro Val Lys Lys Arg Ser Gly Val Ser Lys
    1595              1600              1605

Ile Ala Met Val Ile Arg Asp Asn Phe Ser Arg Met Gly His Leu
    1610              1615              1620

Arg Gly Val Glu Asp Phe Ala Gly Phe Thr Arg Ser Val Ser Ala
    1625              1630              1635

Glu Ile Leu Lys His Phe Leu Phe Cys Ile Leu Gln Gly Pro Tyr
    1640              1645              1650

Ser Glu Ser Tyr Lys Leu Gln Leu Ile Tyr Arg Val Leu Ser Ser
    1655              1660              1665

Val Ser Asn Val Glu Ile Lys Glu Ser Asp Gly Lys Thr Lys Thr
    1670              1675              1680

Asn Leu Ile Gly Ile Leu Gln Arg Phe Leu Asp Gly Asp His Val
    1685              1690              1695

Val Pro Ile Ile Glu Glu Met Gly Ala Gly Thr Val Gly Gly Phe
    1700              1705              1710

Ile Lys Arg Gln Gln Ser Lys Val Val Gln Asn Lys Val Val Tyr
    1715              1720              1725

Tyr Gly Val Gly Ile Trp Arg Gly Phe Met Asp Gly Tyr Gln Val
    1730              1735              1740

His Leu Glu Ile Glu Asn Asp Ile Gly Gln Pro Pro Arg Leu Arg
    1745              1750              1755

Asn Val Thr Thr Asn Cys Gln Ser Ser Pro Trp Asp Leu Ser Val
    1760              1765              1770

Pro Ile Arg Gln Trp Ala Glu Asp Met Gly Val Thr Asn Asn Gln
    1775              1780              1785

Asp Tyr Ser Ser Lys Ser Ser Arg Gly Ala Arg Tyr Trp Met His
    1790              1795              1800

Ser Phe Arg Met Gln Gly Pro Ser Lys Pro Phe Gly Cys Pro Val
    1805              1810              1815

Tyr Ile Ile Lys Gly Asp Met Ser Asp Val Ile Arg Leu Arg Lys
    1820              1825              1830

Glu Glu Val Glu Met Lys Val Arg Gly Ser Thr Leu Asn Leu Tyr
    1835              1840              1845

Thr Lys His His Ser His Gln Asp Leu His Ile Leu Ser Tyr Thr
    1850              1855              1860

Ala Ser Asp Asn Asp Leu Ser Pro Gly Ile Phe Lys Ser Ile Ser
    1865              1870              1875

Asp Glu Gly Val Ala Gln Ala Leu Gln Leu Phe Glu Arg Glu Pro
    1880              1885              1890

Ser Asn Cys Trp Val Arg Cys Glu Ser Val Ala Pro Lys Phe Ile
    1895              1900              1905

Ser Ala Ile Leu Glu Ile Cys Glu Gly Lys Arg Gln Ile Lys Gly
    1910              1915              1920

Ile Asn Arg Thr Arg Leu Ser Glu Ile Val Arg Ile Cys Ser Glu
    1925              1930              1935

Ser Ser Leu Arg Ser Lys Val Gly Ser Met Phe Ser Phe Val Ala
    1940              1945              1950

Asn Val Glu Glu Ala His Asp Val Asp Tyr Asp Ala Leu Met Asp
    1955              1960              1965
```

```
Leu Met  Ile Glu Asp Ala Lys  Asn Asn Ala Phe Ser  His Val Val
    1970             1975              1980

Asp Cys  Ile Glu Leu Asp Val  Asn Gly Pro Tyr Glu  Met Glu Ser
    1985             1990              1995

Phe Asp  Thr Ser Asp Val Asn  Leu Phe Gly Pro Ala  His Tyr Lys
    2000             2005              2010

Asp Ile  Ser Ser Leu Ser Met  Ile Ala His Pro Leu  Met Asp Lys
    2015             2020              2025

Phe Val  Asp Tyr Ala Ile Ser  Lys Met Gly Arg Ala  Ser Val Arg
    2030             2035              2040

Lys Val  Leu Glu Thr Gly Arg  Cys Ser Ser Lys Asp  Tyr Asp Leu
    2045             2050              2055

Ser Lys  Val Leu Phe Arg Thr  Leu Gln Arg Pro Glu  Lys Ser Ile
    2060             2065              2070

Arg Ile  Asp Asp Leu Glu Leu  Tyr Glu Glu Thr Asp  Val Ala Asp
    2075             2080              2085

Asp Met  Leu Gly
    2090

<210> SEQ ID NO 5
<211> LENGTH: 1197
<212> TYPE: PRT
<213> ORGANISM: Artificial Sequence
<220> FEATURE:
<223> OTHER INFORMATION: FMH-P8 RVFV M (poly)protein
<220> FEATURE:
<221> NAME/KEY: MUTAGEN
<222> LOCATION: (26)..(26)
<223> OTHER INFORMATION: Lys
<220> FEATURE:
<221> NAME/KEY: MUTAGEN
<222> LOCATION: (108)..(108)
<223> OTHER INFORMATION: Tyr
<220> FEATURE:
<221> NAME/KEY: MUTAGEN
<222> LOCATION: (118)..(118)
<223> OTHER INFORMATION: Lys
<220> FEATURE:
<221> NAME/KEY: MUTAGEN
<222> LOCATION: (210)..(210)
<223> OTHER INFORMATION: Lys
<220> FEATURE:
<221> NAME/KEY: MUTAGEN
<222> LOCATION: (333)..(333)
<223> OTHER INFORMATION: Asn
<220> FEATURE:
<221> NAME/KEY: MUTAGEN
<222> LOCATION: (427)..(427)
<223> OTHER INFORMATION: Thr
<220> FEATURE:
<221> NAME/KEY: MUTAGEN
<222> LOCATION: (432)..(432)
<223> OTHER INFORMATION: Val
<220> FEATURE:
<221> NAME/KEY: MUTAGEN
<222> LOCATION: (487)..(487)
<223> OTHER INFORMATION: Gly
<220> FEATURE:
<221> NAME/KEY: MUTAGEN
<222> LOCATION: (540)..(540)
<223> OTHER INFORMATION: Tyr
<220> FEATURE:
<221> NAME/KEY: MUTAGEN
<222> LOCATION: (582)..(582)
<223> OTHER INFORMATION: Thr
<220> FEATURE:
<221> NAME/KEY: MUTAGEN
<222> LOCATION: (587)..(587)
<223> OTHER INFORMATION: Ile
<220> FEATURE:
```

```
<221> NAME/KEY: MUTAGEN
<222> LOCATION: (950)..(950)
<223> OTHER INFORMATION: Val
<220> FEATURE:
<221> NAME/KEY: MUTAGEN
<222> LOCATION: (1090)..(1090)
<223> OTHER INFORMATION: Ile
<220> FEATURE:
<221> NAME/KEY: MUTAGEN
<222> LOCATION: (1116)..(1116)
<223> OTHER INFORMATION: Val
<220> FEATURE:
<221> NAME/KEY: MUTAGEN
<222> LOCATION: (1182)..(1182)
<223> OTHER INFORMATION: Lys

<400> SEQUENCE: 5

Met Tyr Val Leu Leu Thr Ile Leu Ile Thr Val Leu Val Cys Glu Ala
1               5                   10                  15

Val Ile Arg Val Ser Leu Ser Ser Thr Lys Glu Glu Thr Cys Phe Gly
            20                  25                  30

Asp Ser Thr Asn Pro Glu Met Ile Glu Gly Ala Trp Asp Ser Leu Arg
        35                  40                  45

Glu Glu Glu Met Pro Glu Glu Leu Ser Cys Ser Ile Ser Gly Ile Arg
    50                  55                  60

Glu Val Lys Thr Ser Ser Gln Glu Leu Tyr Arg Ala Leu Lys Ala Ile
65                  70                  75                  80

Ile Ala Ala Asp Gly Leu Asn Asn Ile Thr Cys His Gly Lys Asp Pro
                85                  90                  95

Glu Asp Lys Ile Ser Leu Ile Lys Gly Pro Pro Tyr Lys Lys Arg Val
            100                 105                 110

Gly Ile Val Arg Cys Lys Arg Arg Asp Ala Lys Gln Ile Gly Arg
            115                 120                 125

Glu Thr Met Ala Gly Ile Ala Met Thr Val Leu Pro Ala Leu Ala Val
    130                 135                 140

Phe Ala Leu Ala Pro Val Val Phe Ala Glu Asp Pro His Leu Arg Asn
145                 150                 155                 160

Arg Pro Gly Lys Gly His Asn Tyr Ile Asp Gly Met Thr Gln Glu Asp
                165                 170                 175

Ala Thr Cys Lys Pro Val Thr Tyr Ala Gly Ala Cys Ser Ser Phe Asp
                180                 185                 190

Val Leu Leu Glu Lys Gly Lys Phe Pro Leu Phe Gln Ser Tyr Ala His
            195                 200                 205

His Lys Thr Leu Leu Glu Ala Val His Asp Thr Ile Ile Ala Lys Ala
    210                 215                 220

Asp Pro Pro Ser Cys Asp Leu Gln Ser Ala His Gly Asn Pro Cys Met
225                 230                 235                 240

Lys Glu Lys Leu Val Met Lys Thr His Cys Pro Asn Asp Tyr Gln Ser
                245                 250                 255

Ala His Tyr Leu Asn Asn Asp Gly Lys Val Ala Ser Val Lys Cys Pro
                260                 265                 270

Pro Lys Tyr Glu Leu Thr Glu Asp Cys Asn Phe Cys Arg Gln Met Thr
            275                 280                 285

Gly Ala Ser Leu Lys Lys Gly Ser Tyr Pro Leu Gln Asp Leu Phe Cys
    290                 295                 300

Gln Ser Ser Glu Asp Asp Gly Ser Lys Leu Lys Thr Lys Met Lys Gly
305                 310                 315                 320

Val Cys Glu Val Gly Val Gln Ala Leu Lys Lys Cys Asn Gly Gln Leu
```

-continued

```
              325               330               335
Ser Thr Ala His Glu Val Val Pro Phe Ala Val Phe Lys Asn Ser Lys
            340               345               350

Lys Val Tyr Leu Asp Lys Leu Asp Leu Lys Thr Glu Glu Asn Leu Leu
            355               360               365

Pro Asp Ser Phe Val Cys Phe Glu His Lys Gly Gln Tyr Lys Gly Thr
            370               375               380

Met Asp Ser Gly Gln Thr Lys Arg Glu Leu Lys Ser Ser Asp Ile Ser
385               390               395               400

Gln Cys Pro Lys Ile Gly Gly His Gly Ser Lys Lys Cys Thr Gly Asp
                405               410               415

Ala Ala Phe Cys Ser Ala Tyr Glu Cys Thr Thr Gln Tyr Ala Asn Val
                420               425               430

Tyr Cys Ser His Ala Asn Gly Ser Gly Ile Val Gln Ile Gln Val Ser
                435               440               445

Gly Val Trp Lys Lys Pro Leu Cys Val Gly Tyr Glu Arg Val Val Val
            450               455               460

Lys Arg Glu Leu Ser Ala Lys Pro Ile Gln Arg Val Glu Pro Cys Thr
465               470               475               480

Thr Cys Ile Thr Lys Cys Gly Pro His Gly Leu Val Val Arg Ser Thr
                485               490               495

Gly Phe Lys Ile Ser Ser Ala Val Ala Cys Ala Ser Gly Val Cys Val
                500               505               510

Thr Gly Ser Gln Ser Pro Ser Thr Glu Ile Thr Leu Lys Tyr Pro Gly
            515               520               525

Ile Ser Gln Ser Ser Gly Gly Asp Ile Gly Val Tyr Met Ala His Asp
            530               535               540

Asp Gln Ser Val Ser Ser Lys Ile Val Ala His Cys Pro Pro Gln Asp
545               550               555               560

Pro Cys Leu Val His Gly Cys Ile Val Cys Ala His Gly Leu Ile Asn
                565               570               575

Tyr Gln Cys His Thr Thr Leu Ser Ala Phe Ile Val Val Phe Val Phe
                580               585               590

Ser Ser Ile Ala Ile Thr Cys Leu Ala Ile Leu Tyr Arg Val Leu Lys
            595               600               605

Cys Leu Lys Ile Ala Pro Arg Lys Val Leu Asn Pro Leu Met Trp Ile
            610               615               620

Thr Ala Phe Ile Arg Trp Val Tyr Lys Lys Met Val Ala Arg Val Ala
625               630               635               640

Asp Asn Ile Asn Gln Val Asn Arg Glu Ile Gly Trp Met Glu Gly Gly
                645               650               655

Gln Leu Val Leu Gly Asn Pro Ala Pro Ile Pro Arg His Ala Pro Ile
            660               665               670

Pro Arg Tyr Ser Thr Tyr Leu Met Leu Leu Leu Ile Val Ser Tyr Ala
            675               680               685

Ser Ala Cys Ser Glu Leu Ile Gln Ala Ser Ser Arg Ile Thr Thr Cys
            690               695               700

Ser Thr Glu Gly Val Asn Thr Lys Cys Arg Leu Ser Gly Thr Ala Leu
705               710               715               720

Ile Arg Ala Gly Ser Val Gly Ala Glu Ala Cys Leu Met Leu Lys Gly
                725               730               735

Val Lys Glu Asp Gln Thr Lys Phe Leu Lys Ile Lys Thr Val Ser Ser
            740               745               750
```

-continued

```
Glu Leu Ser Cys Arg Glu Gly Gln Ser Tyr Trp Thr Gly Ser Phe Ser
        755                 760                 765

Pro Lys Cys Leu Ser Ser Arg Arg Cys His Leu Val Gly Glu Cys His
        770                 775                 780

Val Asn Arg Cys Leu Ser Trp Arg Asp Asn Glu Thr Ser Ala Glu Phe
785                 790                 795                 800

Ser Phe Val Gly Glu Ser Thr Thr Met Arg Glu Asn Lys Cys Phe Glu
                805                 810                 815

Gln Cys Gly Gly Trp Gly Cys Gly Cys Phe Asn Val Asn Pro Ser Cys
                820                 825                 830

Leu Phe Val His Thr Tyr Leu Gln Ser Val Arg Lys Glu Ala Leu Arg
                835                 840                 845

Val Phe Asn Cys Ile Asp Trp Val His Lys Leu Ser Leu Glu Ile Thr
        850                 855                 860

Asp Phe Asp Gly Ser Val Ser Thr Ile Asp Leu Gly Ala Ser Ser Ser
865                 870                 875                 880

Arg Phe Thr Asn Trp Gly Ser Val Ser Leu Ser Leu Asp Ala Glu Gly
                885                 890                 895

Ile Ser Gly Ser Asn Ser Phe Ser Phe Ile Glu Ser Pro Gly Lys Gly
                900                 905                 910

Tyr Ala Ile Val Asp Glu Pro Phe Ser Glu Ile Pro Arg Gln Gly Phe
                915                 920                 925

Leu Gly Glu Ile Arg Cys Asn Ser Glu Ser Ser Val Leu Ser Ala His
        930                 935                 940

Glu Ser Cys Leu Arg Val Pro Asn Leu Ile Ser Tyr Lys Pro Met Ile
945                 950                 955                 960

Asp Gln Leu Glu Cys Thr Thr Asn Leu Ile Asp Pro Phe Val Val Phe
                965                 970                 975

Glu Arg Gly Ser Leu Pro Gln Thr Arg Asn Glu Lys Thr Phe Ala Ala
                980                 985                 990

Ser Lys Gly Asn Arg Gly Val Gln  Ala Phe Ser Lys Gly  Ser Val Gln
        995                 1000                 1005

Ala Asp  Leu Thr Leu Met Phe  Asp Asn Phe Glu Val  Asp Phe Val
    1010                 1015                 1020

Gly Ala  Ala Val Ser Cys Asp  Ala Ala Phe Leu Asn  Leu Thr Gly
    1025                 1030                 1035

Cys Tyr  Ser Cys Asn Ala Gly  Ala Arg Val Cys Leu  Ser Ile Thr
    1040                 1045                 1050

Ser Thr  Gly Thr Gly Thr Leu  Ser Ala His Asn Lys  Asp Gly Ser
    1055                 1060                 1065

Leu His  Ile Val Leu Pro Ser  Glu Asn Gly Thr Lys  Asp Gln Cys
    1070                 1075                 1080

Gln Ile  Leu His Phe Thr Ile  Pro Glu Val Glu Glu  Glu Phe Met
    1085                 1090                 1095

Tyr Ser  Cys Asp Gly Asp Glu  Arg Pro Leu Leu Val  Lys Gly Thr
    1100                 1105                 1110

Leu Ile  Val Ile Asp Pro Phe  Asp Asp Arg Arg Glu  Ala Gly Gly
    1115                 1120                 1125

Glu Ser  Thr Val Val Asn Pro  Lys Ser Gly Ser Trp  Asn Phe Phe
    1130                 1135                 1140

Asp Trp  Phe Ser Gly Leu Met  Ser Trp Phe Gly Gly  Pro Leu Lys
    1145                 1150                 1155
```

-continued

```
Thr Ile  Leu Leu Ile Cys Leu  Tyr Val Ala Leu Ser  Ile Gly Leu
    1160            1165            1170

Phe Phe  Leu Leu Ile Tyr Leu  Gly Lys Thr Gly Leu  Ser Lys Met
    1175            1180            1185

Trp Leu  Ala Ala Thr Lys Lys  Ala Ser
    1190            1195
```

```
<210> SEQ ID NO 6
<211> LENGTH: 265
<212> TYPE: PRT
<213> ORGANISM: Artificial Sequence
<220> FEATURE:
<223> OTHER INFORMATION: FMH-P8 RVFV NSs protein
<220> FEATURE:
<221> NAME/KEY: MUTAGEN
<222> LOCATION: (52)..(52)
<223> OTHER INFORMATION: Ile
<220> FEATURE:
<221> NAME/KEY: MUTAGEN
<222> LOCATION: (82)..(82)
<223> OTHER INFORMATION: Leu

<400> SEQUENCE: 6
```

```
Met Asp Tyr Phe Pro Val Ile Ser Val Asp Leu Gln Ser Gly Arg Arg
1                5               10              15

Val Val Ser Val Glu Tyr Ile Arg Gly Asp Gly Pro Pro Arg Ile Pro
            20              25              30

Tyr Ser Met Val Gly Pro Cys Cys Val Phe Leu Met His His Arg Pro
        35              40              45

Ser His Glu Ile Arg Leu Arg Phe Ser Asp Phe Tyr Asn Val Gly Glu
    50              55              60

Phe Pro Tyr Arg Val Gly Leu Gly Asp Phe Val Ser Asn Val Ala Pro
65              70              75              80

Pro Leu Ala Lys Pro Phe Gln Arg Leu Ile Asp Leu Ile Gly His Met
            85              90              95

Thr Leu Ser Asp Phe Thr Arg Phe Pro Asn Leu Lys Glu Ala Ile Ser
        100             105             110

Trp Pro Leu Gly Glu Pro Ser Leu Ala Phe Phe Asp Leu Ser Ser Thr
        115             120             125

Arg Val His Arg Ser Asp Asp Ile Arg Arg Asp Gln Ile Ala Thr Leu
    130             135             140

Ala Met Arg Ser Cys Lys Ile Thr Asn Asp Leu Glu Asp Ser Phe Val
145             150             155             160

Gly Leu His Arg Met Ile Val Thr Glu Ala Ile Leu Arg Gly Ile Asp
            165             170             175

Leu Cys Leu Leu Pro Gly Phe Asp Leu Met Tyr Glu Val Ala His Val
        180             185             190

Gln Cys Val Arg Leu Leu Gln Ala Ala Arg Glu Asp Ile Ser Asn Ala
        195             200             205

Val Val Pro Asn Ser Ala Leu Ile Ala Leu Met Glu Glu Ser Leu Met
    210             215             220

Leu Arg Ser Ser Leu Pro Ser Met Met Gly Arg Asn Asn Trp Val Pro
225             230             235             240

Val Val Pro Pro Ile Pro Asp Val Glu Ile Glu Ser Glu Glu Glu Ser
            245             250             255

Asp Asp Asp Gly Phe Val Glu Val Asp
            260             265
```

```
<210> SEQ ID NO 7
<211> LENGTH: 245
<212> TYPE: PRT
<213> ORGANISM: Artificial Sequence
<220> FEATURE:
<223> OTHER INFORMATION: FMH-P8 RVFV N protein

<400> SEQUENCE: 7

Met Asp Asn Tyr Gln Glu Leu Ala Ile Gln Phe Ala Ala Gln Ala Val
1               5                   10                  15

Asp Arg Asn Glu Ile Glu Gln Trp Val Arg Glu Phe Ala Tyr Gln Gly
            20                  25                  30

Phe Asp Ala Arg Arg Val Ile Glu Leu Leu Lys Gln Tyr Gly Gly Ala
        35                  40                  45

Gly Trp Glu Lys Asp Ala Lys Lys Met Ile Val Leu Ala Leu Thr Arg
    50                  55                  60

Gly Asn Lys Pro Arg Arg Met Met Met Lys Met Ser Lys Glu Gly Lys
65                  70                  75                  80

Ala Thr Val Glu Ala Leu Ile Asn Lys Tyr Lys Leu Lys Glu Gly Asn
                85                  90                  95

Pro Ser Arg Asp Glu Leu Thr Leu Ser Arg Val Ala Ala Ala Leu Ala
            100                 105                 110

Gly Trp Thr Cys Gln Ala Leu Val Val Leu Ser Glu Trp Leu Pro Val
        115                 120                 125

Thr Gly Thr Thr Met Asp Gly Leu Ser Pro Ala Tyr Pro Arg His Met
    130                 135                 140

Met His Pro Ser Phe Ala Gly Met Val Asp Pro Ser Leu Pro Glu Asp
145                 150                 155                 160

Tyr Leu Arg Ala Ile Leu Asp Ala His Ser Leu Tyr Leu Leu Gln Phe
                165                 170                 175

Ser Arg Val Ile Asn Pro Asn Leu Arg Gly Arg Thr Lys Glu Glu Val
            180                 185                 190

Ala Ala Thr Phe Thr Gln Pro Met Asn Ala Ala Val Asn Ser Asn Phe
        195                 200                 205

Ile Ser His Glu Lys Arg Arg Glu Phe Leu Lys Ala Phe Gly Leu Val
    210                 215                 220

Asp Ser Asn Gly Lys Pro Ser Ala Ala Val Met Ala Ala Ala Gln Ala
225                 230                 235                 240

Tyr Lys Thr Ala Ala
                245

<210> SEQ ID NO 8
<211> LENGTH: 30
<212> TYPE: DNA
<213> ORGANISM: Artificial Sequence
<220> FEATURE:
<223> OTHER INFORMATION: 5' end L segment primer

<400> SEQUENCE: 8
acacaaaggc gcccaatcat ggattctata                                      30

<210> SEQ ID NO 9
<211> LENGTH: 17
<212> TYPE: DNA
<213> ORGANISM: Artificial Sequence
<220> FEATURE:
<223> OTHER INFORMATION: 716F primer

<400> SEQUENCE: 9
```

-continued

```
cagtcacaga atctgtg                                               17

<210> SEQ ID NO 10
<211> LENGTH: 17
<212> TYPE: DNA
<213> ORGANISM: Artificial Sequence
<220> FEATURE:
<223> OTHER INFORMATION: L-F segment 1028ag primer

<400> SEQUENCE: 10
atggcaaaga tctgtgc                                               17

<210> SEQ ID NO 11
<211> LENGTH: 20
<212> TYPE: DNA
<213> ORGANISM: Artificial Sequence
<220> FEATURE:
<223> OTHER INFORMATION: L-R 2300g primer

<400> SEQUENCE: 11
aagtaaccat tgtaacaaca                                            20

<210> SEQ ID NO 12
<211> LENGTH: 23
<212> TYPE: DNA
<213> ORGANISM: Artificial Sequence
<220> FEATURE:
<223> OTHER INFORMATION: RdRp central-F primer

<400> SEQUENCE: 12
gctatccaga agtttgagga ttg                                        23

<210> SEQ ID NO 13
<211> LENGTH: 23
<212> TYPE: DNA
<213> ORGANISM: Artificial Sequence
<220> FEATURE:
<223> OTHER INFORMATION: L-F segment primer

<400> SEQUENCE: 13
ttctttgctt ctgataccct ctg                                        23

<210> SEQ ID NO 14
<211> LENGTH: 23
<212> TYPE: DNA
<213> ORGANISM: Artificial Sequence
<220> FEATURE:
<223> OTHER INFORMATION: L-R segment primer

<400> SEQUENCE: 14
gttccacttc cttgcatcat ctg                                        23

<210> SEQ ID NO 15
<211> LENGTH: 23
<212> TYPE: DNA
<213> ORGANISM: Artificial Sequence
<220> FEATURE:
<223> OTHER INFORMATION: Central-R RdRp primer

<400> SEQUENCE: 15
ctgatttgca gaagctatat gct                                        23

<210> SEQ ID NO 16
<211> LENGTH: 17
<212> TYPE: DNA
<213> ORGANISM: Artificial Sequence
```

-continued

```
<220> FEATURE:
<223> OTHER INFORMATION: 3817 F primer

<400> SEQUENCE: 16
gagtataaga aggcagt                                                      17

<210> SEQ ID NO 17
<211> LENGTH: 17
<212> TYPE: DNA
<213> ORGANISM: Artificial Sequence
<220> FEATURE:
<223> OTHER INFORMATION: 4553 F primer

<400> SEQUENCE: 17
tcactatctt taatgag                                                      17

<210> SEQ ID NO 18
<211> LENGTH: 23
<212> TYPE: DNA
<213> ORGANISM: Artificial Sequence
<220> FEATURE:
<223> OTHER INFORMATION: 5455 F primer

<400> SEQUENCE: 18
ccatttggat gcccagttta tat                                               23

<210> SEQ ID NO 19
<211> LENGTH: 17
<212> TYPE: DNA
<213> ORGANISM: Artificial Sequence
<220> FEATURE:
<223> OTHER INFORMATION: R 5583 primer

<400> SEQUENCE: 19
ctgatgagaa tggtgct                                                      17

<210> SEQ ID NO 20
<211> LENGTH: 25
<212> TYPE: DNA
<213> ORGANISM: Artificial Sequence
<220> FEATURE:
<223> OTHER INFORMATION: Q3'25nts primer

<400> SEQUENCE: 20
ttgtagcact atgctagtat cagaa                                             25

<210> SEQ ID NO 21
<211> LENGTH: 17
<212> TYPE: DNA
<213> ORGANISM: Artificial Sequence
<220> FEATURE:
<223> OTHER INFORMATION: L-segment end q3'R primer

<400> SEQUENCE: 21
ttgtagcact atgctag                                                      17

<210> SEQ ID NO 22
<211> LENGTH: 27
<212> TYPE: DNA
<213> ORGANISM: Artificial Sequence
<220> FEATURE:
<223> OTHER INFORMATION: (-2)Rtsm1 primer

<400> SEQUENCE: 22
gttttattaa caattctaac ctcggtt                                           27
```

<210> SEQ ID NO 23
<211> LENGTH: 19
<212> TYPE: DNA
<213> ORGANISM: Artificial Sequence
<220> FEATURE:
<223> OTHER INFORMATION: MRV1ag primer

<400> SEQUENCE: 23
caaatgacta ccagtcagc                                                  19

<210> SEQ ID NO 24
<211> LENGTH: 24
<212> TYPE: DNA
<213> ORGANISM: Artificial Sequence
<220> FEATURE:
<223> OTHER INFORMATION: RTsm2 primer

<400> SEQUENCE: 24
caagtgaaca gggaaatagg atgg                                            24

<210> SEQ ID NO 25
<211> LENGTH: 24
<212> TYPE: DNA
<213> ORGANISM: Artificial Sequence
<220> FEATURE:
<223> OTHER INFORMATION: Sm2 primer

<400> SEQUENCE: 25
gaacatgctg atgcatatga gaca                                            24

<210> SEQ ID NO 26
<211> LENGTH: 24
<212> TYPE: DNA
<213> ORGANISM: Artificial Sequence
<220> FEATURE:
<223> OTHER INFORMATION: Sm3 primer

<400> SEQUENCE: 26
gacccatcct tattgtgggc agag                                            24

<210> SEQ ID NO 27
<211> LENGTH: 22
<212> TYPE: DNA
<213> ORGANISM: Artificial Sequence
<220> FEATURE:
<223> OTHER INFORMATION: Sm4 primer

<400> SEQUENCE: 27
atctggcaaa agacgattac gc                                              22

<210> SEQ ID NO 28
<211> LENGTH: 18
<212> TYPE: DNA
<213> ORGANISM: Artificial Sequence
<220> FEATURE:
<223> OTHER INFORMATION: EM-RVFV-R primer

<400> SEQUENCE: 28
cacaaagacc ggtgcaac                                                   18

<210> SEQ ID NO 29
<211> LENGTH: 20
<212> TYPE: DNA
<213> ORGANISM: Artificial Sequence
<220> FEATURE:
<223> OTHER INFORMATION: EM-RVFV-F primer

<400> SEQUENCE: 29
gaatcaacag ttgtgaatcc                                              20

<210> SEQ ID NO 30
<211> LENGTH: 19
<212> TYPE: DNA
<213> ORGANISM: Artificial Sequence
<220> FEATURE:
<223> OTHER INFORMATION: NS0g primer

<400> SEQUENCE: 30
acacaaagac cccctagtg                                               19

<210> SEQ ID NO 31
<211> LENGTH: 20
<212> TYPE: DNA
<213> ORGANISM: Artificial Sequence
<220> FEATURE:
<223> OTHER INFORMATION: NS2g primer

<400> SEQUENCE: 31
tgatttgcag agtggtcgtc                                              20

<210> SEQ ID NO 32
<211> LENGTH: 22
<212> TYPE: DNA
<213> ORGANISM: Artificial Sequence
<220> FEATURE:
<223> OTHER INFORMATION: R-S primer

<400> SEQUENCE: 32
cggacttgga gactttgcat ca                                           22

<210> SEQ ID NO 33
<211> LENGTH: 24
<212> TYPE: DNA
<213> ORGANISM: Artificial Sequence
<220> FEATURE:
<223> OTHER INFORMATION: F-S primer

<400> SEQUENCE: 33
ttctttcaga ttggggaacc ttgt                                         24

<210> SEQ ID NO 34
<211> LENGTH: 18
<212> TYPE: DNA
<213> ORGANISM: Artificial Sequence
<220> FEATURE:
<223> OTHER INFORMATION: NScag primer

<400> SEQUENCE: 34
ccttaacctc taatcaac                                                18

<210> SEQ ID NO 35
<211> LENGTH: 23
<212> TYPE: DNA
<213> ORGANISM: Artificial Sequence
<220> FEATURE:
<223> OTHER INFORMATION: SS1 primer

<400> SEQUENCE: 35
agccacttag gctgctgtct tgt                                          23

<210> SEQ ID NO 36

-continued

```
<211> LENGTH: 30
<212> TYPE: DNA
<213> ORGANISM: Artificial Sequence
<220> FEATURE:
<223> OTHER INFORMATION: RTss1 primer

<400> SEQUENCE: 36
ctattacaat aatggacaac tatcaagagc                                    30

<210> SEQ ID NO 37
<211> LENGTH: 21
<212> TYPE: DNA
<213> ORGANISM: Artificial Sequence
<220> FEATURE:
<223> OTHER INFORMATION: NP0ag primer

<400> SEQUENCE: 37
acacaaagct ccctagagat a                                             21

<210> SEQ ID NO 38
<211> LENGTH: 18
<212> TYPE: DNA
<213> ORGANISM: Artificial Sequence
<220> FEATURE:
<223> OTHER INFORMATION: LsegcARN primer

<400> SEQUENCE: 38
agttttgata atcatgtc                                                 18

<210> SEQ ID NO 39
<211> LENGTH: 16
<212> TYPE: DNA
<213> ORGANISM: Artificial Sequence
<220> FEATURE:
<223> OTHER INFORMATION: LsegvARN primer

<400> SEQUENCE: 39
cttttgatac atctga                                                   16

<210> SEQ ID NO 40
<211> LENGTH: 17
<212> TYPE: DNA
<213> ORGANISM: Artificial Sequence
<220> FEATURE:
<223> OTHER INFORMATION: MsegcARN primer

<400> SEQUENCE: 40
gtttctctcc ctatttg                                                  17

<210> SEQ ID NO 41
<211> LENGTH: 18
<212> TYPE: DNA
<213> ORGANISM: Artificial Sequence
<220> FEATURE:
<223> OTHER INFORMATION: MsegvARN primer

<400> SEQUENCE: 41
tcctccttat atatcttg                                                 18

<210> SEQ ID NO 42
<211> LENGTH: 18
<212> TYPE: DNA
<213> ORGANISM: Artificial Sequence
<220> FEATURE:
<223> OTHER INFORMATION: SsegcARN primer

<400> SEQUENCE: 42
```

-continued

```
tattagatca ataagtct                                                 18

<210> SEQ ID NO 43
<211> LENGTH: 17
<212> TYPE: DNA
<213> ORGANISM: Artificial Sequence
<220> FEATURE:
<223> OTHER INFORMATION: SsegvARN primer

<400> SEQUENCE: 43
tctttcgaca ttttcat                                                  17

<210> SEQ ID NO 44
<211> LENGTH: 6404
<212> TYPE: DNA
<213> ORGANISM: Artificial Sequence
<220> FEATURE:
<223> OTHER INFORMATION: RVFV 56/74 L segment
<220> FEATURE:
<221> NAME/KEY: gene
<222> LOCATION: (19)..(6297)
<223> OTHER INFORMATION: RVFV 56/74 L segment open reading frame

<400> SEQUENCE: 44
acacaaaggc gcccaatcat ggattctata ttatcaaaac agctggttga caagactggt      60
tttgttagag tgccaatcaa gcattatgac tgtacaatgc taactctggc actcccaaca     120
tttgatgtct ccaagatggt agatagaatt accatagact tcaatttaga cgacatacaa     180
ggagcatctg aaataggctc aactttgcta ccctctatgt cgatagatgt ggaagatatg     240
gccaattttg ttcacgattt caccttggc cacttagctg acaagactga cagactctta     300
atgcgtgagt ttcccatgat gaatgacggg tttgatcatc tgagccctga catgattatc     360
aaaactacat ctggcatgta taacatcgtt gagttcacca ccttaggggg ggatgaaaga     420
ggtgcattcc aggctgccat gactaaactc gctaagtatg aggttccttg tgagaacaga     480
tctcagggca ggactgttgt tctttatgtt gttagcgcct accggcatgg tgtttggtct     540
aatttggagc tagaggactc tgaagcagag gagatggtat ataggtacag acttgccctt     600
agtgtgatgg atgagctaag gaccttgttc ccagaactgt catccacaga tgaggaacta     660
ggaaagactg agagagagtt gctagccatg gtctcctcca tccaaataaa ttggtcagtc     720
acagaatctg tgtttcctcc ctttagcaga gaaatgtttg acaggttcag atcttctcct     780
cccgattcag agtacatcac gaggatagtg agcagatgcc tcataaattc tcaagagaaa     840
ctcatcaata attccttctt tgctgaaggg aatgataaag ttttgagatt ttcaaaaaac     900
gctgaggagt gttccttggc aatagagaga gctttaaatc agtatagggc agaagacaac     960
cttagggacc tcaatgacca caagtctact attcagctgc cccctggct gtcctatcac    1020 gatgccgatg gcaaagatct gtgccctctt cagggattag atgtgagagg agaccatccc    1080
atgtgcaacc tgtggagaga agtggttacc tctgcaaatc tagaggagat tgagaggatg    1140
cacgatgatg cagcggcaga acttgagttt gccctttcag gggtgaagga caggccagat    1200
gaaagaaaca gataccatag agtccatctg aatatggact cagatgatag tgtctacata    1260
gctgctttag gggttaatgg aaagaagcat aaagcagaca cattagtgca acaaatgaga    1320
gacaggagca aacagccctt ctctccagat catgatgtgg atcacatatc tgaatttctc    1380
tctgcatgct ctagtgactt gtgggcaaca gatgaggacc tatacaaccc tctctcttgt    1440
gataaagagc ttagattggc agctcagaga attcatcagc catccttatc agaaaggggc    1500
```

-continued

```
ttcaatgaga ttataacaga gcactacaga tttatgggaa gtaggatagg atcatggtgc   1560
caaatggtca gtttaatagg agctgagcta tcagcttctg taaagcaaca tgttaagcct   1620
aactattttg tgattaaacg actactaggt tctgggattt tcttgctgat caagcctact   1680
tccagcaaaa gccatatatt cgtgtctttt gcaattaagc gctcttgctg ggcctttgat   1740
ctctccactt ccagggtttt caaaccctac atagatgccg gggatctgtt agttactgac   1800
tttgtttctt acaaactaag taagcttacc aacctctgca agtgcgtttc gttaatggaa   1860
tcctccttct cattttgggc agaggcattt gggattccaa gctggaactt tgttagtgac   1920
ttgttcaggt cttcagactc tgcagcaatg gatgcctcat acatgggcaa actctcttta   1980
ttaacccttt tggaagacaa agcaacaact gaagagttac agactattgc aagatatata   2040
atcatggagg gctttgtctc gcccccagaa atcccaaaac ctcacaagat gacctctaag   2100
tttcccaagg ttctcaggtc agagctgcag gtttacttat taaactgctt atgcagaact   2160
atccagagaa tagcaggtga gccctttatt cttaagaaga aggatgggtc tatatcctgg   2220
ggtggcatgt ttaatccttt ttcagggcgt ccactgcttg atatgcaacc actcatcagc   2280
tgttgttaca atggttactt taaaaacaaa gaagaagaga ctgagccttc ctcccttct    2340 gggatgtata agaaaattat agaacttgag caccttagac cacagtcaga tgccttcttg   2400
ggttataaag atccagaact acctagaatg catgagttca gtgtttccta cttgaaggag   2460
gcttgcaatc atgctaagct ggtcttaagg agtctctatg gacagaattt catggagcaa   2520
atagacaacc aaattattcg agagctcagt gggttgactc tagaaagatt agccacactt   2580
aaggccacaa gcaactttaa tgagaattgg tatgtctata aggatgtggc agacaagaac   2640
tacacaaggg ataaattatt agtgaagatg tcaaaatatg cttctgaggg aaagagccta   2700
gctatccaga agtttgagga ttgcatgagg cagatagagt cacaaggatg tatgcacatt   2760
tgtttgttta agaaacaaca gcatggaggt ctgagagaga tctatgtgat gggtgcagag   2820
gaaagaattg ttcaatcggt ggtggagaca atagccaggt ctataggaa gttctttgct    2880 tctgataccc tctgtaaccc ccccaataag gtgaaaattc ctgagacaca tggcattagg   2940
gctcggaagc aatgtaaggg gcctgtgtgg acttgtgcaa catcagatga tgcaaggaag   3000
tggaaccaag gccattttgt tacaaagttt gccctcatgc tatgtgagtt cacctctcct   3060
aagtggtggc cattgatcat tagggatgt tcaatgttta ccaggaaaag gatgatgatg    3120
aatttgaatt atcttaagat cctggatggt catcgagagc ttgatattag agatgacttt   3180
gtgatggatc tcttcaaagc ttatcatggt gaggcagaag ttccatgggc ttttaagggt   3240
aaaacatatc tggaaaccac aacagggatg atgcagggga tattgcatta tacttcctca   3300 ttattcacaca ccattcatca agaatacatc cggtccttgt cctttaaaat attcaacctg   3360
aaggttgctc ctgagatgag caaaagcctg gtttgtgaca tgatgcaagg atcagatgat   3420
agtagcatgc taatcagctt cccagctgat gacgagaagg ttctcaccag atgcaaagtg   3480
gccgcagcca tatgcttccg aatgaagaag gagctgggag tgtaccttgc catctacccc   3540
tcagagaagt ccacagcaaa cacagatttt gtgatggagt acaattctga attttatttc   3600
cacacccagc atgttagacc gacgatcagg tggattgcag catgttgcag cctgccagaa   3660
gtggaaacac tagtagcccg ccaggaagag gcctctaatc taatgacttc agttactgag   3720
gggggtgggt cattctcctt agctgcaatg attcagcaag ctcagtgcac tctccattac   3780
atgctaatgg gcatgggagt gtctgagcta ttccttagagt ataagaaggc agtgctgaag   3840
tggaatgacc ctggtctggg tttcttcctg cttgacaatc cttatgcgtg cgggttggga   3900
```

-continued

```
ggttttagat ttaatctctt caaagccatc accagaactg atttgcagaa gctatatgct      3960
ttcttcatga agaaggttaa gggctcagct gctagggact gggcagatga ggatgttacc      4020
atcccagaaa cgtgtagcgt gagcccaggt ggcgctctaa ttcttagctc ctctctaaag      4080
tggggatcta ggaagaagtt tcagaaactg agagaccgtt tgaacatacc agagaactgg      4140
attgagctaa taaatgagaa tccagaggtg ctctatcgag ctcccagaac aggcccagaa      4200
atattgttgc gcattgcaga gaaagtccat agccctggtg ttgtgtcatc attgtcttct      4260
ggcaatgcag tctgtaaagt catggcctca gctgtatact tcttatcagc aacaattttt      4320
gaagacactg gacgccctga gttcaacttc ttagaggatt ccaagtacag cttgctacaa      4380
aagatggccg catattctgg ctttcatggt ttcaatgata tggagccaga agatatatta      4440
ttcctattcc cgaacattga ggaattagaa tcactggatt ctatagttta caacaaggga      4500
gaaatagaca tcatcccaag agttaatatc agggatgcaa cccaaaccag ggtcactatc      4560
tttaatgagc agaagaccct ccgaacatct ccagagaagt tggtgtcaga caagtggttc      4620
gggactcaga agagtaggat aggcaaaaca actttcctgg ctgaatggga gaagctaaag      4680
aaaattgtga agtggttgga agacactcca gaagcaactc tagctcacac tccactgaat      4740
aaccatattc aggttaggaa tttctttgct agaatggaaa gcaagcctag aacggttaga      4800
ataacaggag ctcctgtaaa gaagaggtca ggggttagca agatagctat ggttatccgt      4860
gacaatttct cccggatggg ccatcttaga ggtgtagaag acctcgctgg cttcactcgt      4920
agtgtgtcag ctgaaatcct caagcacttt ctgttctgca tactacaggg tccatacagt      4980
gagagctata agctacagct aatctacaga gtcctaagct cagtgtcaaa cgttgagata      5040
aaggaatcgg atggtaagac aaaaaccaat ttgattggga tccttcagag atttctagat      5100
ggtgatcacg ttgtccctat aattgaagag atgggagccg gaacagtggg tggattcatc      5160
aagagacaac agtctaaggt tgtgcaaaat aaagtggtct attatggagt tgggatctgg      5220
agaggcttca tggatggata tcaggtccat cttgagatag aaaatgacat aggacagccc      5280
ccaaggctta ggaatgtcac aactaactgt cagagcagcc catgggatct gagtgtccca      5340
ataaggcagt gggcagaaga catggggggtc acaaacaacc aggattattc ctctaaatct      5400
agcagaggag ctagatattg gatgcattca tttaggatgc aaggaccag caagccattt       5460 ggatgcccag tttatattat taagggtgac atgtcagatg ttatcagact gagaaaagag      5520
gaggtggaga tgaaagtacg gggctctact ctcaacttgt acactaagca ccattctcat      5580
caagacttac acattttatc ttacactgca tcagacaatg atctcagtcc aggcatttttc      5640 aagtcaatat cagatgaggg agtggctcaa gccctgcagt tatttgagag ggagccaagc      5700
aactgctggg tgagatgtga gtctgtagct ccaaaattca tatcagccat ccttgagata      5760
tgtgagggga gagacagat aaaaggaatc aacagaacca gactctcaga gattgtgaga       5820
atttgttctg aatcttccct aagatcaaag gtcggatcta tgttctcatt tgtcgccaat      5880
gttgaggagg cccatgatgt tgattatgat gcgttaatgg atctaatgat agaagatgct      5940
aagaacaatg cattcagtca tgttgtcgat tgcatagagt tggatgttaa tggtccttac      6000
gagatggagt cttttgatac atctgatgtc aacctctttg gccagcccca ttacaaggac      6060
atcagttcat tatctatgat tgctcatccc ttaatggata gtttgttga ttatgccatt        6120 tccaagatgg ggagagcctc agttagaaaa gttctagaga caggtcggtg ctctagcaaa      6180
gactatgatt tatcaaaggt tctcttcaga actctacaga gaccagaaga gagcattagg      6240
```

```
atagatgatc tggagttata tgaggagaca gatgtggcgg atgacatgct aggctaagac      6300
caataagcaa agtcaggctt agatttaggg atactacgct agtattggaa tccatgtggg      6360
ttctgatact agcatagtgc tacaatattg ggcggtcttt gtgt                      6404
```

```
<210> SEQ ID NO 45
<211> LENGTH: 3885
<212> TYPE: DNA
<213> ORGANISM: Artificial Sequence
<220> FEATURE:
<223> OTHER INFORMATION: RVFV 56/74 M segment
<220> FEATURE:
<221> NAME/KEY: gene
<222> LOCATION: (21)..(3614)
<223> OTHER INFORMATION: RVFV 56/74 gene encoding M (poly)protein

<400> SEQUENCE: 45
```

```
acacaaagac ggtgcattaa atgtatgttt tactaacaat tctgatcacg gttctggtgt       60
gtgaagcggt tattagagtg tctctaagct ccacaagaga agagacctgt tttggtgact      120
ccaccaaccc agagatgatt gaaggagctt gggattcact cagagaggag gagatgccag      180
aggagctctc ctgttctata tcaggcataa gggaggttaa gacctcaagc caggagttat      240
acagggcatt aaaagccatc attgctgctg atggcttgaa caacatcacc tgccatggta      300
aggatcctga ggacaagatt tctctcataa agggtcctcc tcacaaaaag cgggtgggga      360
tagttcggtg tgagagacga agagatgcta agcaaatagg gagagaaacc atggcaggga      420
ttgcaatgac agtccttcca gccttagcag ttttttgcttt ggcacctgtt gtttttgctg      480 aagacccccca tctcaggaac agaccaggga aggggcacaa ctacattgac gggatgactc      540
aggaggatgc cacatgcaaa cctgtgacat atgctggggc atgtagcagt tttgatgtct      600
tgcttgaaaa ggggaaattt cccctttttcc agtcgtatgc tcatcataga actctactgg      660
aagcagttca cgacactatc attgcaaagg ctgatccacc tagctgtgac cttcagagtg      720
ctcatgggaa tccctgcatg aaaagagaaac tcgtgatgaa gacacactgt ccaaatgact      780
accagtcagc tcattacctc aacaatgacg ggaaagtggc ttcagtcaag tgccctccta      840
agtatgagct cactgaggac tgcaacttttt gtaggcagat gacaggtgct agcctgaaga      900
aagggtctta tcctctccaa gacttatttt gtcagtcaag tgaggatgat ggatcaaaat      960
taaaaacaaa aatgaaaggg gtctgcgaag tggggggttca agcactcaaa aagtgtgatg     1020
gccaactcag cactgcacat gaggttgtgc cctttgcagt gtttaagaac tcaaagaaag     1080
tttatcttga taagcttgac ctcaaaactg aggagaatct gctaccagac tcatttgtct     1140
gcttcgagca taagggacag tataaaggaa caatggactc tggtcagact aagagggagc     1200
tcaaaagctc tgatatctct cagtgcccca agattggagg acatggtagt aaaaagtgca     1260 ctgggggacgc agcattttgc tctgcttatg agtgcactgc tcagtacgcc aatgcctact     1320
gttcacatgc taatggttca gggattgtgc agatacaagt atcaggggtc tggaagaagc     1380
ctttatgtgt agggtatgag agagtggttg tgaagagaga actctctgcc aagcccatcc     1440
agagagttga gccctgcaca acttgtataa ccaaatgtga gcctcatgga ttggttgtcc     1500
gatcaacagg gttcaagata tcatctgcag ttgcttgtgc tagcggagtt tgcgtcacag     1560
gatcgcagag tccttctacc gagattacac tcaagtatcc agggatatcc agtcctctg      1620 gggggacat aggggttcac atggcacatg atgatcagtc agttagctcc aaaaatagtag     1680 ctcactgccc ccccccaggac ccgtgcttag tgcatggctg catagtgtgt gctcatggcc     1740
tgataaatta ccagtgtcac actgctctca gtgcctttgt tgttgtgttt gtattcagtt     1800
```

```
ctattgcaat aacttgttta gctattcttt atagggtgct caagtgccta aagattgccc   1860
caaggaaggt tctaaatcca ctaatgtgga ttacagcctt catcagatgg gtgtataaga   1920
agatggttgc tagagtggca gacaatatta atcaagtgaa cagggaaata ggatggatgg   1980 aaggggggtca gttggttcta gggaaccctg cccctattcc tcgtcatgcc ccaatcccac   2040
gttatagcac atacctaatg ctactattga ttgtctcata tgcatcagca tgttcagaac   2100
tgattcaggc aagctccaga atcaccactt gctccacaga gggtgttaac accaagtgta   2160
gactgtctgg cacagcattg atcagggcag ggtcagttgg ggcagaggct tgtttaatgt   2220 tgaaggggggt caaggaagat caaaccaaat tcttgaagat aaaaactgtc tcaagtgagc   2280
tatcgtgcag ggagggccag agctattgga ctgggtcctt tagcccccaaa tgtctgagct   2340 caaggagatg ccatcttgtt ggagaatgtc atgtgaatag gtgtctgtct tggagggggaca   2400 atgaaacttc agcagagttt tcatttgttg gggaaagcac gaccatgcga gagaataagt   2460
gttttgagca gtgtggggagga tgggggtgtg ggtgcttcaa tgtgaaccca tcttgcttat   2520
ttgtgcacac gtacctgcag tcagttagaa aagaggccct tagagttttt aactgtatcg   2580
actgggtgca taaactcagt ctagagatca cagactttga tggctctgtt tcaacaatag   2640
acttgggagc atcatctagc cgtttcacaa actggggttc agttagcctc tcactggacg   2700
cagagggtat ttcaggctca aatagctttt ctttcattga gagcccaggc aaagggtatg   2760
caattgttga tgagccattc tcagaaattc ctcggcaagg gttcttgggg gagatcaggt   2820
gtaattcaga gtcctcagtc ctgagtgctc atgaatcatg ccttagggca ccaaacctta   2880
tctcatacaa gcccatgata gatcaattgg agtgcacaac aaatctgatt gatcctttg   2940 ttgtctttga gaggggttct ctgccacaga caaggaatga aaaaaccttt gcagcttcaa   3000
aaggaaatag gggtgttcaa gctttctcta agggctctgt acaagctgat ctaactctga   3060
tgtttgacaa ttttgaggtg gactttgtgg gagcagccgt atcttgtgat gccgccttct   3120
taaacttgac aggttgctat tcttgcaatg cgggagccag ggtctgcctg tctatcacat   3180
ccacaggaac tggaactctc tctgcccaca ataaggatgg gtctctgcac atagttcttc   3240
catcagagaa tggaacaaaa gatcagtgtc agatactaca cttcactgta cctgaagtag   3300
aggaggagtt tatgtactct tgtgatggag atgagcggcc tctgttggtg aaagggaccc   3360
tgatagctat tgatccattt gatgataggc gggaagcagg gggggaatca acagttgtga   3420
atccaaaatc tggatcttgg aatttctttg actggttttc tggactcatg agttggtttg   3480
gagggcctct taaaactata ctcctcattt gcctgtatgt tgcattatca attgggctct   3540
ttttcctcct tatatatctt ggaagaacag gcctctctaa aatgtggctt gctgctacta   3600
agaaggcctc atagatcagt acgtgtagaa gcaatatgta gaaacaagtg gacataagca   3660
aacctaatta tgtaaatatt gtacagatag gtcaaattat tgggatatcc aagcttagat   3720
gcttatgcaa tattactttt gatgtaagct tagttgtaat ttggggtggt gggggtgaggc   3780 agcagcagtc tcaagtgctt gtgaatattc tagttggcgt aattgtcttt tgccagatta   3840
gctgggaatt aaactaactc tttgaagttg caccggtctt tgtgt             3885
```

```
<210> SEQ ID NO 46
<211> LENGTH: 1691
<212> TYPE: DNA
<213> ORGANISM: Artificial Sequence
<220> FEATURE:
<223> OTHER INFORMATION: RVFV 56/74 S segment
<220> FEATURE:
```

```
<221> NAME/KEY: gene
<222> LOCATION: (35)..(832)
<223> OTHER INFORMATION: RVFV 56/74 gene encoding NSs protein
<220> FEATURE:
<221> NAME/KEY: gene
<222> LOCATION: (916)..(1653)
<223> OTHER INFORMATION: RVF virus gene encoding N protein 56/74

<400> SEQUENCE: 46
acacaaagac cccctagtgc ttatcaagtg tatcatggat tactttcctg tgatatctgt      60
tgatttgcag agtggtcgtc gtgttgtgtc agtggagtac attagaggtg atggtcctcc     120
caggatacct tattctatgg ttgggccctg ttgtgtcttt ctcatgcacc atcgtcctag     180
tcacgaggtt cgcttgcgat tctctgattt ctacaatgtc ggagaattcc cataccgagt     240
cggacttgga gactttgtat caaacgttgc acctccacca gcaaagcctt ttcagagact     300
tattgatcta ataggccata tgactcttag tgatttcaca aggttcccca atctgaaaga     360
agccatatcc tggcctcttg agaaccctcc cctggctttc tttgacctaa gctccaccag     420
agtgcatagg tctgatgata ttagaaggga ccagattgct actctagcaa tgaggagctg     480
caagattacc aatgatctgg aggactcctt tgttggctta cacaggatga tagtgaccga     540
ggctatcctc agagggattg acttgtgcct gttgccaggc tttgatctca tgtatgaggt     600
tgctcacgtt cagtgtgttc ggctcctgca ggcagcaaga gaggatattt ctaatgctgt     660
agttccaaac tcagctctca ttgctcttat ggaggagagc ttgatgctgc gctcatcact     720
ccctagcatg atggggagaa caactgggt tccagttgtt cctccaatcc cagatgttga     780
gatagaatca gaggaagaga gtgatgacga tggatttgtt gaggttgatt agagattaag     840
gctgccccac cccccacccc caatcccgac cgtaaccccca accacccct tttcccaaa     900 ccctgggca gccacttagg ctgctgtctt gtacgcctga gcagctgcca tgacagctgc     960
tgacggcttc ccattggaat ccacaagccc aaaagctttc aagaattctc tcctcttctc    1020
atggcttata aagttgctat tcactgctgc attcattggc tgcgtgaacg ttgcggcaac    1080
ctcctccttt gttctacctc ggaggtttgg gttgatgacc cgggagaact gcagcagata    1140
cagagagtga gcatccaata ttgcccttag atagtcttct ggtagagaag ggtccaccat    1200
gccagcaaag ctggggtgca tcatatgcct tgggtatgca ggggataggc catccatggt    1260
ggtcccagtg acaggaagcc actcactcaa gacgaccaaa gcctggcaag tccagccagc    1320
cagggcagca gcaactcgtg atagagtcaa ctcatcccgg gaaggattcc cctcctttag    1380
cttatacttg ttgatgagag cctccacagt tgctttgcct tctttcgaca tttttcatcat    1440 catcctccgg ggcttgttgc cacgagtcag agccagaaca atcattttct ggcatcctt     1500 ctcccagcca gccccaccat actgctttaa gagttcgata accctacggg catcaaatcc    1560
ttgataagca aactctcgga cccactgttc aatctcattg cggtccactg cttgagcagc    1620
aaactggatc gcaagctctt gatagttgtc cattattgta atagtgtttg tatctctagg    1680
gagctttgtg t                                                         1691

<210> SEQ ID NO 47
<211> LENGTH: 2092
<212> TYPE: PRT
<213> ORGANISM: Artificial Sequence
<220> FEATURE:
<223> OTHER INFORMATION: RVFV 56/74 L protein

<400> SEQUENCE: 47

Met Asp Ser Ile Leu Ser Lys Gln Leu Val Asp Lys Thr Gly Phe Val
```

-continued

```
1                 5                   10                  15

Arg Val Pro Ile Lys His Tyr Asp Cys Thr Met Leu Thr Leu Ala Leu
             20                  25                  30

Pro Thr Phe Asp Val Ser Lys Met Val Asp Arg Ile Thr Ile Asp Phe
             35                  40                  45

Asn Leu Asp Asp Ile Gln Gly Ala Ser Glu Ile Gly Ser Thr Leu Leu
         50                  55                  60

Pro Ser Met Ser Ile Asp Val Glu Asp Met Ala Asn Phe Val His Asp
65                  70                  75                  80

Phe Thr Phe Gly His Leu Ala Asp Lys Thr Asp Arg Leu Leu Met Arg
                 85                  90                  95

Glu Phe Pro Met Met Asn Asp Gly Phe Asp His Leu Ser Pro Asp Met
             100                 105                 110

Ile Ile Lys Thr Thr Ser Gly Met Tyr Asn Ile Val Glu Phe Thr Thr
             115                 120                 125

Phe Arg Gly Asp Glu Arg Gly Ala Phe Gln Ala Ala Met Thr Lys Leu
         130                 135                 140

Ala Lys Tyr Glu Val Pro Cys Glu Asn Arg Ser Gln Gly Arg Thr Val
145                 150                 155                 160

Val Leu Tyr Val Val Ser Ala Tyr Arg His Gly Val Trp Ser Asn Leu
                 165                 170                 175

Glu Leu Glu Asp Ser Glu Ala Glu Glu Met Val Tyr Arg Tyr Arg Leu
             180                 185                 190

Ala Leu Ser Val Met Asp Glu Leu Arg Thr Leu Phe Pro Glu Leu Ser
             195                 200                 205

Ser Thr Asp Glu Glu Leu Gly Lys Thr Glu Arg Glu Leu Leu Ala Met
         210                 215                 220

Val Ser Ser Ile Gln Ile Asn Trp Ser Val Thr Glu Ser Val Phe Pro
225                 230                 235                 240

Pro Phe Ser Arg Glu Met Phe Asp Arg Phe Arg Ser Ser Pro Pro Asp
             245                 250                 255

Ser Glu Tyr Ile Thr Arg Ile Val Ser Arg Cys Leu Ile Asn Ser Gln
             260                 265                 270

Glu Lys Leu Ile Asn Asn Ser Phe Phe Ala Glu Gly Asn Asp Lys Val
         275                 280                 285

Leu Arg Phe Ser Lys Asn Ala Glu Glu Cys Ser Leu Ala Ile Glu Arg
         290                 295                 300

Ala Leu Asn Gln Tyr Arg Ala Glu Asp Asn Leu Arg Asp Leu Asn Asp
305                 310                 315                 320

His Lys Ser Thr Ile Gln Leu Pro Pro Trp Leu Ser Tyr His Asp Ala
             325                 330                 335

Asp Gly Lys Asp Leu Cys Pro Leu Gln Gly Leu Asp Val Arg Gly Asp
             340                 345                 350

His Pro Met Cys Asn Leu Trp Arg Glu Val Val Thr Ser Ala Asn Leu
             355                 360                 365

Glu Glu Ile Glu Arg Met His Asp Asp Ala Ala Ala Glu Leu Glu Phe
         370                 375                 380

Ala Leu Ser Gly Val Lys Asp Arg Pro Asp Glu Arg Asn Arg Tyr His
385                 390                 395                 400

Arg Val His Leu Asn Met Asp Ser Asp Ser Val Tyr Ile Ala Ala
             405                 410                 415

Leu Gly Val Asn Gly Lys Lys His Lys Ala Asp Thr Leu Val Gln Gln
             420                 425                 430
```

```
Met Arg Asp Arg Ser Lys Gln Pro Phe Ser Pro Asp His Asp Val Asp
        435                 440                 445

His Ile Ser Glu Phe Leu Ser Ala Cys Ser Ser Asp Leu Trp Ala Thr
    450                 455                 460

Asp Glu Asp Leu Tyr Asn Pro Leu Ser Cys Asp Lys Glu Leu Arg Leu
465                 470                 475                 480

Ala Ala Gln Arg Ile His Gln Pro Ser Leu Ser Glu Arg Gly Phe Asn
                485                 490                 495

Glu Ile Ile Thr Glu His Tyr Arg Phe Met Gly Ser Arg Ile Gly Ser
                500                 505                 510

Trp Cys Gln Met Val Ser Leu Ile Gly Ala Glu Leu Ser Ala Ser Val
            515                 520                 525

Lys Gln His Val Lys Pro Asn Tyr Phe Val Ile Lys Arg Leu Leu Gly
    530                 535                 540

Ser Gly Ile Phe Leu Leu Ile Lys Pro Thr Ser Ser Lys Ser His Ile
545                 550                 555                 560

Phe Val Ser Phe Ala Ile Lys Arg Ser Cys Trp Ala Phe Asp Leu Ser
                565                 570                 575

Thr Ser Arg Val Phe Lys Pro Tyr Ile Asp Ala Gly Asp Leu Leu Val
            580                 585                 590

Thr Asp Phe Val Ser Tyr Lys Leu Ser Lys Leu Thr Asn Leu Cys Lys
            595                 600                 605

Cys Val Ser Leu Met Glu Ser Ser Phe Ser Phe Trp Ala Glu Ala Phe
    610                 615                 620

Gly Ile Pro Ser Trp Asn Phe Val Ser Asp Leu Phe Arg Ser Ser Asp
625                 630                 635                 640

Ser Ala Ala Met Asp Ala Ser Tyr Met Gly Lys Leu Ser Leu Leu Thr
                645                 650                 655

Leu Leu Glu Asp Lys Ala Thr Thr Glu Glu Leu Gln Thr Ile Ala Arg
            660                 665                 670

Tyr Ile Ile Met Glu Gly Phe Val Ser Pro Pro Glu Ile Pro Lys Pro
            675                 680                 685

His Lys Met Thr Ser Lys Phe Pro Lys Val Leu Arg Ser Glu Leu Gln
    690                 695                 700

Val Tyr Leu Leu Asn Cys Leu Cys Arg Thr Ile Gln Arg Ile Ala Gly
705                 710                 715                 720

Glu Pro Phe Ile Leu Lys Lys Lys Asp Gly Ser Ile Ser Trp Gly Gly
            725                 730                 735

Met Phe Asn Pro Phe Ser Gly Arg Pro Leu Leu Asp Met Gln Pro Leu
            740                 745                 750

Ile Ser Cys Cys Tyr Asn Gly Tyr Phe Lys Asn Lys Glu Glu Glu Thr
            755                 760                 765

Glu Pro Ser Ser Leu Ser Gly Met Tyr Lys Lys Ile Ile Glu Leu Glu
    770                 775                 780

His Leu Arg Pro Gln Ser Asp Ala Phe Leu Gly Tyr Lys Asp Pro Glu
785                 790                 795                 800

Leu Pro Arg Met His Glu Phe Ser Val Ser Tyr Leu Lys Glu Ala Cys
                805                 810                 815

Asn His Ala Lys Leu Val Leu Arg Ser Leu Tyr Gly Gln Asn Phe Met
            820                 825                 830

Glu Gln Ile Asp Asn Gln Ile Ile Arg Glu Leu Ser Gly Leu Thr Leu
            835                 840                 845
```

```
Glu Arg Leu Ala Thr Leu Lys Ala Thr Ser Asn Phe Asn Glu Asn Trp
    850                 855                 860

Tyr Val Tyr Lys Asp Val Ala Asp Lys Asn Tyr Thr Arg Asp Lys Leu
865                 870                 875                 880

Leu Val Lys Met Ser Lys Tyr Ala Ser Glu Gly Lys Ser Leu Ala Ile
                885                 890                 895

Gln Lys Phe Glu Asp Cys Met Arg Gln Ile Glu Ser Gln Gly Cys Met
                900                 905                 910

His Ile Cys Leu Phe Lys Lys Gln Gln His Gly Gly Leu Arg Glu Ile
            915                 920                 925

Tyr Val Met Gly Ala Glu Glu Arg Ile Val Gln Ser Val Val Glu Thr
    930                 935                 940

Ile Ala Arg Ser Ile Gly Lys Phe Phe Ala Ser Asp Thr Leu Cys Asn
945                 950                 955                 960

Pro Pro Asn Lys Val Lys Ile Pro Glu Thr His Gly Ile Arg Ala Arg
                965                 970                 975

Lys Gln Cys Lys Gly Pro Val Trp Thr Cys Ala Thr Ser Asp Asp Ala
            980                 985                 990

Arg Lys Trp Asn Gln Gly His Phe Val Thr Lys Phe Ala Leu Met Leu
            995                 1000                1005

Cys Glu Phe Thr Ser Pro Lys Trp Trp Pro Leu Ile Ile Arg Gly
    1010                1015                1020

Cys Ser Met Phe Thr Arg Lys Arg Met Met Asn Leu Asn Tyr
    1025                1030                1035

Leu Lys Ile Leu Asp Gly His Arg Glu Leu Asp Ile Arg Asp Asp
    1040                1045                1050

Phe Val Met Asp Leu Phe Lys Ala Tyr His Gly Glu Ala Glu Val
    1055                1060                1065

Pro Trp Ala Phe Lys Gly Lys Thr Tyr Leu Glu Thr Thr Thr Gly
    1070                1075                1080

Met Met Gln Gly Ile Leu His Tyr Thr Ser Ser Leu Leu His Thr
    1085                1090                1095

Ile His Gln Glu Tyr Ile Arg Ser Leu Ser Phe Lys Ile Phe Asn
    1100                1105                1110

Leu Lys Val Ala Pro Glu Met Ser Lys Ser Leu Val Cys Asp Met
    1115                1120                1125

Met Gln Gly Ser Asp Asp Ser Ser Met Leu Ile Ser Phe Pro Ala
    1130                1135                1140

Asp Asp Glu Lys Val Leu Thr Arg Cys Lys Val Ala Ala Ala Ile
    1145                1150                1155

Cys Phe Arg Met Lys Lys Glu Leu Gly Val Tyr Leu Ala Ile Tyr
    1160                1165                1170

Pro Ser Glu Lys Ser Thr Ala Asn Thr Asp Phe Val Met Glu Tyr
    1175                1180                1185

Asn Ser Glu Phe Tyr Phe His Thr Gln His Val Arg Pro Thr Ile
    1190                1195                1200

Arg Trp Ile Ala Ala Cys Cys Ser Leu Pro Glu Val Glu Thr Leu
    1205                1210                1215

Val Ala Arg Gln Glu Glu Ala Ser Asn Leu Met Thr Ser Val Thr
    1220                1225                1230

Glu Gly Gly Gly Ser Phe Ser Leu Ala Ala Met Ile Gln Gln Ala
    1235                1240                1245

Gln Cys Thr Leu His Tyr Met Leu Met Gly Met Gly Val Ser Glu
```

-continued

```
    1250              1255              1260

Leu Phe  Leu Glu Tyr Lys Lys  Ala Val Leu Lys  Trp  Asn Asp Pro
    1265              1270              1275

Gly Leu  Gly Phe Phe Leu Leu  Asp Asn Pro Tyr  Ala  Cys Gly Leu
    1280              1285              1290

Gly Gly  Phe Arg Phe Asn Leu  Phe Lys Ala Ile  Thr  Arg Thr Asp
    1295              1300              1305

Leu Gln  Lys Leu Tyr Ala Phe  Phe Met Lys Lys  Val  Lys Gly Ser
    1310              1315              1320

Ala Ala  Arg Asp Trp Ala Asp  Glu Asp Val Thr  Ile  Pro Glu Thr
    1325              1330              1335

Cys Ser  Val Ser Pro Gly Gly  Ala Leu Ile Leu  Ser  Ser Ser Leu
    1340              1345              1350

Lys Trp  Gly Ser Arg Lys Lys  Phe Gln Lys Leu  Arg  Asp Arg Leu
    1355              1360              1365

Asn Ile  Pro Glu Asn Trp Ile  Glu Leu Ile Asn  Glu  Asn Pro Glu
    1370              1375              1380

Val Leu  Tyr Arg Ala Pro Arg  Thr Gly Pro Glu  Ile  Leu Leu Arg
    1385              1390              1395

Ile Ala  Glu Lys Val His Ser  Pro Gly Val Val  Ser  Ser Leu Ser
    1400              1405              1410

Ser Gly  Asn Ala Val Cys Lys  Val Met Ala Ser  Ala  Val Tyr Phe
    1415              1420              1425

Leu Ser  Ala Thr Ile Phe Glu  Asp Thr Gly Arg  Pro  Glu Phe Asn
    1430              1435              1440

Phe Leu  Glu Asp Ser Lys Tyr  Ser Leu Leu Gln  Lys  Met Ala Ala
    1445              1450              1455

Tyr Ser  Gly Phe His Gly Phe  Asn Asp Met Glu  Pro  Glu Asp Ile
    1460              1465              1470

Leu Phe  Leu Phe Pro Asn Ile  Glu Glu Leu Glu  Ser  Leu Asp Ser
    1475              1480              1485

Ile Val  Tyr Asn Lys Gly Glu  Ile Asp Ile Ile  Pro  Arg Val Asn
    1490              1495              1500

Ile Arg  Asp Ala Thr Gln Thr  Arg Val Thr Ile  Phe  Asn Glu Gln
    1505              1510              1515

Lys Thr  Leu Arg Thr Ser Pro  Glu Lys Leu Val  Ser  Asp Lys Trp
    1520              1525              1530

Phe Gly  Thr Gln Lys Ser Arg  Ile Gly Lys Thr  Thr  Phe Leu Ala
    1535              1540              1545

Glu Trp  Glu Lys Leu Lys Lys  Ile Val Lys Trp  Leu  Glu Asp Thr
    1550              1555              1560

Pro Glu  Ala Thr Leu Ala His  Thr Pro Leu Asn  Asn  His Ile Gln
    1565              1570              1575

Val Arg  Asn Phe Phe Ala Arg  Met Glu Ser Lys  Pro  Arg Thr Val
    1580              1585              1590

Arg Ile  Thr Gly Ala Pro Val  Lys Lys Arg Ser  Gly  Val Ser Lys
    1595              1600              1605

Ile Ala  Met Val Ile Arg Asp  Asn Phe Ser Arg  Met  Gly His Leu
    1610              1615              1620

Arg Gly  Val Glu Asp Leu Ala  Gly Phe Thr Arg  Ser  Val Ser Ala
    1625              1630              1635

Glu Ile  Leu Lys His Phe Leu  Phe Cys Ile Leu  Gln  Gly Pro Tyr
    1640              1645              1650
```

```
Ser Glu  Ser Tyr Lys Leu Gln  Leu Ile Tyr Arg Val  Leu Ser Ser
    1655             1660             1665

Val Ser  Asn Val Glu Ile Lys  Glu Ser Asp Gly Lys  Thr Lys Thr
    1670             1675             1680

Asn Leu  Ile Gly Ile Leu Gln  Arg Phe Leu Asp Gly  Asp His Val
    1685             1690             1695

Val Pro  Ile Ile Glu Glu Met  Gly Ala Gly Thr Val  Gly Gly Phe
    1700             1705             1710

Ile Lys  Arg Gln Gln Ser Lys  Val Val Gln Asn Lys  Val Val Tyr
    1715             1720             1725

Tyr Gly  Val Gly Ile Trp Arg  Gly Phe Met Asp Gly  Tyr Gln Val
    1730             1735             1740

His Leu  Glu Ile Glu Asn Asp  Ile Gly Gln Pro Pro  Arg Leu Arg
    1745             1750             1755

Asn Val  Thr Thr Asn Cys Gln  Ser Ser Pro Trp Asp  Leu Ser Val
    1760             1765             1770

Pro Ile  Arg Gln Trp Ala Glu  Asp Met Gly Val Thr  Asn Asn Gln
    1775             1780             1785

Asp Tyr  Ser Ser Lys Ser Ser  Arg Gly Ala Arg Tyr  Trp Met His
    1790             1795             1800

Ser Phe  Arg Met Gln Gly Pro  Ser Lys Pro Phe Gly  Cys Pro Val
    1805             1810             1815

Tyr Ile  Ile Lys Gly Asp Met  Ser Asp Val Ile Arg  Leu Arg Lys
    1820             1825             1830

Glu Glu  Val Glu Met Lys Val  Arg Gly Ser Thr Leu  Asn Leu Tyr
    1835             1840             1845

Thr Lys  His His Ser His Gln  Asp Leu His Ile Leu  Ser Tyr Thr
    1850             1855             1860

Ala Ser  Asp Asn Asp Leu Ser  Pro Gly Ile Phe Lys  Ser Ile Ser
    1865             1870             1875

Asp Glu  Gly Val Ala Gln Ala  Leu Gln Leu Phe Glu  Arg Glu Pro
    1880             1885             1890

Ser Asn  Cys Trp Val Arg Cys  Glu Ser Val Ala Pro  Lys Phe Ile
    1895             1900             1905

Ser Ala  Ile Leu Glu Ile Cys  Glu Gly Lys Arg Gln  Ile Lys Gly
    1910             1915             1920

Ile Asn  Arg Thr Arg Leu Ser  Glu Ile Val Arg Ile  Cys Ser Glu
    1925             1930             1935

Ser Ser  Leu Arg Ser Lys Val  Gly Ser Met Phe Ser  Phe Val Ala
    1940             1945             1950

Asn Val  Glu Glu Ala His Asp  Val Asp Tyr Asp Ala  Leu Met Asp
    1955             1960             1965

Leu Met  Ile Glu Asp Ala Lys  Asn Asn Ala Phe Ser  His Val Val
    1970             1975             1980

Asp Cys  Ile Glu Leu Asp Val  Asn Gly Pro Tyr Glu  Met Glu Ser
    1985             1990             1995

Phe Asp  Thr Ser Asp Val Asn  Leu Phe Gly Pro Ala  His Tyr Lys
    2000             2005             2010

Asp Ile  Ser Ser Leu Ser Met  Ile Ala His Pro Leu  Met Asp Lys
    2015             2020             2025

Phe Val  Asp Tyr Ala Ile Ser  Lys Met Gly Arg Ala  Ser Val Arg
    2030             2035             2040
```

```
Lys Val  Leu Glu Thr Gly Arg  Cys Ser Ser Lys Asp  Tyr Asp Leu
    2045               2050              2055

Ser Lys  Val Leu Phe Arg Thr  Leu Gln Arg Pro Glu  Glu Ser Ile
    2060               2065              2070

Arg Ile  Asp Asp Leu Glu Leu  Tyr Glu Glu Thr Asp  Val Ala Asp
    2075               2080              2085

Asp Met  Leu Gly
    2090

<210> SEQ ID NO 48
<211> LENGTH: 1197
<212> TYPE: PRT
<213> ORGANISM: Artificial Sequence
<220> FEATURE:
<223> OTHER INFORMATION: RVFV 56/74 M poly(protein)

<400> SEQUENCE: 48

Met Tyr Val Leu Leu Thr Ile Leu Ile Thr Val Leu Val Cys Glu Ala
1               5                   10                  15

Val Ile Arg Val Ser Leu Ser Ser Thr Arg Glu Glu Thr Cys Phe Gly
                20                  25                  30

Asp Ser Thr Asn Pro Glu Met Ile Glu Gly Ala Trp Asp Ser Leu Arg
            35                  40                  45

Glu Glu Glu Met Pro Glu Glu Leu Ser Cys Ser Ile Ser Gly Ile Arg
        50                  55                  60

Glu Val Lys Thr Ser Ser Gln Glu Leu Tyr Arg Ala Leu Lys Ala Ile
65                  70                  75                  80

Ile Ala Ala Asp Gly Leu Asn Asn Ile Thr Cys His Gly Lys Asp Pro
                85                  90                  95

Glu Asp Lys Ile Ser Leu Ile Lys Gly Pro Pro His Lys Lys Arg Val
            100                 105                 110

Gly Ile Val Arg Cys Glu Arg Arg Asp Ala Lys Gln Ile Gly Arg
            115                 120                 125

Glu Thr Met Ala Gly Ile Ala Met Thr Val Leu Pro Ala Leu Ala Val
        130                 135                 140

Phe Ala Leu Ala Pro Val Val Phe Ala Glu Asp Pro His Leu Arg Asn
145                 150                 155                 160

Arg Pro Gly Lys Gly His Asn Tyr Ile Asp Gly Met Thr Gln Glu Asp
                165                 170                 175

Ala Thr Cys Lys Pro Val Thr Tyr Ala Gly Ala Cys Ser Ser Phe Asp
                180                 185                 190

Val Leu Leu Glu Lys Gly Lys Phe Pro Leu Phe Gln Ser Tyr Ala His
            195                 200                 205

His Arg Thr Leu Leu Glu Ala Val His Asp Thr Ile Ile Ala Lys Ala
        210                 215                 220

Asp Pro Pro Ser Cys Asp Leu Gln Ser Ala His Gly Asn Pro Cys Met
225                 230                 235                 240

Lys Glu Lys Leu Val Met Lys Thr His Cys Pro Asn Asp Tyr Gln Ser
                245                 250                 255

Ala His Tyr Leu Asn Asn Asp Gly Lys Val Ala Ser Val Lys Cys Pro
            260                 265                 270

Pro Lys Tyr Glu Leu Thr Glu Asp Cys Asn Phe Cys Arg Gln Met Thr
        275                 280                 285

Gly Ala Ser Leu Lys Lys Gly Ser Tyr Pro Leu Gln Asp Leu Phe Cys
    290                 295                 300
```

-continued

```
Gln Ser Ser Glu Asp Asp Gly Ser Lys Leu Lys Thr Lys Met Lys Gly
305             310             315             320

Val Cys Glu Val Gly Val Gln Ala Leu Lys Lys Cys Asp Gly Gln Leu
            325             330             335

Ser Thr Ala His Glu Val Val Pro Phe Ala Val Phe Lys Asn Ser Lys
            340             345             350

Lys Val Tyr Leu Asp Lys Leu Asp Leu Lys Thr Glu Glu Asn Leu Leu
            355             360             365

Pro Asp Ser Phe Val Cys Phe Glu His Lys Gly Gln Tyr Lys Gly Thr
370             375             380

Met Asp Ser Gly Gln Thr Lys Arg Glu Leu Lys Ser Ser Asp Ile Ser
385             390             395             400

Gln Cys Pro Lys Ile Gly Gly His Gly Ser Lys Lys Cys Thr Gly Asp
            405             410             415

Ala Ala Phe Cys Ser Ala Tyr Glu Cys Thr Ala Gln Tyr Ala Asn Ala
            420             425             430

Tyr Cys Ser His Ala Asn Gly Ser Gly Ile Val Gln Ile Gln Val Ser
            435             440             445

Gly Val Trp Lys Lys Pro Leu Cys Val Gly Tyr Glu Arg Val Val Val
    450             455             460

Lys Arg Glu Leu Ser Ala Lys Pro Ile Gln Arg Val Glu Pro Cys Thr
465             470             475             480

Thr Cys Ile Thr Lys Cys Glu Pro His Gly Leu Val Val Arg Ser Thr
            485             490             495

Gly Phe Lys Ile Ser Ser Ala Val Ala Cys Ala Ser Gly Val Cys Val
            500             505             510

Thr Gly Ser Gln Ser Pro Ser Thr Glu Ile Thr Leu Lys Tyr Pro Gly
            515             520             525

Ile Ser Gln Ser Ser Gly Gly Asp Ile Gly Val His Met Ala His Asp
    530             535             540

Asp Gln Ser Val Ser Ser Lys Ile Val Ala His Cys Pro Pro Gln Asp
545             550             555             560

Pro Cys Leu Val His Gly Cys Ile Val Cys Ala His Gly Leu Ile Asn
            565             570             575

Tyr Gln Cys His Thr Ala Leu Ser Ala Phe Val Val Val Phe Val Phe
            580             585             590

Ser Ser Ile Ala Ile Thr Cys Leu Ala Ile Leu Tyr Arg Val Leu Lys
    595             600             605

Cys Leu Lys Ile Ala Pro Arg Lys Val Leu Asn Pro Leu Met Trp Ile
    610             615             620

Thr Ala Phe Ile Arg Trp Val Tyr Lys Lys Met Val Ala Arg Val Ala
625             630             635             640

Asp Asn Ile Asn Gln Val Asn Arg Glu Ile Gly Trp Met Glu Gly Gly
            645             650             655

Gln Leu Val Leu Gly Asn Pro Ala Pro Ile Pro Arg His Ala Pro Ile
            660             665             670

Pro Arg Tyr Ser Thr Tyr Leu Met Leu Leu Leu Ile Val Ser Tyr Ala
            675             680             685

Ser Ala Cys Ser Glu Leu Ile Gln Ala Ser Ser Arg Ile Thr Thr Cys
    690             695             700

Ser Thr Glu Gly Val Asn Thr Lys Cys Arg Leu Ser Gly Thr Ala Leu
705             710             715             720

Ile Arg Ala Gly Ser Val Gly Ala Glu Ala Cys Leu Met Leu Lys Gly
```

-continued

```
                725             730             735

Val Lys Glu Asp Gln Thr Lys Phe Leu Lys Ile Lys Thr Val Ser Ser
        740             745             750

Glu Leu Ser Cys Arg Glu Gly Gln Ser Tyr Trp Thr Gly Ser Phe Ser
        755             760             765

Pro Lys Cys Leu Ser Ser Arg Arg Cys His Leu Val Gly Glu Cys His
    770             775             780

Val Asn Arg Cys Leu Ser Trp Arg Asp Asn Glu Thr Ser Ala Glu Phe
785             790             795             800

Ser Phe Val Gly Glu Ser Thr Thr Met Arg Glu Asn Lys Cys Phe Glu
            805             810             815

Gln Cys Gly Gly Trp Gly Cys Gly Cys Phe Asn Val Asn Pro Ser Cys
            820             825             830

Leu Phe Val His Thr Tyr Leu Gln Ser Val Arg Lys Glu Ala Leu Arg
            835             840             845

Val Phe Asn Cys Ile Asp Trp Val His Lys Leu Ser Leu Glu Ile Thr
    850             855             860

Asp Phe Asp Gly Ser Val Ser Thr Ile Asp Leu Gly Ala Ser Ser Ser
865             870             875             880

Arg Phe Thr Asn Trp Gly Ser Val Ser Leu Ser Leu Asp Ala Glu Gly
            885             890             895

Ile Ser Gly Ser Asn Ser Phe Ser Phe Ile Glu Ser Pro Gly Lys Gly
            900             905             910

Tyr Ala Ile Val Asp Glu Pro Phe Ser Glu Ile Pro Arg Gln Gly Phe
            915             920             925

Leu Gly Glu Ile Arg Cys Asn Ser Glu Ser Ser Val Leu Ser Ala His
        930             935             940

Glu Ser Cys Leu Arg Ala Pro Asn Leu Ile Ser Tyr Lys Pro Met Ile
945             950             955             960

Asp Gln Leu Glu Cys Thr Thr Asn Leu Ile Asp Pro Phe Val Val Phe
            965             970             975

Glu Arg Gly Ser Leu Pro Gln Thr Arg Asn Glu Lys Thr Phe Ala Ala
            980             985             990

Ser Lys Gly Asn Arg Gly Val Gln  Ala Phe Ser Lys Gly  Ser Val Gln
        995             1000             1005

Ala Asp Leu Thr Leu Met Phe  Asp Asn Phe Glu Val  Asp Phe Val
    1010             1015             1020

Gly Ala Ala Val Ser Cys Asp  Ala Ala Phe Leu Asn  Leu Thr Gly
    1025             1030             1035

Cys Tyr Ser Cys Asn Ala Gly  Ala Arg Val Cys Leu  Ser Ile Thr
    1040             1045             1050

Ser Thr Gly Thr Gly Thr Leu  Ser Ala His Asn Lys  Asp Gly Ser
    1055             1060             1065

Leu His Ile Val Leu Pro Ser  Glu Asn Gly Thr Lys  Asp Gln Cys
    1070             1075             1080

Gln Ile Leu His Phe Thr Val  Pro Glu Val Glu Glu  Glu Phe Met
    1085             1090             1095

Tyr Ser Cys Asp Gly Asp Glu  Arg Pro Leu Leu Val  Lys Gly Thr
    1100             1105             1110

Leu Ile Ala Ile Asp Pro Phe  Asp Asp Arg Arg Glu  Ala Gly Gly
    1115             1120             1125

Glu Ser Thr Val Val Asn Pro  Lys Ser Gly Ser Trp  Asn Phe Phe
    1130             1135             1140
```

-continued

```
Asp Trp  Phe Ser Gly Leu Met  Ser Trp Phe Gly Gly  Pro Leu Lys
    1145             1150              1155

Thr Ile  Leu Leu Ile Cys Leu  Tyr Val Ala Leu Ser  Ile Gly Leu
    1160             1165              1170

Phe Phe  Leu Leu Ile Tyr Leu  Gly Arg Thr Gly Leu  Ser Lys Met
    1175             1180              1185

Trp Leu  Ala Ala Thr Lys Lys  Ala Ser
    1190             1195

<210> SEQ ID NO 49
<211> LENGTH: 265
<212> TYPE: PRT
<213> ORGANISM: Artificial Sequence
<220> FEATURE:
<223> OTHER INFORMATION: RVFV 56/74 NSs protein

<400> SEQUENCE: 49

Met Asp Tyr Phe Pro Val Ile Ser Val Asp Leu Gln Ser Gly Arg Arg
1               5                   10                  15

Val Val Ser Val Glu Tyr Ile Arg Gly Asp Gly Pro Pro Arg Ile Pro
            20                  25                  30

Tyr Ser Met Val Gly Pro Cys Cys Val Phe Leu Met His His Arg Pro
        35                  40                  45

Ser His Glu Val Arg Leu Arg Phe Ser Asp Phe Tyr Asn Val Gly Glu
    50                  55                  60

Phe Pro Tyr Arg Val Gly Leu Gly Asp Phe Val Ser Asn Val Ala Pro
65                  70                  75                  80

Pro Pro Ala Lys Pro Phe Gln Arg Leu Ile Asp Leu Ile Gly His Met
                85                  90                  95

Thr Leu Ser Asp Phe Thr Arg Phe Pro Asn Leu Lys Glu Ala Ile Ser
            100                 105                 110

Trp Pro Leu Gly Glu Pro Ser Leu Ala Phe Phe Asp Leu Ser Ser Thr
        115                 120                 125

Arg Val His Arg Ser Asp Asp Ile Arg Arg Asp Gln Ile Ala Thr Leu
    130                 135                 140

Ala Met Arg Ser Cys Lys Ile Thr Asn Asp Leu Glu Asp Ser Phe Val
145                 150                 155                 160

Gly Leu His Arg Met Ile Val Thr Glu Ala Ile Leu Arg Gly Ile Asp
                165                 170                 175

Leu Cys Leu Leu Pro Gly Phe Asp Leu Met Tyr Glu Val Ala His Val
            180                 185                 190

Gln Cys Val Arg Leu Leu Gln Ala Ala Arg Glu Asp Ile Ser Asn Ala
        195                 200                 205

Val Val Pro Asn Ser Ala Leu Ile Ala Leu Met Glu Glu Ser Leu Met
    210                 215                 220

Leu Arg Ser Ser Leu Pro Ser Met Met Gly Arg Asn Asn Trp Val Pro
225                 230                 235                 240

Val Val Pro Pro Ile Pro Asp Val Glu Ile Glu Ser Glu Glu Glu Ser
                245                 250                 255

Asp Asp Asp Gly Phe Val Glu Val Asp
            260                 265

<210> SEQ ID NO 50
<211> LENGTH: 245
<212> TYPE: PRT
<213> ORGANISM: Artificial Sequence
```

-continued

```
<220> FEATURE:
<223> OTHER INFORMATION: RVFV 56/74 N protein

<400> SEQUENCE: 50

Met Asp Asn Tyr Gln Glu Leu Ala Ile Gln Phe Ala Ala Gln Ala Val
1               5                   10                  15

Asp Arg Asn Glu Ile Glu Gln Trp Val Arg Glu Phe Ala Tyr Gln Gly
            20                  25                  30

Phe Asp Ala Arg Arg Val Ile Glu Leu Leu Lys Gln Tyr Gly Gly Ala
        35                  40                  45

Gly Trp Glu Lys Asp Ala Lys Lys Met Ile Val Leu Ala Leu Thr Arg
    50                  55                  60

Gly Asn Lys Pro Arg Arg Met Met Met Lys Met Ser Lys Glu Gly Lys
65                  70                  75                  80

Ala Thr Val Glu Ala Leu Ile Asn Lys Tyr Lys Leu Lys Glu Gly Asn
                85                  90                  95

Pro Ser Arg Asp Glu Leu Thr Leu Ser Arg Val Ala Ala Ala Leu Ala
            100                 105                 110

Gly Trp Thr Cys Gln Ala Leu Val Val Leu Ser Glu Trp Leu Pro Val
        115                 120                 125

Thr Gly Thr Thr Met Asp Gly Leu Ser Pro Ala Tyr Pro Arg His Met
    130                 135                 140

Met His Pro Ser Phe Ala Gly Met Val Asp Pro Ser Leu Pro Glu Asp
145                 150                 155                 160

Tyr Leu Arg Ala Ile Leu Asp Ala His Ser Leu Tyr Leu Leu Gln Phe
                165                 170                 175

Ser Arg Val Ile Asn Pro Asn Leu Arg Gly Arg Thr Lys Glu Glu Val
            180                 185                 190

Ala Ala Thr Phe Thr Gln Pro Met Asn Ala Ala Val Asn Ser Asn Phe
        195                 200                 205

Ile Ser His Glu Lys Arg Arg Glu Phe Leu Lys Ala Phe Gly Leu Val
    210                 215                 220

Asp Ser Asn Gly Lys Pro Ser Ala Ala Val Met Ala Ala Ala Gln Ala
225                 230                 235                 240

Tyr Lys Thr Ala Ala
                245

<210> SEQ ID NO 51
<211> LENGTH: 6404
<212> TYPE: DNA
<213> ORGANISM: Artificial Sequence
<220> FEATURE:
<223> OTHER INFORMATION: ZH548 RVF virus L segment
<220> FEATURE:
<221> NAME/KEY: gene
<222> LOCATION: (19)..(6297)
<223> OTHER INFORMATION: ZH548 RVF virus L-segment open reading frame

<400> SEQUENCE: 51
acacaaaggc gcccaatcat ggattctata ttatcaaaac agctggttga caagactggt        60
tttgttagag tgccaatcaa gcattttgac tgtacaatgc taactctggc acttccaaca       120
tttgatgttt ccaagatggt agatagaatt accatagact tcaatctgga tgatatacaa       180
ggagcatctg aaataggctc aactttgcta ccctccatgt cgatagatgt ggaagatatg       240
gccaattttg ttcacgattt caccttttggc cacttagctg acaagactga cagactgtta       300
atgcgtgagt ttcccatgat gaatgacggg tttgatcatt tgagccctga catgatcatt       360
```

-continued

```
aaaactacat ctggcatgta caacatcgtt gagttcacca cctttagggg agatgaaaga    420
ggtgcattcc aggctgccat gactaaactc gctaagtatg aggttccttg tgagaacaga    480
tctcagggca ggactgttgt tctttatgtt gttagtgctt atcggcatgg tgtatggtct    540
aatctggagc tagaggactc tgaagcagag gagatggttt ataggtacag acttgctctt    600
agtgtgatgg atgagctaag gaccttgttc ccagaactgt catccacaga tgaggaacta    660
gggaagactg agagagagtt gctagccatg gtctcctcca tccaaataaa ttggtcagtc    720
acagaatctg tgtttccacc cttcagcaga gaaatgtttg acaggtttag atcctcccct    780
cccgattcag agtatatcac gaggatagtg agcagatgcc taataaattc tcaagagaaa    840
ctcatcaata gttccttctt tgctgaaggg aatgataagg ctctgagatt ttcaaaaaac    900
gctgaagagt gttccttggc agtagagaga gccttaaatc agtatagagc agaagacaac    960
cttagggacc tcaatgacca caagtcaact attcagctgc ctccctggct gtcctatcat   1020
gatgtcgatg gcaaagatct gtgccctctt cagggactag atgtgagagg ggaccatccc   1080
atgtgcaact tgtggaggga agtggtcacc tctgcaaacc tagaggagat tgagaggatg   1140
cacgatgatg cagcagcaga acttgagttt gcccttctcg gagtaaagga caggccagat   1200
gagagaaaca gataccatag agtccaccta aatatgggct cagatgatag tgtctacata   1260
gctgctttag gagttaatgg aaagaagcat aaagcagaca ctttagtgca acaaatgaga   1320
gacaggagta aacagccttt ctccccagac cacgatgtgg atcacatatc tgaatttctc   1380
tctgcatgct ctagtgactt gtgggcaaca gatgaggacc tgtacagccc tctctcttgt   1440
gataaagagc ttagattggc agcccagagg attcatcagc catccttgtc agaaaggggt   1500
ttcaatgaga tcataacaga gcactacaaa ttcatgggaa gtaggatagg ttcatggtgc   1560
caaatggtca gcttgatagg agctgagcta tcagcttctg ttaaacaaca tgtcaagcct   1620
aactactttg tgattaaacg actactaggt tctgggattt tcttgctaat caagcccact   1680
tccagcaaaa gccatatatt tgtgtctttt gcaattaagc gctcttgctg ggcctttgat   1740
ctctccactt ccagggtttt caagccctac atagatgctg gggatctgtt agttactgac   1800
tttgtttctt ataagctaag caagcttacc aacctctgca agtgcgtttc attaatggag   1860
tcctccttct cattctgggc agaagcattt ggaattccaa gctggaactt tgttggtgac   1920
ttgttcaggt cttcagactc tgcagcaatg gatgcctcat acatgggcaa actttcttta   1980
ttaacccttt tggaagacaa agcagcaact gaagagttac agactattgc aagatatata   2040
atcatggagg gctttgtctc gcccccagaa atcccaaaac ctcacaagat gacctctaag   2100
tttcctaagg ttctcaggtc agagctgcag gtttacttat taaactgctt atgcagaact   2160
atccagagaa tagcaggtga gcccttcatt cttaagaaga aggatgggtc tatatcctgg   2220
ggtggcatgt tcaatccttt ttcagggcgt ccactgcttg atatgcaacc actcatcagc   2280
tgttgttaca atggttactt taaaaataaa gaagaagaga ctgagccttc gtccctttct   2340
gggatgtata agaaaatcat agaacttgag caccttagac cacagtcaga tgccttcttg   2400
ggttacaaag atccagaact tcccagaatg catgagttca gtgtttccta cttgaaggag   2460
gcttgcaatc atgctaagct agtcttgagg agcctctatg acagaatttt catggagcag   2520
atagacaacc agattattcg agagctcagt gggttgactc tagaaaggtt ggccacactt   2580
aaggccacaa gcaactttaa tgagaattgg tatgtctata aggatgtagc agacaaaaac   2640
tacacaaggg ataaattatt agtgaagatg tcaaatatg cctctgaggg aaagagccta   2700
gctatccaga agtttgagga ttgtatgagg cagatagagt cacaaggatg catgcatatt   2760
```

-continued

```
tgtttgttta agaaacaaca gcatggaggt ctgagagaga tctatgtgat gggtgcagag    2820
gaaagaattg ttcaatcggt ggtggagaca atagccaggt ccatagggaa gttctttgct    2880
tctgataccc tctgtaaccc ccccaataaa gtgaaaattc ctgagacaca tggcatcagg    2940
gccgggaagc aatgtaaggg gcctgtgtgg acttgtgcaa catcagatga tgcaaggaag    3000
tggaaccaag gccattttgt tacaaagttt gccctcatgc tgtgtgagtt cacctctcct    3060
aaatggtggc cgctgatcat tagggatgc tcaatgttta ccaggaaaag gatgatgatg     3120
aatttgaatt atcttaagat cctggatggt catcgggagc ttgatattag agatgacttt    3180
gtgatggatc tcttcaaagc ttatcatggc gaggcagaag ttccatgggc ctttaaaggc    3240
aaaacatatt tggaaccac aacagggatg atgcaggaa tactgcatta tacttcctca      3300
ctattacaca ccattcacca agaatacatc cggtccttgt cctttaagat attcaacctg    3360
aaggttgctc ctgagatgag caagagcctg gtttgtgaca tgatgcaagg atcagatgat    3420
agtagtatgc taatcagctt cccagctgat gatgagaagg ttcttaccag atgcaaagtg    3480
gccgcagcta tatgcttccg catgaagaag gagctgggag tgtaccttgc catttacccc    3540
tcagagaagt ccacagcaaa cacagatttt gtgatggagt acaattctga attttatttc    3600
cacacccagc atgttagacc aacgatcagg tggattgcag cttgttgcag cctgccagaa    3660
gtggaaacac tagtagcccg ccaggaagag gcctctaacc taatgacttc agttactgag    3720
ggaggtgggt cattctcctt agctgcaatg attcagcaag ctcagtgtac tctccattac    3780
atgctgatgg gcatgggagt gtctgagcta ttcttagagt ataagaaggc agtgctgaag    3840
tggaatgacc ctggcctggg tttcttcctg cttgacaatc cttatgcgtg cggattggga    3900
ggtttcagat ttaatctctt caaagctatc accagaactg atttgcagaa gctatatgct    3960
ttcttcatga agaaggtcaa gggctcagct gctagggact gggcagatga agatgtcacc    4020
atcccagaaa cgtgtagcgt gagcccaggt ggcgctctaa ttcttagctc ctctctaaag    4080
tggggatcta ggaagaagtt tcagaaattg agagaccgtt tgaacatacc agagaactgg    4140
attgaactaa taaatgagaa tccagaggtg ctctatcggg ctcccagaac aggcccagaa    4200
atattgttgc gcattgcaga gaaagtccat agcccaggtg ttgtgtcatc attgtcttct    4260
ggcaatgcag tttgtaaagt catggcctca gctgtatact tcttatcagc aacaattttt    4320
gaggacactg gacgtcctga gttcaacttc ttggaggatt ctaagtacag cttgctacaa    4380
aagatggctg catattctgg ctttcatggt ttcaatgata tggagccaga agatatatta    4440
ttcttattcc cgaatattga ggaattagaa tcactggatt ctatagttta caacaaggga    4500
gaaatagaca tcatcccaag agtcaacatc agggatgcaa cccaaaccag ggtcactatc    4560
tttaatgagc agaagaccct ccggacatct ccagagaagt tggtgtcaga caagtggttt    4620
gggactcaga gagtaggat aggcaaaaca accttcctgg ctgaatggga aaagctaaag    4680
aaaattgtaa agtggttgga agacactcca gaagcaactc tagctcacac cccactgaat    4740
aaccatattc aagttaggaa tttctttgct agaatggaaa gcaagcctag aacagtcaga    4800
ataacaggag ctccagtaaa gaagaggtca ggggttagta agatagctat ggttatccgt    4860
gacaatttct cccggatggg ccatcttcga ggtgtagaag accttgctgg cttcactcgt    4920
agtgtgtcag ctgaaattct caagcacttt ctattctgta tactacaagg tccatacagt    4980
gagagctata agctacagct aatctacaga gtcctaagct cagtgtcaaa cgttgagata    5040
aaggaatcag atggtaagac aaaaaccaac ttgattggaa tccttcagag atttctagat    5100
```

-continued

```
ggtgatcacg ttgtccccat aattgaagag atgggagccg aacagtggg tggattcatc    5160 aagagacaac aatctaaagt tgtgcagaac aaagtggtct attatggagt tgggatttgg    5220
agaggcttca tggatggata tcaggtccat ctagagatag aaaatgacat aggacagccc    5280
ccaaggctta ggaatgtcac aactaactgt cagagcagcc catgggacct gagtattcca    5340
ataaggcaat gggcagaaga catgggggtc acaaacaacc aggattattc ctctaaatct    5400
agcagggggg ccagatattg gatgcattca ttcaggatgc aaggacctag caagccattt    5460
ggatgcccag tttatattat taagggtgat atgtcagatg tcatcagact gagaaaggag    5520
gaggtggaga tgaaagtacg gggctctact ctcaacttgt acaccaagca ccattctcat    5580
caggacctac acattctatc ttacactgca tcagacaatg atctcagtcc aggcattttc    5640
aagtcaatat cagatgaggg ggtggctcaa gccctgcaat tatttgagag ggagccaagc    5700
aactgctggg tgagatgtga gtctgtagcc ccaaaattta tatcagccat ccttgagata    5760
tgtgagggga agacagat aaagggaatt aacagaacca gactctcaga gattgtgaga    5820
atttgttctg aatcttccct aagatcaaaa gtcggatcta tgttctcatt tgtcgccaat    5880
gtcgaggagg cccatgatgt tgattatgat gcgttaatgg atctaatgat agaggatgcc    5940
aagaacaatg cattcagtca tgttgttgac tgcatagagt tggatgttag tggcccttac    6000
gagatggagt cttttgatac atctgatgtc aatctctttg gccagcccca ttacaaggac    6060
atcagttcat tatctatgat tgctcatccc ttaatggata agtttgttga ttatgctatt    6120
tctaagatgg ggagagcctc agttaggaaa gttctagaaa caggtcggtg ctccagcaaa    6180
gactatgatt tatcaaaggt tctcttcaga actctacaga gaccagaaga aagcattagg    6240
atagatgatc tggaattata tgaggagaca gatgtggcgg atgacatgct aggctaagac    6300
cagtaagcaa agtcaggctt agatttaggg atactatgct agtattggaa tccatgtggg    6360
ttctgatact agcatagtgc tacaatattg ggcggtcttt gtgt    6404
```

<210> SEQ ID NO 52
<211> LENGTH: 3885
<212> TYPE: DNA
<213> ORGANISM: Artificial Sequence
<220> FEATURE:
<223> OTHER INFORMATION: ZH548 RVF virus M segment
<220> FEATURE:
<221> NAME/KEY: gene
<222> LOCATION: (21)..(3614)
<223> OTHER INFORMATION: ZH548 RFV virus gene encoding M (poly)protein

<400> SEQUENCE: 52

```
acacaaagac ggtgcattaa atgtatgttt tattaacaat tctaatctcg gttctggtgt    60
gtgaagcggt tattagagtg tctctaagct ccacaagaga agagacctgc tttggtgact    120
ccactaaccc agagatgatt gaaggagctt gggattcact cagagaggag gagatgccgg    180
aggagctctc ctgttctata tcaggcataa gagaggttaa gacctcaagc caggagttat    240
acagggcatt aaaagccatc attgctgctg atggcttgaa caacatcacc tgccatggta    300
aggatcctga ggacaagatt tccctcataa agggtcctcc tcacaaaaag cgggtgggga    360
tagttcggtg tgagagacga agagatgcta agcaaatagg gagagaaacc atggcaggga    420
ttgcaatgac agtccttcca gccttagcag ttttttgcttt ggcacctgtt gtttttgctg    480
aagaccccca tctcagaaac agaccaggga aggggcacaa ctacattgac gggatgactc    540
aggaggatgc cacatgcaaa cctgtgacat atgctggggc atgtagcagt tttgatgtct    600
tgcttgaaaa gggaaaattt ccccttttcc agtcgtatgc tcatcataga actctactag    660
```

-continued

```
aggcagttca cgacaccatc attgcaaagg ctgatccacc tagctgtgac cttctgagtg       720
ctcatgggaa cccctgcatg aaagagaaac tcgtgatgaa gacacactgt ccaaatgact       780
accagtcagc tcattacctc aacaatgacg ggaaaatggc ttcagtcaag tgccctccta       840
agtatgagct cactgaggac tgcaactttt gtaggcagat gacaggtgct agcctgaaga       900
aggggtctta tcctctccaa gacttgtttt gtcagtcaag tgaggatgat ggatcaaaat       960
taaaaacaaa aatgaaaggg gtctgcgaag tggggggttca agcactcaaa aagtgtgatg      1020
gccaactcag cactgcacat gaggttgtgc cctttgcagt gtttaagaac tcaaagaagg      1080
tttatcttga taagcttgac cttaagactg aggagaatct gctaccagac tcatttgtct      1140
gtttcgagca taagggacag tacaaaggaa caatggactc tggtcagact aagagggagc      1200
tcaaaagctt tgatatctct cagtgcccca agattggagg acatggtagt aagaagtgca      1260
ctggggacgc agcattttgc tctgcttatg agtgcactgc tcagtacgcc aatgcctatt      1320
gttcacatgc taatgggtca gggattgtgc agatacaag atcaggggtc tggaagaagc      1380
ctttatgtgt agggtatgag agagtggttg tgaagagaga actctctgcc aagcccatcc      1440
agagagttga gccttgcaca acttgtataa ccaaatgtga gcctcatgga ttggttgtcc      1500
gatcaacagg gttcaagata tcatcagcag ttgcttgtgc tagcggagtt tgcgtcacag      1560
gatcgcagag tccttccacc gagattacac tcaagtatcc agggatatcc cagtcttctg      1620 gggggggacat aggggttcac atggcacacg atgatcagtc agttagctcc aaaatagtag      1680
ctcactgccc tccccaggac ccgtgcttag tgcatgactg catagtgtgt gctcatggcc      1740
tgataaatta ccagtgtcac actgctctca gtgcctttgt tgttgtgttt gtattcagtt      1800
ctattgcaat aatttgttta gctattcttt ataggggtgct taagtgcctg aagattgccc      1860
caaggaaagt tctgaatcca ctaatgtgga tcacagcctt catcagatgg atatataaga      1920
agatggttgc cagagtggca gacaacatta tcaagtgaa cagggaaata ggatggatgg      1980
aaggaggtca gttggttcta gggaaccctg cccctattcc tcgtcatgcc ccaatcccac      2040
gttatagcac atacctgatg ttattattga ttgtctcata tgcatcagca tgttcagaac      2100
tgattcaggc aagctccaga atcaccactt gctctacaga gggtgttaac accaagtgta      2160
gactgtctgg cacagcattg atcagagcag ggtcagttgg ggcagaggct tgtttgatgt      2220
tgaagggggt caaggaagat caaaccaagt tcttaaagat aaaaactgtc tcaagtgagc      2280
tatcatgcag ggagggccag agttattgga ctgggtcctt tagccctaaa tgtttgagct      2340
caaggagatg ccaccttgtc ggggaatgcc atgtgaatag gtgtctgtct tggagggaca      2400
atgaaacttc agcagagttt tcatttgttg gggaaagcac gaccatgcga gagaataagt      2460
gttttgagca atgtggagga tggggggtgtg ggtgtttcaa tgtgaaccca tcttgcttat      2520
ttgtgcacac gtatctgcag tcagttagaa aagaggccct tagagttttt aactgtatcg      2580
actgggtgca taaactcact ctagagatca cagactttga tggctctgtt tcaacaatag      2640
acttgggagc atcatctagc cgtttcacaa actggggttc agttagcctc tcactggacg      2700
cagagggcat ttcaggctca aatagctttt ctttcattga gagcccaggc aaagggtatg      2760
caattgttga tgagccattc tcagaaattc ctcggcaagg gttcttgggg gagatcaggt      2820
gcaattcaga gtcctcagtc ctgagtgctc atgaatcatg ccttagggca ccaaacctta      2880
tctcatacaa gcccatgata gatcaattgg agtgcacaac aaatctgatt gatccctttg      2940
ttgtctttga gaggggttct ctgccacaga caaggaatga caaaaccttt gcagcttcaa      3000
```

```
aaggaaatag aggtgttcaa gctttctcta agggctctgt acaagctgat ctaactctga   3060
tgtttgacaa ttttgaggtg gactttgtgg gagcagccgt atcttgtgat gccgccttct   3120
taaatttgac aggttgctat tcttgcaatg caggggccag ggtctgcctg tctatcacat   3180
ccacaggaac tggatctctc tctgcccaca ataaggatgg gtctctgcat atagtccttc   3240
catcagagaa tggaacaaaa gaccagtgtc agatactaca cttcactgtg cctgaagtag   3300
aggaggagtt tatgtactct tgtgatggag atgagcggcc tctgttggtg aaggggaccc   3360
tgatagccat tgatccattt gatgataggc gggaagcagg gggggaatca acagttgtga   3420
atccaaaatc tggatcttgg aatttctttg actggttttc tggactcatg agttggtttg   3480
gagggcctct taaaactata ctcctcattt gcctgtatgt tgcattatca attgggctct   3540
ttttcctcct tatatatctt ggaagaacag gcctctctaa aatgtggctt gctgccacta   3600
agaaggcctc atagatcagt acgtgtaaaa gcaatatgtt gaaataagta gacataagca   3660
aacctaatta tgtaagtatt gtacagatag gtcaaattat tggaatatcc aagcttagaa   3720
acttatgcaa taatacttta gatgtaagct tagttgtaat ttggggtggt ggggtgaggc   3780
agcagcagtc tcaagtgctt gtgaatattc tagttggcgt aatcgtcttt tgccagatta   3840
gctgggaatt aaactaactc tttgaagttg caccggtctt tgtgt   3885
```

```
<210> SEQ ID NO 53
<211> LENGTH: 1690
<212> TYPE: DNA
<213> ORGANISM: Artificial Sequence
<220> FEATURE:
<223> OTHER INFORMATION: ZH548 RVF virus S segment
<220> FEATURE:
<221> NAME/KEY: gene
<222> LOCATION: (35)..(832)
<223> OTHER INFORMATION: ZH548 RVF virus gene encoding NSs protein
<220> FEATURE:
<221> NAME/KEY: gene
<222> LOCATION: (915)..(1652)
<223> OTHER INFORMATION: ZH548 RVF virus gene encoding N protein

<400> SEQUENCE: 53
```

```
acacaaagac cccctagtgc ttatcaagta tatcatggat tactttcctg tgatatctgt    60
tgatttgcag agtggtcgtc gtgttgtgtc agtggagtac tttagaggag atggtcctcc   120
caggatacct tattctatgg ttgggccctg ttgtgtcttt ctcatgcacc atcgtcctag   180
tcacgaggtt cgcttgcgat tctctgattt ctacaatgtc ggagaattcc ataccgagt   240 cggacttgga gactttgcat caaacgttgc acctccacca gcgaagcctt ttcagagact   300
tattgatcta ataggccata tgactcttag tgatttcaca aggttcccca atctgaaaga   360
agccatatcc tggcctcttg agaaccctc actggctttc tttgacctaa gctctactag   420
agtgcatagg aatgatgaca ttagaaggga tcagattgcc actctagcaa tgaggagttg   480
caagatcacc aatgatctag aggactcctt tgttggctta cacaggatga tagcgactga   540
ggccatcctc agagggattg acctgtgcct gttgccaggc tttgatctca tgtatgaggt   600
tgctcacgta cagtgcgttc ggcttctgca agcagcaaaa gaggacattt ctaatgctgt   660
agttccaaac tcagccctca ttgttcttat ggaggagagc ctgatgctgc gctcatcact   720
tcccagcatg atggggagaa acaactggat tccagttatt cctccaatcc cagatgttga   780
gatggaatca gaggaggaga gtgatgatga tggatttgtt gaggttgatt agaggttaag   840
gctgccccac ccccaccccc caatcccga ccgtaacccc aactcccctt ccccccaacc   900
ccctgggcag ccacttaggc tgctgtcttg taagcctgag cggctgccat gacagcagct   960
```

```
gacggcttcc cattggaatc cacaagtcca aaggctttca agaattctct cctcttctca    1020
tggcttataa agttgctatt cactgctgca ttcattggct gcgtgaacgt tgcagcaacc    1080
tcctcttttg ttctacctcg gaggtttggg ttgatgaccc gggagaactg cagcagatac    1140
agagagtgag catctaatat tgcccttaga tagtctcctg gtagagaagg atccaccatg    1200
ccagcaaagc tggggtgcat catatgcctc gggtatgcag gggataggcc gtccatggta    1260
gtcccagtga caggaagcca ctcactcaag acgaccaaag cctggcatgt ccagccagcc    1320
aaggcggcag caactcgtga tagagtcaac tcatcccggg aaggattccc ttcctttagc    1380
ttatacttgt tgatgagagc ctccacagtt gctttgcctt ctttcgacat tttcatcatc    1440
atcctcctgg gcttgttgcc acgagttaga gccagaacaa tcattttctt ggcatccttc    1500
tcccagtcag ccccaccata ctgctttaag agttcgataa ctctacgggc atcaaaccct    1560
tgataagcaa actctcggac ccactgttca atctcattgc ggtccactgc ttgagcagca    1620
aactggatcg caagctcttg atagttgtcc attattgtaa tagtgtttgt atctctaggg    1680
agctttgtgt                                                         1690
```

```
<210> SEQ ID NO 54
<211> LENGTH: 2092
<212> TYPE: PRT
<213> ORGANISM: Artificial Sequence
<220> FEATURE:
<223> OTHER INFORMATION: ZH548 RVFV L protein

<400> SEQUENCE: 54

Met Asp Ser Ile Leu Ser Lys Gln Leu Val Asp Lys Thr Gly Phe Val
1               5                   10                  15

Arg Val Pro Ile Lys His Phe Asp Cys Thr Met Leu Thr Leu Ala Leu
            20                  25                  30

Pro Thr Phe Asp Val Ser Lys Met Val Asp Arg Ile Thr Ile Asp Phe
        35                  40                  45

Asn Leu Asp Asp Ile Gln Gly Ala Ser Glu Ile Gly Ser Thr Leu Leu
    50                  55                  60

Pro Ser Met Ser Ile Asp Val Glu Asp Met Ala Asn Phe Val His Asp
65                  70                  75                  80

Phe Thr Phe Gly His Leu Ala Asp Lys Thr Asp Arg Leu Leu Met Arg
                85                  90                  95

Glu Phe Pro Met Met Asn Asp Gly Phe Asp His Leu Ser Pro Asp Met
            100                 105                 110

Ile Ile Lys Thr Thr Ser Gly Met Tyr Asn Ile Val Glu Phe Thr Thr
        115                 120                 125

Phe Arg Gly Asp Glu Arg Gly Ala Phe Gln Ala Ala Met Thr Lys Leu
    130                 135                 140

Ala Lys Tyr Glu Val Pro Cys Glu Asn Arg Ser Gln Gly Arg Thr Val
145                 150                 155                 160

Val Leu Tyr Val Val Ser Ala Tyr Arg His Gly Val Trp Ser Asn Leu
                165                 170                 175

Glu Leu Glu Asp Ser Glu Ala Glu Glu Met Val Tyr Arg Tyr Arg Leu
            180                 185                 190

Ala Leu Ser Val Met Asp Glu Leu Arg Thr Leu Phe Pro Glu Leu Ser
        195                 200                 205

Ser Thr Asp Glu Glu Leu Gly Lys Thr Glu Arg Glu Leu Leu Ala Met
    210                 215                 220
```

```
Val Ser Ser Ile Gln Ile Asn Trp Ser Val Thr Glu Ser Val Phe Pro
225             230             235             240

Pro Phe Ser Arg Glu Met Phe Asp Arg Phe Arg Ser Ser Pro Pro Asp
            245             250             255

Ser Glu Tyr Ile Thr Arg Ile Val Ser Arg Cys Leu Ile Asn Ser Gln
            260             265         270

Glu Lys Leu Ile Asn Ser Ser Phe Phe Ala Glu Gly Asn Asp Lys Ala
        275             280             285

Leu Arg Phe Ser Lys Asn Ala Glu Glu Cys Ser Leu Ala Val Glu Arg
        290             295             300

Ala Leu Asn Gln Tyr Arg Ala Glu Asp Asn Leu Arg Asp Leu Asn Asp
305             310             315             320

His Lys Ser Thr Ile Gln Leu Pro Pro Trp Leu Ser Tyr His Asp Val
            325             330             335

Asp Gly Lys Asp Leu Cys Pro Leu Gln Gly Leu Asp Val Arg Gly Asp
            340             345             350

His Pro Met Cys Asn Leu Trp Arg Glu Val Val Thr Ser Ala Asn Leu
        355             360             365

Glu Glu Ile Glu Arg Met His Asp Asp Ala Ala Ala Glu Leu Glu Phe
        370             375             380

Ala Leu Ser Gly Val Lys Asp Arg Pro Asp Glu Arg Asn Arg Tyr His
385             390             395             400

Arg Val His Leu Asn Met Gly Ser Asp Asp Ser Val Tyr Ile Ala Ala
            405             410             415

Leu Gly Val Asn Gly Lys Lys His Lys Ala Asp Thr Leu Val Gln Gln
            420             425             430

Met Arg Asp Arg Ser Lys Gln Pro Phe Ser Pro Asp His Asp Val Asp
        435             440             445

His Ile Ser Glu Phe Leu Ser Ala Cys Ser Ser Asp Leu Trp Ala Thr
    450             455             460

Asp Glu Asp Leu Tyr Ser Pro Leu Ser Cys Asp Lys Glu Leu Arg Leu
465             470             475             480

Ala Ala Gln Arg Ile His Gln Pro Ser Leu Ser Glu Arg Gly Phe Asn
            485             490             495

Glu Ile Ile Thr Glu His Tyr Lys Phe Met Gly Ser Arg Ile Gly Ser
            500             505             510

Trp Cys Gln Met Val Ser Leu Ile Gly Ala Glu Leu Ser Ala Ser Val
        515             520             525

Lys Gln His Val Lys Pro Asn Tyr Phe Val Ile Lys Arg Leu Leu Gly
        530             535             540

Ser Gly Ile Phe Leu Leu Ile Lys Pro Thr Ser Ser Lys Ser His Ile
545             550             555             560

Phe Val Ser Phe Ala Ile Lys Arg Ser Cys Trp Ala Phe Asp Leu Ser
            565             570             575

Thr Ser Arg Val Phe Lys Pro Tyr Ile Asp Ala Gly Asp Leu Leu Val
            580             585             590

Thr Asp Phe Val Ser Tyr Lys Leu Ser Lys Leu Thr Asn Leu Cys Lys
        595             600             605

Cys Val Ser Leu Met Glu Ser Ser Phe Ser Phe Trp Ala Glu Ala Phe
        610             615             620

Gly Ile Pro Ser Trp Asn Phe Val Gly Asp Leu Phe Arg Ser Ser Asp
625             630             635             640

Ser Ala Ala Met Asp Ala Ser Tyr Met Gly Lys Leu Ser Leu Leu Thr
```

```
                    645                 650                 655

Leu Leu Glu Asp Lys Ala Ala Thr Glu Glu Leu Gln Thr Ile Ala Arg
                660                 665                 670

Tyr Ile Ile Met Glu Gly Phe Val Ser Pro Pro Glu Ile Pro Lys Pro
            675                 680                 685

His Lys Met Thr Ser Lys Phe Pro Lys Val Leu Arg Ser Glu Leu Gln
        690                 695                 700

Val Tyr Leu Leu Asn Cys Leu Cys Arg Thr Ile Gln Arg Ile Ala Gly
705                 710                 715                 720

Glu Pro Phe Ile Leu Lys Lys Lys Asp Gly Ser Ile Ser Trp Gly Gly
                725                 730                 735

Met Phe Asn Pro Phe Ser Gly Arg Pro Leu Leu Asp Met Gln Pro Leu
            740                 745                 750

Ile Ser Cys Cys Tyr Asn Gly Tyr Phe Lys Asn Lys Glu Glu Glu Thr
        755                 760                 765

Glu Pro Ser Ser Leu Ser Gly Met Tyr Lys Lys Ile Ile Glu Leu Glu
        770                 775                 780

His Leu Arg Pro Gln Ser Asp Ala Phe Leu Gly Tyr Lys Asp Pro Glu
785                 790                 795                 800

Leu Pro Arg Met His Glu Phe Ser Val Ser Tyr Leu Lys Glu Ala Cys
                805                 810                 815

Asn His Ala Lys Leu Val Leu Arg Ser Leu Tyr Gly Gln Asn Phe Met
            820                 825                 830

Glu Gln Ile Asp Asn Gln Ile Ile Arg Glu Leu Ser Gly Leu Thr Leu
            835                 840                 845

Glu Arg Leu Ala Thr Leu Lys Ala Thr Ser Asn Phe Asn Glu Asn Trp
        850                 855                 860

Tyr Val Tyr Lys Asp Val Ala Asp Lys Asn Tyr Thr Arg Asp Lys Leu
865                 870                 875                 880

Leu Val Lys Met Ser Lys Tyr Ala Ser Glu Gly Lys Ser Leu Ala Ile
                885                 890                 895

Gln Lys Phe Glu Asp Cys Met Arg Gln Ile Glu Ser Gln Gly Cys Met
                900                 905                 910

His Ile Cys Leu Phe Lys Lys Gln Gln His Gly Gly Leu Arg Glu Ile
            915                 920                 925

Tyr Val Met Gly Ala Glu Glu Arg Ile Val Gln Ser Val Val Glu Thr
        930                 935                 940

Ile Ala Arg Ser Ile Gly Lys Phe Phe Ala Ser Asp Thr Leu Cys Asn
945                 950                 955                 960

Pro Pro Asn Lys Val Lys Ile Pro Glu Thr His Gly Ile Arg Ala Arg
                965                 970                 975

Lys Gln Cys Lys Gly Pro Val Trp Thr Cys Ala Thr Ser Asp Asp Ala
            980                 985                 990

Arg Lys Trp Asn Gln Gly His Phe Val Thr Lys Phe Ala Leu Met Leu
        995                 1000                1005

Cys Glu Phe Thr Ser Pro Lys Trp Trp Pro Leu Ile Ile Arg Gly
    1010                1015                1020

Cys Ser Met Phe Thr Arg Lys Arg Met Met Met Asn Leu Asn Tyr
    1025                1030                1035

Leu Lys Ile Leu Asp Gly His Arg Glu Leu Asp Ile Arg Asp Asp
    1040                1045                1050

Phe Val Met Asp Leu Phe Lys Ala Tyr His Gly Glu Ala Glu Val
    1055                1060                1065
```

-continued

```
Pro Trp Ala Phe Lys Gly Lys Thr Tyr Leu Glu Thr   Thr Thr Gly
1070              1075              1080

Met Met Gln Gly Ile Leu His Tyr Thr Ser Ser Leu   Leu His Thr
1085              1090              1095

Ile His Gln Glu Tyr Ile Arg Ser Leu Ser Phe Lys   Ile Phe Asn
1100              1105              1110

Leu Lys Val Ala Pro Glu Met Ser Lys Ser Leu Val   Cys Asp Met
1115              1120              1125

Met Gln Gly Ser Asp Asp Ser Ser Met Leu Ile Ser   Phe Pro Ala
1130              1135              1140

Asp Asp Glu Lys Val Leu Thr Arg Cys Lys Val Ala   Ala Ala Ile
1145              1150              1155

Cys Phe Arg Met Lys Lys Glu Leu Gly Val Tyr Leu   Ala Ile Tyr
1160              1165              1170

Pro Ser Glu Lys Ser Thr Ala Asn Thr Asp Phe Val   Met Glu Tyr
1175              1180              1185

Asn Ser Glu Phe Tyr Phe His Thr Gln His Val Arg   Pro Thr Ile
1190              1195              1200

Arg Trp Ile Ala Ala Cys Cys Ser Leu Pro Glu Val   Glu Thr Leu
1205              1210              1215

Val Ala Arg Gln Glu Glu Ala Ser Asn Leu Met Thr   Ser Val Thr
1220              1225              1230

Glu Gly Gly Gly Ser Phe Ser Leu Ala Ala Met Ile   Gln Gln Ala
1235              1240              1245

Gln Cys Thr Leu His Tyr Met Leu Met Gly Met Gly   Val Ser Glu
1250              1255              1260

Leu Phe Leu Glu Tyr Lys Lys Ala Val Leu Lys Trp   Asn Asp Pro
1265              1270              1275

Gly Leu Gly Phe Phe Leu Leu Asp Asn Pro Tyr Ala   Cys Gly Leu
1280              1285              1290

Gly Gly Phe Arg Phe Asn Leu Phe Lys Ala Ile Thr   Arg Thr Asp
1295              1300              1305

Leu Gln Lys Leu Tyr Ala Phe Phe Met Lys Lys Val   Lys Gly Ser
1310              1315              1320

Ala Ala Arg Asp Trp Ala Asp Glu Asp Val Thr Ile   Pro Glu Thr
1325              1330              1335

Cys Ser Val Ser Pro Gly Gly Ala Leu Ile Leu Ser   Ser Ser Leu
1340              1345              1350

Lys Trp Gly Ser Arg Lys Lys Phe Gln Lys Leu Arg   Asp Arg Leu
1355              1360              1365

Asn Ile Pro Glu Asn Trp Ile Glu Leu Ile Asn Glu   Asn Pro Glu
1370              1375              1380

Val Leu Tyr Arg Ala Pro Arg Thr Gly Pro Glu Ile   Leu Leu Arg
1385              1390              1395

Ile Ala Glu Lys Val His Ser Pro Gly Val Val Ser   Ser Leu Ser
1400              1405              1410

Ser Gly Asn Ala Val Cys Lys Val Met Ala Ser Ala   Val Tyr Phe
1415              1420              1425

Leu Ser Ala Thr Ile Phe Glu Asp Thr Gly Arg Pro   Glu Phe Asn
1430              1435              1440

Phe Leu Glu Asp Ser Lys Tyr Ser Leu Leu Gln Lys   Met Ala Ala
1445              1450              1455
```

-continued

```
Tyr Ser Gly Phe His Gly Phe  Asn Asp Met Glu Pro  Glu Asp Ile
    1460              1465                1470

Leu Phe Leu Phe Pro Asn Ile  Glu Glu Leu Glu Ser  Leu Asp Ser
    1475              1480                1485

Ile Val Tyr Asn Lys Gly Glu  Ile Asp Ile Ile Pro  Arg Val Asn
    1490              1495                1500

Ile Arg Asp Ala Thr Gln Thr  Arg Val Thr Ile Phe  Asn Glu Gln
    1505              1510                1515

Lys Thr Leu Arg Thr Ser Pro  Glu Lys Leu Val Ser  Asp Lys Trp
    1520              1525                1530

Phe Gly Thr Gln Lys Ser Arg  Ile Gly Lys Thr Thr  Phe Leu Ala
    1535              1540                1545

Glu Trp Glu Lys Leu Lys Lys  Ile Val Lys Trp Leu  Glu Asp Thr
    1550              1555                1560

Pro Glu Ala Thr Leu Ala His  Thr Pro Leu Asn Asn  His Ile Gln
    1565              1570                1575

Val Arg Asn Phe Phe Ala Arg  Met Glu Ser Lys Pro  Arg Thr Val
    1580              1585                1590

Arg Ile Thr Gly Ala Pro Val  Lys Lys Arg Ser Gly  Val Ser Lys
    1595              1600                1605

Ile Ala Met Val Ile Arg Asp  Asn Phe Ser Arg Met  Gly His Leu
    1610              1615                1620

Arg Gly Val Glu Asp Leu Ala  Gly Phe Thr Arg Ser  Val Ser Ala
    1625              1630                1635

Glu Ile Leu Lys His Phe Leu  Phe Cys Ile Leu Gln  Gly Pro Tyr
    1640              1645                1650

Ser Glu Ser Tyr Lys Leu Gln  Leu Ile Tyr Arg Val  Leu Ser Ser
    1655              1660                1665

Val Ser Asn Val Glu Ile Lys  Glu Ser Asp Gly Lys  Thr Lys Thr
    1670              1675                1680

Asn Leu Ile Gly Ile Leu Gln  Arg Phe Leu Asp Gly  Asp His Val
    1685              1690                1695

Val Pro Ile Ile Glu Glu Met  Gly Ala Gly Thr Val  Gly Gly Phe
    1700              1705                1710

Ile Lys Arg Gln Gln Ser Lys  Val Val Gln Asn Lys  Val Val Tyr
    1715              1720                1725

Tyr Gly Val Gly Ile Trp Arg  Gly Phe Met Asp Gly  Tyr Gln Val
    1730              1735                1740

His Leu Glu Ile Glu Asn Asp  Ile Gly Gln Pro Pro  Arg Leu Arg
    1745              1750                1755

Asn Val Thr Thr Asn Cys Gln  Ser Ser Pro Trp Asp  Leu Ser Ile
    1760              1765                1770

Pro Ile Arg Gln Trp Ala Glu  Asp Met Gly Val Thr  Asn Asn Gln
    1775              1780                1785

Asp Tyr Ser Ser Lys Ser Ser  Arg Gly Ala Arg Tyr  Trp Met His
    1790              1795                1800

Ser Phe Arg Met Gln Gly Pro  Ser Lys Pro Phe Gly  Cys Pro Val
    1805              1810                1815

Tyr Ile Ile Lys Gly Asp Met  Ser Asp Val Ile Arg  Leu Arg Lys
    1820              1825                1830

Glu Glu Val Glu Met Lys Val  Arg Gly Ser Thr Leu  Asn Leu Tyr
    1835              1840                1845

Thr Lys His His Ser His Gln  Asp Leu His Ile Leu  Ser Tyr Thr
```

```
          1850             1855              1860

Ala  Ser   Asp Asn Asp Leu Ser  Pro Gly Ile Phe Lys  Ser Ile Ser
          1865             1870              1875

Asp Glu   Gly Val Ala Gln Ala  Leu Gln Leu Phe Glu  Arg Glu Pro
          1880             1885              1890

Ser Asn   Cys Trp Val Arg Cys  Glu Ser Val Ala Pro  Lys Phe Ile
          1895             1900              1905

Ser Ala   Ile Leu Glu Ile Cys  Glu Gly Lys Arg Gln  Ile Lys Gly
          1910             1915              1920

Ile Asn   Arg Thr Arg Leu Ser  Glu Ile Val Arg Ile  Cys Ser Glu
          1925             1930              1935

Ser Ser   Leu Arg Ser Lys Val  Gly Ser Met Phe Ser  Phe Val Ala
          1940             1945              1950

Asn Val   Glu Glu Ala His Asp  Val Asp Tyr Asp Ala  Leu Met Asp
          1955             1960              1965

Leu Met   Ile Glu Asp Ala Lys  Asn Asn Ala Phe Ser  His Val Val
          1970             1975              1980

Asp Cys   Ile Glu Leu Asp Val  Ser Gly Pro Tyr Glu  Met Glu Ser
          1985             1990              1995

Phe Asp   Thr Ser Asp Val Asn  Leu Phe Gly Pro Ala  His Tyr Lys
          2000             2005              2010

Asp Ile   Ser Ser Leu Ser Met  Ile Ala His Pro Leu  Met Asp Lys
          2015             2020              2025

Phe Val   Asp Tyr Ala Ile Ser  Lys Met Gly Arg Ala  Ser Val Arg
          2030             2035              2040

Lys Val   Leu Glu Thr Gly Arg  Cys Ser Ser Lys Asp  Tyr Asp Leu
          2045             2050              2055

Ser Lys   Val Leu Phe Arg Thr  Leu Gln Arg Pro Glu  Glu Ser Ile
          2060             2065              2070

Arg Ile   Asp Asp Leu Glu Leu  Tyr Glu Glu Thr Asp  Val Ala Asp
          2075             2080              2085

Asp Met   Leu Gly
          2090
```

```
<210> SEQ ID NO 55
<211> LENGTH: 1197
<212> TYPE: PRT
<213> ORGANISM: Artificial Sequence
<220> FEATURE:
<223> OTHER INFORMATION: ZH548 RVFV M (poly)protein

<400> SEQUENCE: 55

Met Tyr Val Leu Leu Thr Ile Leu Ile Ser Val Leu Val Cys Glu Ala
1               5                   10                  15

Val Ile Arg Val Ser Leu Ser Ser Thr Arg Glu Glu Thr Cys Phe Gly
            20                  25                  30

Asp Ser Thr Asn Pro Glu Met Ile Glu Gly Ala Trp Asp Ser Leu Arg
        35                  40                  45

Glu Glu Glu Met Pro Glu Glu Leu Ser Cys Ser Ile Ser Gly Ile Arg
    50                  55                  60

Glu Val Lys Thr Ser Ser Gln Glu Leu Tyr Arg Ala Leu Lys Ala Ile
65                  70                  75                  80

Ile Ala Ala Asp Gly Leu Asn Asn Ile Thr Cys His Gly Lys Asp Pro
                85                  90                  95

Glu Asp Lys Ile Ser Leu Ile Lys Gly Pro Pro His Lys Lys Arg Val
```

```
                100               105               110

Gly Ile Val Arg Cys Glu Arg Arg Asp Ala Lys Gln Ile Gly Arg
        115               120               125

Glu Thr Met Ala Gly Ile Ala Met Thr Val Leu Pro Ala Leu Ala Val
    130               135               140

Phe Ala Leu Ala Pro Val Val Phe Ala Glu Asp Pro His Leu Arg Asn
145               150               155               160

Arg Pro Gly Lys Gly His Asn Tyr Ile Asp Gly Met Thr Gln Glu Asp
            165               170               175

Ala Thr Cys Lys Pro Val Thr Tyr Ala Gly Ala Cys Ser Ser Phe Asp
            180               185               190

Val Leu Leu Glu Lys Gly Lys Phe Pro Leu Phe Gln Ser Tyr Ala His
        195               200               205

His Arg Thr Leu Leu Glu Ala Val His Asp Thr Ile Ile Ala Lys Ala
        210               215               220

Asp Pro Pro Ser Cys Asp Leu Leu Ser Ala His Gly Asn Pro Cys Met
225               230               235               240

Lys Glu Lys Leu Val Met Lys Thr His Cys Pro Asn Asp Tyr Gln Ser
            245               250               255

Ala His Tyr Leu Asn Asn Asp Gly Lys Met Ala Ser Val Lys Cys Pro
            260               265               270

Pro Lys Tyr Glu Leu Thr Glu Asp Cys Asn Phe Cys Arg Gln Met Thr
            275               280               285

Gly Ala Ser Leu Lys Lys Gly Ser Tyr Pro Leu Gln Asp Leu Phe Cys
        290               295               300

Gln Ser Ser Glu Asp Asp Gly Ser Lys Leu Lys Thr Lys Met Lys Gly
305               310               315               320

Val Cys Glu Val Gly Val Gln Ala Leu Lys Lys Cys Asp Gly Gln Leu
            325               330               335

Ser Thr Ala His Glu Val Val Pro Phe Ala Val Phe Lys Asn Ser Lys
            340               345               350

Lys Val Tyr Leu Asp Lys Leu Asp Leu Lys Thr Glu Glu Asn Leu Leu
        355               360               365

Pro Asp Ser Phe Val Cys Phe Glu His Lys Gly Gln Tyr Lys Gly Thr
    370               375               380

Met Asp Ser Gly Gln Thr Lys Arg Glu Leu Lys Ser Phe Asp Ile Ser
385               390               395               400

Gln Cys Pro Lys Ile Gly Gly His Gly Ser Lys Lys Cys Thr Gly Asp
            405               410               415

Ala Ala Phe Cys Ser Ala Tyr Glu Cys Thr Ala Gln Tyr Ala Asn Ala
            420               425               430

Tyr Cys Ser His Ala Asn Gly Ser Gly Ile Val Gln Ile Gln Val Ser
            435               440               445

Gly Val Trp Lys Lys Pro Leu Cys Val Gly Tyr Glu Arg Val Val Val
        450               455               460

Lys Arg Glu Leu Ser Ala Lys Pro Ile Gln Arg Val Glu Pro Cys Thr
465               470               475               480

Thr Cys Ile Thr Lys Cys Glu Pro His Gly Leu Val Val Arg Ser Thr
            485               490               495

Gly Phe Lys Ile Ser Ser Ala Val Ala Cys Ala Ser Gly Val Cys Val
            500               505               510

Thr Gly Ser Gln Ser Pro Ser Thr Glu Ile Thr Leu Lys Tyr Pro Gly
            515               520               525
```

-continued

```
Ile Ser Gln Ser Ser Gly Gly Asp Ile Gly Val His Met Ala His Asp
    530               535               540

Asp Gln Ser Val Ser Ser Lys Ile Val Ala His Cys Pro Pro Gln Asp
545               550               555               560

Pro Cys Leu Val His Asp Cys Ile Val Cys Ala His Gly Leu Ile Asn
            565               570               575

Tyr Gln Cys His Thr Ala Leu Ser Ala Phe Val Val Val Phe Val Phe
            580               585               590

Ser Ser Ile Ala Ile Ile Cys Leu Ala Ile Leu Tyr Arg Val Leu Lys
        595               600               605

Cys Leu Lys Ile Ala Pro Arg Lys Val Leu Asn Pro Leu Met Trp Ile
    610               615               620

Thr Ala Phe Ile Arg Trp Ile Tyr Lys Lys Met Val Ala Arg Val Ala
625               630               635               640

Asp Asn Ile Asn Gln Val Asn Arg Glu Ile Gly Trp Met Glu Gly Gly
            645               650               655

Gln Leu Val Leu Gly Asn Pro Ala Pro Ile Pro Arg His Ala Pro Ile
        660               665               670

Pro Arg Tyr Ser Thr Tyr Leu Met Leu Leu Leu Ile Val Ser Tyr Ala
        675               680               685

Ser Ala Cys Ser Glu Leu Ile Gln Ala Ser Ser Arg Ile Thr Thr Cys
    690               695               700

Ser Thr Glu Gly Val Asn Thr Lys Cys Arg Leu Ser Gly Thr Ala Leu
705               710               715               720

Ile Arg Ala Gly Ser Val Gly Ala Glu Ala Cys Leu Met Leu Lys Gly
            725               730               735

Val Lys Glu Asp Gln Thr Lys Phe Leu Lys Ile Lys Thr Val Ser Ser
            740               745               750

Glu Leu Ser Cys Arg Glu Gly Gln Ser Tyr Trp Thr Gly Ser Phe Ser
        755               760               765

Pro Lys Cys Leu Ser Ser Arg Arg Cys His Leu Val Gly Glu Cys His
    770               775               780

Val Asn Arg Cys Leu Ser Trp Arg Asp Asn Glu Thr Ser Ala Glu Phe
785               790               795               800

Ser Phe Val Gly Glu Ser Thr Thr Met Arg Glu Asn Lys Cys Phe Glu
            805               810               815

Gln Cys Gly Gly Trp Gly Cys Gly Cys Phe Asn Val Asn Pro Ser Cys
            820               825               830

Leu Phe Val His Thr Tyr Leu Gln Ser Val Arg Lys Glu Ala Leu Arg
            835               840               845

Val Phe Asn Cys Ile Asp Trp Val His Lys Leu Thr Leu Glu Ile Thr
    850               855               860

Asp Phe Asp Gly Ser Val Ser Thr Ile Asp Leu Gly Ala Ser Ser Ser
865               870               875               880

Arg Phe Thr Asn Trp Gly Ser Val Ser Leu Ser Leu Asp Ala Glu Gly
            885               890               895

Ile Ser Gly Ser Asn Ser Phe Ser Phe Ile Glu Ser Pro Gly Lys Gly
            900               905               910

Tyr Ala Ile Val Asp Glu Pro Phe Ser Glu Ile Pro Arg Gln Gly Phe
        915               920               925

Leu Gly Glu Ile Arg Cys Asn Ser Glu Ser Ser Val Leu Ser Ala His
    930               935               940
```

```
Glu Ser Cys Leu Arg Ala Pro Asn Leu Ile Ser Tyr Lys Pro Met Ile
945             950             955             960

Asp Gln Leu Glu Cys Thr Thr Asn Leu Ile Asp Pro Phe Val Val Phe
            965             970             975

Glu Arg Gly Ser Leu Pro Gln Thr Arg Asn Asp Lys Thr Phe Ala Ala
            980             985             990

Ser Lys Gly Asn Arg Gly Val Gln Ala Phe Ser Lys Gly Ser Val Gln
        995             1000            1005

Ala Asp Leu Thr Leu Met Phe Asp Asn Phe Glu Val Asp Phe Val
    1010            1015            1020

Gly Ala Ala Val Ser Cys Asp Ala Ala Phe Leu Asn Leu Thr Gly
    1025            1030            1035

Cys Tyr Ser Cys Asn Ala Gly Ala Arg Val Cys Leu Ser Ile Thr
    1040            1045            1050

Ser Thr Gly Thr Gly Ser Leu Ser Ala His Asn Lys Asp Gly Ser
    1055            1060            1065

Leu His Ile Val Leu Pro Ser Glu Asn Gly Thr Lys Asp Gln Cys
    1070            1075            1080

Gln Ile Leu His Phe Thr Val Pro Glu Val Glu Glu Glu Phe Met
    1085            1090            1095

Tyr Ser Cys Asp Gly Asp Glu Arg Pro Leu Leu Val Lys Gly Thr
    1100            1105            1110

Leu Ile Ala Ile Asp Pro Phe Asp Asp Arg Arg Glu Ala Gly Gly
    1115            1120            1125

Glu Ser Thr Val Val Asn Pro Lys Ser Gly Ser Trp Asn Phe Phe
    1130            1135            1140

Asp Trp Phe Ser Gly Leu Met Ser Trp Phe Gly Gly Pro Leu Lys
    1145            1150            1155

Thr Ile Leu Leu Ile Cys Leu Tyr Val Ala Leu Ser Ile Gly Leu
    1160            1165            1170

Phe Phe Leu Leu Ile Tyr Leu Gly Arg Thr Gly Leu Ser Lys Met
    1175            1180            1185

Trp Leu Ala Ala Thr Lys Lys Ala Ser
    1190            1195
```

```
<210> SEQ ID NO 56
<211> LENGTH: 265
<212> TYPE: PRT
<213> ORGANISM: Artificial Sequence
<220> FEATURE:
<223> OTHER INFORMATION: ZH548 RVFV NSs protein

<400> SEQUENCE: 56

Met Asp Tyr Phe Pro Val Ile Ser Val Asp Leu Gln Ser Gly Arg Arg
1               5               10              15

Val Val Ser Val Glu Tyr Phe Arg Gly Asp Gly Pro Pro Arg Ile Pro
            20              25              30

Tyr Ser Met Val Gly Pro Cys Cys Val Phe Leu Met His Arg Pro
        35              40              45

Ser His Glu Val Arg Leu Arg Phe Ser Asp Phe Tyr Asn Val Gly Glu
    50              55              60

Phe Pro Tyr Arg Val Gly Leu Gly Asp Phe Ala Ser Asn Val Ala Pro
65              70              75              80

Pro Pro Ala Lys Pro Phe Gln Arg Leu Ile Asp Leu Ile Gly His Met
            85              90              95
```

-continued

```
Thr Leu Ser Asp Phe Thr Arg Phe Pro Asn Leu Lys Glu Ala Ile Ser
            100                 105                 110

Trp Pro Leu Gly Glu Pro Ser Leu Ala Phe Phe Asp Leu Ser Ser Thr
            115                 120                 125

Arg Val His Arg Asn Asp Asp Ile Arg Arg Asp Gln Ile Ala Thr Leu
            130                 135                 140

Ala Met Arg Ser Cys Lys Ile Thr Asn Asp Leu Glu Asp Ser Phe Val
145                 150                 155                 160

Gly Leu His Arg Met Ile Ala Thr Glu Ala Ile Leu Arg Gly Ile Asp
                165                 170                 175

Leu Cys Leu Leu Pro Gly Phe Asp Leu Met Tyr Glu Val Ala His Val
            180                 185                 190

Gln Cys Val Arg Leu Leu Gln Ala Ala Lys Glu Asp Ile Ser Asn Ala
            195                 200                 205

Val Val Pro Asn Ser Ala Leu Ile Val Leu Met Glu Glu Ser Leu Met
            210                 215                 220

Leu Arg Ser Ser Leu Pro Ser Met Met Gly Arg Asn Asn Trp Ile Pro
225                 230                 235                 240

Val Ile Pro Pro Ile Pro Asp Val Glu Met Glu Ser Glu Glu Glu Ser
                245                 250                 255

Asp Asp Asp Gly Phe Val Glu Val Asp
                260                 265

<210> SEQ ID NO 57
<211> LENGTH: 245
<212> TYPE: PRT
<213> ORGANISM: Artificial Sequence
<220> FEATURE:
<223> OTHER INFORMATION: ZH548 RVFV N protein

<400> SEQUENCE: 57

Met Asp Asn Tyr Gln Glu Leu Ala Ile Gln Phe Ala Ala Gln Ala Val
1               5                   10                  15

Asp Arg Asn Glu Ile Glu Gln Trp Val Arg Glu Phe Ala Tyr Gln Gly
            20                  25                  30

Phe Asp Ala Arg Arg Val Ile Glu Leu Leu Lys Gln Tyr Gly Gly Ala
            35                  40                  45

Asp Trp Glu Lys Asp Ala Lys Lys Met Ile Val Leu Ala Leu Thr Arg
            50                  55                  60

Gly Asn Lys Pro Arg Arg Met Met Met Lys Met Ser Lys Glu Gly Lys
65                  70                  75                  80

Ala Thr Val Glu Ala Leu Ile Asn Lys Tyr Lys Leu Lys Glu Gly Asn
                85                  90                  95

Pro Ser Arg Asp Glu Leu Thr Leu Ser Arg Val Ala Ala Ala Leu Ala
            100                 105                 110

Gly Trp Thr Cys Gln Ala Leu Val Val Leu Ser Glu Trp Leu Pro Val
            115                 120                 125

Thr Gly Thr Thr Met Asp Gly Leu Ser Pro Ala Tyr Pro Arg His Met
            130                 135                 140

Met His Pro Ser Phe Ala Gly Met Val Asp Pro Ser Leu Pro Gly Asp
145                 150                 155                 160

Tyr Leu Arg Ala Ile Leu Asp Ala His Ser Leu Tyr Leu Leu Gln Phe
                165                 170                 175

Ser Arg Val Ile Asn Pro Asn Leu Arg Gly Arg Thr Lys Glu Glu Val
            180                 185                 190
```

-continued

```
Ala Ala Thr Phe Thr Gln Pro Met Asn Ala Ala Val Asn Ser Asn Phe
        195                 200                 205

Ile Ser His Glu Lys Arg Arg Glu Phe Leu Lys Ala Phe Gly Leu Val
    210                 215                 220

Asp Ser Asn Gly Lys Pro Ser Ala Ala Val Met Ala Ala Ala Gln Ala
225                 230                 235                 240

Tyr Lys Thr Ala Ala
            245
```